US008841265B2

(12) United States Patent
Chan et al.

(10) Patent No.: US 8,841,265 B2
(45) Date of Patent: *Sep. 23, 2014

(54) COMPOSITION COMPRISING TRITERPENE SAPONINS AND COMPOUNDS WITH ANGELOYL FUNCTIONAL GROUP, METHODS FOR PREPARING SAME AND USES THEREOF

(75) Inventors: Pui-Kwong Chan, Sugarland, TX (US); May Sung Mak, Kowloon (HK); Yun Wang, Dunedin (NZ)

(73) Assignee: Pacific Arrow Limited (CN)

( * ) Notice: Subject to any disclaimer, the term of this patent is extended or adjusted under 35 U.S.C. 154(b) by 733 days.

This patent is subject to a terminal disclaimer.

(21) Appl. No.: 12/344,682

(22) Filed: Dec. 29, 2008

(65) Prior Publication Data
US 2009/0156515 A1 Jun. 18, 2009

Related U.S. Application Data

(63) Continuation of application No. 11/289,142, filed on Nov. 28, 2005, now Pat. No. 7,488,753, which is a continuation-in-part of application No. PCT/US2005/031900, filed on Sep. 7, 2005, and a continuation-in-part of application No. 11/267,523, filed on Nov. 4, 2005, now abandoned, and a continuation-in-part of application No. 11/131,551, filed on May 17, 2005, now Pat. No. 7,262,285, and a continuation-in-part of application No. 11/117,760, filed on Apr. 27, 2005, now Pat. No. 7,727,561, and a continuation-in-part of application No. 10/906,303, filed on Feb. 14, 2005, now Pat. No. 7,524,824, and a continuation-in-part of application No. PCT/US2004/043465, filed on Dec. 23, 2004, which is a continuation-in-part of application No. PCT/US2004/033359, filed on Oct. 8, 2004.

(60) Provisional application No. 60/532,101, filed on Dec. 23, 2003, provisional application No. 60/509,851, filed on Oct. 9, 2003, provisional application No. 60/613,811, filed on Sep. 27, 2004, provisional application No. 60/607,858, filed on Sep. 7, 2004, provisional application No. 60/675,282, filed on Apr. 27, 2005, provisional application No. 60/675,284, filed on Apr. 27, 2005, provisional application No. 60/617,379, filed on Oct. 8, 2004.

(51) Int. Cl.
*A61K 31/575* (2006.01)
*C07J 9/00* (2006.01)
*C07H 15/256* (2006.01)
*C07C 13/62* (2006.01)

(52) U.S. Cl.
CPC ............... *A61K 31/575* (2013.01); *C07J 9/00* (2013.01); *C07H 15/256* (2013.01); *C07C 2103/52* (2013.01)
USPC .............................. 514/33; 536/4.4; 536/18.1

(58) Field of Classification Search
None
See application file for complete search history.

(56) References Cited

U.S. PATENT DOCUMENTS

| | | | |
|---|---|---|---|
| 6,197,306 B1 | 3/2001 | Murali et al. | |
| 6,231,859 B1 | 5/2001 | Kensil | |
| 6,444,233 B1 | 9/2002 | Arntzen et al. | |
| 6,689,398 B2 | 2/2004 | Haridas et al. | |
| 6,746,696 B2 | 6/2004 | Arntzen et al. | |
| 6,962,720 B2 | 11/2005 | Haridas et al. | |
| 7,105,186 B2 | 9/2006 | Arntzen et al. | |
| 7,262,285 B2 * | 8/2007 | Chan et al. | 536/18.1 |
| 7,488,753 B2 * | 2/2009 | Chan et al. | 514/510 |
| 7,514,412 B2 * | 4/2009 | Chan et al. | 514/33 |
| 7,524,824 B2 * | 4/2009 | Chan et al. | 514/33 |
| 7,670,632 B2 | 3/2010 | Arntzen et al. | |
| 7,727,561 B2 * | 6/2010 | Chan et al. | 424/725 |
| 7,780,974 B2 | 8/2010 | Gutterman et al. | |
| 8,334,269 B2 | 12/2012 | Chan et al. | |
| 8,586,719 B2 | 11/2013 | Chan et al. | |
| 2004/0138151 A1 | 7/2004 | Maes et al. | |
| 2005/0209445 A1 | 9/2005 | Gokaraju et al. | |
| 2005/0277601 A1 | 12/2005 | Chan et al. | |
| 2006/0183687 A1 | 8/2006 | Cory | |
| 2007/0161580 A1 * | 7/2007 | Chan et al. | 514/33 |
| 2007/0196517 A1 | 8/2007 | San Martin | |
| 2007/0212329 A1 | 9/2007 | Bruck et al. | |
| 2007/0243269 A1 | 10/2007 | McNeff et al. | |
| 2007/0245470 A1 | 10/2007 | Nguyen et al. | |
| 2007/0249711 A1 | 10/2007 | Choi et al. | |
| 2007/0254847 A1 | 11/2007 | Liu et al. | |
| 2008/0058273 A1 | 3/2008 | Yang et al. | |

(Continued)

FOREIGN PATENT DOCUMENTS

| | | |
|---|---|---|
| AU | 2004281707 | 9/2011 |
| AU | 2009200988 | 3/2013 |

(Continued)

OTHER PUBLICATIONS

D'Acquarica et al., "Isolation and structure elucidation of four new triterpenoid estersaponins from fruits of *Pittosporum tobira* AIT" Tetrahedron (2002) vol. 58 pp. 10127-10136.*
U.S. Appl. No. 60/795,417, Apr. 27, 2006, Mak et al.
U.S. Appl. No. 60/890,380, Feb. 16, 2007, Chan et al.
U.S. Appl. No. 60/947,705. Jul. 3, 2007, Chan et al.
U.S. Appl. No. 12/856,322, Aug. 13, 2010, Chan et al.
U.S. Appl. No. 12/392,795, Mar. 20, 2009, Chan et al.

(Continued)

*Primary Examiner* — Eric S Olson
(74) *Attorney, Agent, or Firm* — Law Offices of Albert Wai-Kit Chan, PLLC

(57) ABSTRACT

This invention provides a composition comprising a triterpenoid saponin, comprising two side groups attached to carbons 21, and 22 of the triterpenoid saponin backbone, for inhibiting skin or ovarian tumor cell growth.

23 Claims, 34 Drawing Sheets

(56) References Cited

U.S. PATENT DOCUMENTS

| | | | |
|---|---|---|---|
| 2008/0064762 | A1 | 3/2008 | Fuchs et al. |
| 2008/0096938 | A1 | 4/2008 | Evindar et al. |
| 2008/0112925 | A1 | 5/2008 | Hancock |
| 2008/0119420 | A1 | 5/2008 | Liu et al. |
| 2009/0041877 | A1 | 2/2009 | Mak et al. |
| 2010/0004190 | A1* | 1/2010 | Chan et al. ............ 514/33 |
| 2010/0204169 | A1* | 8/2010 | Chan et al. ............ 514/33 |
| 2010/0317606 | A1* | 12/2010 | Chan et al. ............ 514/33 |

FOREIGN PATENT DOCUMENTS

| | | |
|---|---|---|
| CA | 2541425 | 1/2013 |
| CN | ZL 02142258.3 | 8/2002 |
| CN | ZL 02142258.3 | 1/2006 |
| JP | 61-007285 | 1/1986 |
| JP | 61-130232 | 6/1986 |
| JP | 2002-247196 | 10/1990 |
| JP | 2002-515430 A | 5/2002 |
| JP | 2006-070018 | 3/2006 |
| JP | 4815558 | 9/2011 |
| JP | 4880479 B2 | 2/2012 |
| JP | 5087400 | 9/2012 |
| KR | 10-1135824 | 4/2012 |
| NZ | 546138 | 4/2010 |
| NZ | 554037 | 8/2011 |
| SG | 120666 | 10/2008 |
| SG | 130542 | 1/2010 |
| TW | 091119471 | 8/2002 |
| WO | 00/38700 A1 | 7/2000 |
| WO | PCT/US2008/02086 | 2/2008 |
| WO | WO 2008/028060 A2 | 3/2008 |
| WO | 2011/009032 | 1/2011 |

OTHER PUBLICATIONS

U.S. Office Action for Mak, et al., U.S. Appl. No. 11/412,659, filed Apr. 27, 2006, Dated Mar. 8, 2007.
U.S. Office Action for Chan, et al., U.S. Appl. No. 10/906,303, filed Feb. 14, 2005, Dated Feb. 12, 2007.
U.S. Office Communication for Chan, et al., U.S. Appl. No. 11/117,760, filed Apr. 27, 2005, Dated Feb. 8, 2008.
Office Action for Mak, et al., U.S. Appl. No. 11/412,659, filed Apr. 27, 2006, Dated Feb. 20, 2008.
U.S. Office Action for Chan, et al., U.S. Appl. No. 10/906,303, filed Feb. 14, 2005, Dated Jul. 27, 2007.
U.S. Office Action for Chan, et al., U.S. Appl. No. 11/117,760, filed Apr. 27, 2005, Dated Mar. 18, 2009.
U.S. Office Action for Chan, et al., U.S. Appl. No. 11/683,198, filed Mar. 7, 2007, Dated May 1, 2009.
U.S. Office Action for Mak, et al., U.S. Appl. No. 12/195,112, filed Aug. 20, 2008, Dated May 19, 2009.
U.S. Office Action for Chan, et al., U.S. Appl. No. 11/683,198, filed Mar. 7, 2007, Dated Feb. 18, 2010.
U.S. Office Action for Mak, et al., U.S. Appl. No. 12/195,112, filed Aug. 20, 2008, Dated Feb. 18, 2010.
U.S. Office Action for Chan, et al., U.S. Appl. No. 11/683,198, filed Mar. 7, 2007, Dated Sep. 10, 2008.
U.S. Office Action, May 20, 2011, for Chan et al., U.S. Appl. No. 12/392,795, filed Feb, 25, 2009.
Notice of Allowability for Chan et al., U.S. Appl. No. 11/683,198, filed Mar. 7, 2007, Dated May 5, 2011.
PCT International Preliminary Report on Patentability for Pacific Arrow Limited et al., Intl App'l No. PCT/US2004/033359, filed Oct. 8, 2004, Dated Apr. 11, 2006.
PCT International Search Report issued on Jul. 7, 2008 for Pacific Arrow Limited et al., Int'l App'l No. PCT/US2008/002086.
PCT Written Opinion of the International Searching Authority issued on Jul. 7, 2008 for Pacific Arrow Limited et al., Int'l App'l No. PCT/US2008/002086.
Australian Letters Patent No. 2002348988, Nov. 8, 2007, Wang, Yun, "Composition comprising Wenguanguo Extracts, Methods for Preparing Same and Uses Thereof".
New Zealand Letters Patent No. 530449, Oct. 11, 2007, Wang, Yun, "Composition comprising Wenguanguo Extracts, Methods for Preparing Same and Uses Thereof".
Chinese Office Action for Wang, Yun, Chinese Publication No. CN 1236792C, filed Jan. 18, 2006, Dated Aug. 27, 2004.
Chinese Office Action for Wang, Yun, Chinese Publication No. CN 1236792C, filed Jan. 18, 2006, Dated May 27, 2005.
Taiwan Office Action for Wang, Yun, Taiwan Application No. 091119471, filed Aug. 28, 2002, Dated Sep. 14, 2004.
Taiwan Office Action for Wang, Yun, Taiwan Application No. 091119471, filed Aug. 28, 2002, Dated Apr. 26, 2005.
PCT International Search Report for Pacific Arrow Limited et al,, International App'l No. PCT/US07/77273, filed Aug. 30, 2007, Dated Aug. 4, 2008.
PCT Written Opinion of the International Searching Authority for Pacific Arrow Limited et al., International App'l No. PCT/US07/77273, filed Aug. 30, 2007, Dated Aug. 4, 2008.
New Zealand Office Action, May 8, 2009, for New Zealand Application No. 554037, filed Sep. 7, 2005.
Japan Office Action for Japan Patent Application No. 2003-522442, Nov. 4, 2008, International No. PCT/IB02/04750, filed Aug. 28, 2002, Fountain Silver Limited, "Composition Comprising Wenguanoguo Extracts, Methods for Perparing Same and Uses Thereof".
Korean Office Action for Korean Application No. 10-2004-7002889, Nov. 21, 2008, International Application No. PCT/IB02/04750, filed Aug. 28, 2002, Fountain Silver Limited, "Composition Comprising Wenguanoguo Extracts, Methods for Perparing Same and Uses Thereof".
Canadian Office Action for Canadian Application No. 2,451,740, Nov. 7, 2008, Fountain Silver Limited, "Composition Comprising Wenguanoguo Extracts, Methods for Perparing Same and Uses Thereof".
New Zealand Office Action, Aug. 12, 2009, New Zealand Application No. 546138, filed Mar. 22, 2007.
New Zealand Office Action, Sep. 22, 2009, New Zealand Application No. 546138, filed Mar. 27, 2006.
Supplementary European Search Report issued on Oct. 13, 2009 for Pacific Arrow Limited et al., European Patent Application No. 04815530.3.
Supplementary European Search Report issued on Oct. 13, 2009 for Pacific Arrow Limited et al., European Patent Application No. 04809909.7.
PCT Written Opinion of the International Searching Authority, Jun. 2, 2009, International App'l No. PCT/US09/34115, filed Feb. 13, 2009.
PCT Written Opinion of the International Searching Authority, Aug. 4, 2008, International App'l No. PCT/US07/77273, filed Aug. 30, 2007.
Notice of Allowability for Chan et al., U.S. Appl. No. 10/906,303, filed Feb. 14, 2005, dated Nov. 26, 2008.
Notice of Allowability for Chan et al., U.S. Appl. No. 11/117,745, filed Apr. 27, 2005, dated Dec. 2, 2008.
PCT Notification of Transmittal of the International Search Report and the Written Opinion of the International Searching Authority, or the Declaration for PCT/US09/34115, filed Feb. 13, 2009 for Pacific Arrow Limited et al., dated Jun. 2, 2009.
PCT International Preliminary Report on Patentability, Mar. 12, 2009, International App'l No. PCT/US2007/077273, filed Aug. 30, 2007.
PCT Notification of Transmittal of International Preliminary Examination Report for PCT/IB02/04750, filed Aug. 28, 2002 for Fountain Silver Limited et al., dated Jun. 3, 2003.
PCT International Search Report for PCT/US2009/034115, filed Feb. 13, 2009 for Pacific Arrow Limited et al., dated Jun. 2, 2009.
Supplementary European Search Report issued on Oct. 22, 2009 for Mak et al., European Patent Application No. 05810263.3, PCT/US2005031900.
Australian Office Action for Australian Patent No. 2004281707, Feb. 19, 2010, Pacific Arrow Limited.

(56) References Cited

OTHER PUBLICATIONS

European Office Communication for Pacific Arrow Limited, et al., European App'l No. EP 06751723.5-2123, Dated Jan. 15, 2010.
European Office Communication for Mak May Sun et al., European App'l No. EP 0581026.3-2123, Dated Dec, 29, 2009.
China Office Action for Pacific Arrow Limited, et al., China App'l No. 2004800367617, Dated Jan. 15, 2010.
European Office Communication for Pacific Arrow Limited, et al., European App'l No. EP 04809909.7-2123, Dated Apr. 19, 2010.
European Office Communication for Pacific Arrow Limited, et al., European App'l No. EP 04815530.3-2123, Dated Apr. 19, 2010.
European Office Communication for Mak May Sung, et al., European App'l No. EP 05810263.3-2123, Dated Apr. 19, 2010.
European Office Communication for Pacific Arrow Limited, et al., European App'l No. EP 07841638.5-2123, Dated Apr. 19, 2010.
Chinese Office Action, Mar. 27, 2009 for Pacific Arrow Limited, Chinese application No. 2005800375247, filed Jul. 26, 2007.
Chinese Office Action, Apr. 21, 2010 for Pacific Arrow Limited, Chinese application No. 2005800375247, filed Jul. 26, 2007.
New Zealand Letters Patent No. 546138, Apr. 8, 2010, Pacific Arrow Limited, et al. "Composition Comprising *Xanthoceras sorbifolia* Extracts, Compounds Isolated From Same, Methods for Perparing Same and Uses Thereof".
Canadian Office Action for Canadian Application No. 2,451,740, May 26, 2000, Fountain Silver Limited, "Composition Comprising Wenguanoguo Extracts, Methods for Perparing Same and Uses Thereof".
PCT Preliminary Report on Patentability for PCT/US2009/034115, filed Feb. 13, 2009 for Pacific Arrow Limited et al., dated Aug. 26, 2010.
PCT Written Opinion of the International Searching Authority for PCT/US09/34115, filed Feb. 13, 2009 for Pacific Arrow Limited at al., dated Jun. 2, 2009.
PCT Written Opinion of the International Searching Authority for PCT/US10/42220, filed Jul. 16, 2010 for Pacific Arrow Limited et al., dated Sep. 2, 2010.
PCT International Search Report for PCT/US10/42240, filed Jul. 16, 2010 for Pacific Arrow Limited et al., dated Sep. 2, 2010.
Japan Final Office Action, Feb. 23, 2009, for Fountain Silver Limited et al., Japan App'l No. 2003-522442, filed Feb. 5, 2004.
Japan Office Action, Jan. 14, 2011, for Pacific Arrow Limited et al., Japan App'l No. 2006-534419, filed Mar. 22, 2006.
Japan Office Action, Feb. 2, 2011, for Pacific Arrow Limited et al., Japan app'l No. 2006-534419, filed Mar. 22, 2006.
Japan Office Action, Mar. 18, 2011, for Pacific Arrow Limited et al., Japan app'l No. 2006-547422, filed Jun. 16, 2006.
Australian Office Action, Mar. 18, 2011 for Pacific Arrow Limited et al., Australian Patent Application No. 2004281707, filed Oct. 8, 2004.
Korean Office Action, Jun. 3, 2011 for Pacific Arrow Limited et al., Korean App'l No. 10-2006-7008896, filed May 8, 2006.
New Zealand Office Action, Mar. 7, 2011 for Pacific Arrow Limited et al., New Zealand App'l No. 587973, filed Sep. 14, 2010.
Notice of Acceptance for Pacific Arrow Limited et al., Australian Patent App'l No. 2004281707, filed Mar. 23, 2006, Dated May 26, 2011.
New Zealand Office Action, Apr. 12, 2011 for Pacific Arrow Limited et al., New Zealand App'l No. 554037, filed Mar. 19, 2007.
Japan Office Action, Jun. 3, 2011 for Pacific Arrow Limited et al., Japan App'l No. 2006-534419, filed Mar. 22, 2006.
Voutquenne et al. "Structure—Activity Relationships of Haemolytic Saponins" Pharmaceutical Biology (2002), vol. 40, No. 4, pp. 253-262.
Siroti, C., "Aescin: Pharmacology, Pharmacokinetic Profile" Pharmacological Research(2001) vol. 44, No. 3, pp. 183-193.
Oda, K. et al., "Adjuvant and Haemolytic Activities of 47 Saponins Derived from Medicinal and Food Plants" Biol. Chem. (2000) vol. 381, pp. 67-74.

Ushijima et al, 2008, "Triterpene Glycosides from the Roots of *Codonopsis lanceolata*", Chemical & Pharmaceutical Bulletin, vol. 56(3) 308-314.
Yadava et al., 2008, "New antibacterial triterpenoid saponin from *Lactuca scariola*", Fitoterapia, vol. 1:1-5.
Wang et al., 2008, "Bioactive Triterpene Saponins from the Roots of *Phytolacca Americana*", Journal of Natural Products, vol. 71(1): 35-40.
Chang et al, 2007, "Biologically Active Triterpenoid Saponins from *Ardisia japonica*", Journal of Natural Products, vol. 70(2): 179-187.
Akihisa et al, 2006, "Cancer Chemopreventive Effects and Cytotoxic Activities of the Triterpene Acids from the Resin of *Boswellia carteri*", Biological & Pharmaceutical Bulletin, vol. 29(9):1976-1979.
Liang, et al., 2006, "Triterpenoid Saponins from *Lysimachia davurica*", Chemical & Pharmaceutical Bulletin, vol. 54 (10):1380-1383.
Fujioka, et al., 2006, "Antiproliferative Constituents from Umbelliferae Plants. New Triterpenoid Glycosides from the Fruits of *Bupleurum rotundifolium*", Chemical & Pharmaceutical Bulletin, vol. 54 (12):1694-1704.
Rabi, et al., 2007; "Novel triterpenoid 25-hydroxy-3-oxoolean-12-en-28-oic acid induces growth arrest and apoptosis in breast cancer cells", Breast Cancer Research & Treatment, vol. 101:27-36.
Sporn, et al., 2007, "Platforms and Networks in Triterpenoid Pharmacology", Drug Development Research, vol. 68:174-182 (2007).
Puiffe, et al., 2007, "Characterization of Ovarian Cancer Ascites on Cell Invasion, Proliferation, Spheroid Formation, and Gene Expression in an In Vitro Model of Epithelial Ovarian Cancer" Neoplasia, vol. 9(10):820-829.
Ricciardelli, et al., 2006, "Extracellular Matrix of Ovarian Tumors", Seminars in Reproductive Medicine, vol. 24(4): 270-282.
Bang. et al., 2007. "Facile Synthesis of Trisaccharide Moiety Corresponding to Antitumor Activity in Triterpenoid Saponins Isolated from Pullsatilla Roots", Chemical & Pharmaceutical Bulletin, vol. 55(12): 1734-1739.
Talmadge, James E., 2008, "Follistatin as an Inhibitor of Experimental Metastasis", Clinical Cancer Research, vol. 14(3) 624-626.
Wei, et al., 2004, "Anti-inflammatory Triterpenoid Saponins from the Seeds of *Aesculus chinensis*", Chemical & Pharmaceutical Bulletin, vol. 52(10): 1246-1248.
Zhu et al, "Preliminary test of chemical constituents of wenguanguo and its multipurpose utilization", Research of Land and Natural Resources (1): 69-71, 1997 Arda, et al. "Saniculoside N from *Sanicula europaea* L." Journal of Natural Products (1997), 60(11), 1170-1173.
Maes, et al. "In vitro and in vivo activities of a triterpenoid saponin extract (px-6518) from the plant *Maesa balansae* against visceral leishmania species." Antimicrobial agents and chemotherapy, Jan. 2004, p. 130-136.
Murakami, et al. "New hypoglycemic constituents in "gymnemic acid" from gymnema sylvestre." Chem, Pharm. Bull. 44(2) 469-471 (1996 ).
Na, et al. "Protein tyroshine phosphatase 1B inhibitory activity of triterpenes isolated from *Astilbe koreana*." Bioorg Med Chem Lett. Jun. 15, 2006:16(12): 3273-6.
Zhou, et al. "The first naturally occurring tie2 kinase inhibitor." Org Lett. Dec. 13, 2001;3(25): 4047-9.
2006 Chemical Abstracts Catalog, published 2006 by Chemical Abstracts Service, p. 52.
Apers Sandra et al., "Antiviral, haemolytic and moliuscicidal activities of triterpenoid saponins. from *Maesa lanceolata*: Establishment of structure-activity relationships", Planta Medica, vol. 67, No. 6, Aug. 2001, pp. 528-532.
Ahmad V U et al., "The Sapogenins from *Dodonaea viscosa*", Fitoterapia, vol. 58, No. 5, 1987, pp. 361-362.
Dizes C et al., "Harpuloside a triterpenoid saponin from *Harpullia ramiflora*", Phytochemistry, Pergamon Press, GB, vol. 48, No. 7, Aug. 1, 1998, pp. 1229-1232.
Cheng, et al. "Two new sterols in the husk of *Xanthoceras sorbifolia*." Chinese Traditional and Herbal Drugs (2001), 32(3), 199-201.

(56) References Cited

OTHER PUBLICATIONS

"Cancer". Wikipedia, The Free Encyclopedia. Wikimedia Foundation, Inc. Jul. 22, 2004. Web Aug. 11, 2011.
US Office Action, May 12, 2011, for Chan et al., U.S. Appl. No. 12/714,598, filed Mar. 1, 2010.
U.S. Office Action, Dec. 21, 2011, for Chan et al., U.S. Appl. No. 12/541,713, filed Aug. 14, 2009.
Chinese Office Action, Jun. 3, 2011 for Pacific Arrow Limited, Chinese application No. 200880012065.0, filed Oct. 14, 2009.
Chinese Office Action, Jun. 14, 2011, for Pacific Arrow Limited, Chinese App'l No. 200480036761.7, filed Jun. 8, 2006.
Chinese Office Action, Oct. 28, 2011, for Pacific Arrow Limited, Chinese App'l No. 200480038698.0, filed Jun. 23, 2006.
Chinese Office Action, Sep. 28, 2011, for Pacific Arrow Limited, Chinese App'l No. 200480036761.7, filed Jun. 8, 2006.
Chinese Office Action, Mar. 23, 2011, for Pacific Arrow Limited, Chinese App'l No. 200780040744.4, filed Apr. 30, 2009.
Chinese Notice of Allowance, Feb. 1, 2011, for Pacific Arrow Limited, Chinese app'l No. 200580037524.7, filed Apr. 30, 2007.
Canadian Office Action, Sep. 8, 2011, for Fountain Silver Limited et al., Canadian App'l No. 2,451,740, filed Dec. 18, 2003.
Canadian Notice of Allowance, Oct. 5, 2011, for Pacific Arrow Limited et al, Canadian App'l No. 2,541,425, filed Oct. 8, 2004.
Canadian Office Action, Jan. 31, 2012, for Pacific Arrow Limited, Canadian Application No. 2,579,231, filed Mar. 6, 2007.
Taiwan Office Action, Mar. 12, 2010 for Pacific Arrow Limited, Taiwan App'l No. 093140030, filed Dec. 22, 2004.
Taiwan Office Action, Mar. 3, 2011 for Pacific Arrow Limited, Taiwan App'l No. 093140030, filed Dec. 22, 2004.
Taiwan Office Action, Jan. 18, 2012 for Pacific Arrow Limited, Taiwan App'l No. 094130519, filed Sep. 6, 2005.
Japanese Notice of Allowance, Nov. 15, 2011, for Pacific Arrow Limited, Japanese app'l No. 2006-547422, filed Jun. 16, 2006.
Japanese Office Action, Nov. 21, 2011, for Pacific Arrow Limited, Japanese app'l No. 2007-530484, filed Mar. 2, 2007.
New Zealand Office Action, Sep. 24, 2010, for Pacific Arrow Limited, New Zealand App'l No. 579194, filed Aug. 21, 2009.
New Zealand Office Action, Jan. 11, 2012, for Pacific Arrow Limited, New Zealand App'l No. 579194, filed Aug. 21, 2009.
European Office Communication, Feb. 13, 2012, for Pacific Arrow Limited, European App'l No. EP 07841638.5-2123, filed Mar. 27, 2009.
European Office Communication, Feb. 13, 2012 for Pacific Arrow Limited, European App'l No. EP 05810263.3-2123, filed Mar. 30, 2007.
European Office Communication, Feb. 13, 2012 for Pacific Arrow Limited, European App'l No. EP 04815530.3-2123, filed Jul. 19, 2006.
Australian Office Action, Feb. 6, 2012 for Pacific Arrow Limited, Australian App'l No. 2009208069, filed Aug. 7, 2009.
Australian Office Action, Feb. 6, 2012 for Pacific Arrow Limited, Australian App'l No. 2005282437, filed Mar. 19, 2007.
PCT Written Opinion of the International Searching Authority, Dec. 6, 2011, for Pacific Arrow Limited, Int'l App'l No. PCT/US2011/044233, filed Jul. 15, 2011.
PCT International Search Report Dec. 6, 2011, for Pacific Arrow Limited, Int'l App'l No. PCT/US2011/044233, filed Jul. 15, 2011.
U.S. Office Action, Dec. 28, 2011, for Chan et al., U.S. Appl. No. 12/714,598, filed Mar. 1, 2010.
U.S. Notice of Allowance, Jan. 30, 2012, for Chan et al., U.S. Appl. No. 11/683,198, filed Mar. 7, 2007.
U.S. Office Action, Apr. 17, 2012, for Chan et al., U.S. Appl. No. 12/392,795, filed Feb. 25, 2009.
Australian Office Action, Feb. 6, 2012 for Pacific Arrow Limited, Australian App'l No. 2009200988, filed Mar. 10, 2009.
European Office Communication, Mar. 5, 2012 for Pacific Arrow Limited, European App'l No. EP 04809909.7-2123, filed Mar. 27, 2006.
European Office Communication, Apr. 26, 2012 for Pacific Arrow Limited, European App'l No. EP 09721583.4-2123, filed Sep. 7, 2010.
New Zealand Office Action, Mar. 26, 2012, for Pacific Arrow Limited, New Zealand App'l No. 598934, filed Mar. 21, 2012.
Chinese Office Action, Apr. 9, 2012, for Pacific Arrow Limited, Chinese App'l No. 200780040744.4, filed Apr. 30, 2009.
European Office Communication, Jun. 4, 2012 for Pacific Arrow Limited, European App'l No. EP 02781502.6-2112, filed Feb. 25, 2004.
Yang et al. "The Influence of aquaporin-1 and microvessel density on ovarian carcinogenesis and ascites formation", International Journal of Gynecological Cancer, vol. 16, No. S1, Feb. 1, 2006, pp. 400-405.
Germonprez N. et al. "In vitro and in vivo anti-leishmanial activity of triterpenoid saponins isolated from *Maesa balansae* and some chemical derivatives", Journal of Medicinal Chemistry, vol. 48 No. 1 (Jan. 13, 2005), p. 32-37.
Chemical Abstracts Service, Columbus, Ohio, US, Germonprez N. et al., "Antileishmanial saponins from *Maesa*", Tap Chi Hoa Hoc, 41(spec.), 125-130, (2003).
U.S. Office Action, Jun. 26, 2012, for Chan et al., U.S. Appl. No. 12/541,713, filed Aug. 14, 2009.
Japanese Office Action, May 8, 2012, for Pacific Arrow Limited, Japanese app'l No. 2007-530484, filed Mar. 2, 2007.
Australian Office Action, Jun. 21, 2012 for Pacific Arrow Limited, Australian App'l No. 2008244648, filed Aug. 21, 2009.
Korean Office Action, Jun. 22, 2012 for Pacific Arrow Limited, Korean App'l No. 10-2007-7007902, filed Apr. 6, 2007 (w/English Translation).
Canadian Office Action, Jul. 5, 2012, for Fountain Silver Limited et al., Canadian App'l No. 2,451,740, filed Dec. 18, 2003.
Notice of Allowability, Aug. 15, 2012, for Chan et al., U.S. Appl. No. 12/392,795, filed Feb. 25, 2009.
Notice of Allowability for Chan et al., U.S. Appl. No. 12/541,713, filed Aug. 14, 2009, Dated Sep. 12, 2012.
PCT Written Opinion of the International Searching Authority, Oct. 2, 2012, for Pacific Arrow Limited, Int'l App'l No. PCT/US12/46716, filed Jul. 13, 2012.
PCT International Search Report, Oct. 2, 2012, for Pacific Arrow Limited, Int'l App'l No. PCT/US12/46716, filed Jul. 13, 2012.
U.S. Office Action, Oct. 15, 2012, for Chan et al., U.S. Appl. No. 13/259,480, filed Sep. 23, 2011.
U.S. Office Action, Mar. 21, 2013, for Chan et al., U.S. Appl. No. 12/856,322, filed Aug. 13, 2010.
U.S. Office Action, Feb. 1, 2013, for Chan et al., U.S. Appl. No. 13/259,480, filed Sep. 23, 2011.
U.S. Office Action, Apr. 11, 2013, for Chan et al., U.S. Appl. No. 11/683,198, filed Mar. 7, 2007.
U.S. Office Action, Jun. 6, 2013, for Chan et al., U.S. Appl. No. 13/259,480, filed Sep. 23, 2011.
PCT International Preliminary Report on Patentability, Jun. 25, 2013, for Pacific Arrow Limited, Int'l App'l No. PCT/US2011/044233, filed Jul. 15, 2011.
PCT Notification Concerning Transmittal of International Preliminary Report on Patentability, Jul. 4, 2013, for Pacific Arrow Limited, Int'l App'l No. PCT/US2011/044233, filed Jul. 15, 2011.
Notice of Allowability for Chan et al., U.S. Appl. No. 14/020,099, filed Sep. 6, 2013, Dated Mar. 3, 2014.
U.S. Office Action, Nov. 21, 2013, for Chan et al., U.S. Appl. No. 13/718,575, filed Dec. 18, 2012.
Canadian Office Action, May 21, 2013, for Fountain Silver Limited et al., Canadian App'l No. 2,451,740, filed Dec. 18, 2003.
Canadian Office Action, Feb. 26, 2013, for Pacific Arrow Limited, Canadian App'l No. 2,579,231, filed Mar. 6, 2007.
European Office Communication, May 13, 2013 for Pacific Arrow Limited, European App'l No. EP 10800596.8-1462, filed Mar. 30, 2012.

(56) References Cited

OTHER PUBLICATIONS

European Office Communication, Jun. 26, 2013, for Pacific Arrow Limited, European App'l No. EP 04815530.3-1464, filed Jul. 19, 2006.
Australian Office Action, Apr. 16, 2013 for Pacific Arrow Limited, Australian App'l No. 2009226063, filed Sep. 6, 2010.
Dan Peer, et al. "Nanocarriers as an emerging platform for cancer therapy." Nature Publishing Group (2007), 751-760.
Mahato et al. Tetrahedron 1991 (47) 5215-5230.
Sheng-Xiang et al. Phytochemistry (1993), 34(5), 1385-1387.
Ohtsuki et al. "Acylated triterpenoid saponins from *Schima noronhae* and their cell growth inhibitory activity", Journal of Natural Products, vol. 71, No. 5, Mar. 20, 2008, pp. 918-921, XP002694762.
Sharma et al. "Lanthadenes and their esters as potential antitumor agents", Journal of Natural Products, vol. 71, No. 7, Jun. 14, 2008, pp. 1222-1227, XP002694763.
Declaration of Interference #105,982, Dec. 9, 2013, *Pui-Kwong Chan, May Sung Mak and Yun Wang (Junior Party)* v. *Baizhen Yang, Songjiang Wang and Congfu Zhao (Senior Party)*.

* cited by examiner

Structure of saponin

Structure of saponin

Structure of saponin

Structure of saponin

Structure of saponin

Structure of saponin

R1 = acetyl group or H
R2 = angeloyl
R3 = angeloyl
R6 = H
R4, R7 = CH3 or CH2OH or COOH Y1 and Y2 activity on Ovarian caner cells Anticancer activity of Compounds Y, Y8, Y9 and Y10.

Haemolytic and Mtt activities of Compound Y

Structures of Y, X, ACH-Y and AKOH-Y

COMPOSITION COMPRISING TRITERPENE SAPONINS AND COMPOUNDS WITH ANGELOYL FUNCTIONAL GROUP, METHODS FOR PREPARING SAME AND USES THEREOF

This application is a continuation of U.S. Ser. No. 11/289,142, filed Nov. 28, 2005 now U.S. Pat. No. 7,488,753, which is a Continuation-in-part of U.S. Ser. No. 11/267,523, filed Nov. 4, 2005 now abandoned, Continuation-In-Part of International Application No. PCT/US2005/031900, filed Sep. 7, 2005, Continuation-In-Part of U.S. Ser. No. 11/131,551, filed May 17, 2005 now U.S. Pat. No. 7,262,285, Continuation-In-Part of U.S. Ser. No. 11/117,760, filed Apr. 27, 2005 now U.S. Pat. No. 7,727,561, Continuation-In-Part application of U.S. Ser. No. 10/906,303, filed Feb. 14, 2005 now U.S. Pat. No. 7,524,824, Continuation-In-Part of International Application No. PCT/US04/43465, filed Dec. 23, 2004, which is a Continuation-In-Part application of Int'l App'l No. PCT/US04/33359, filed Oct. 8, 2004, which claims the benefit of U.S. Ser. No. 60/532,101, filed Dec. 23, 2003, and 60/509,851, filed Oct. 9, 2003; and International Application No. PCT/US05/31900, filed Sep. 7, 2005, claims the benefit of U.S. Ser. No. 60/617,379, filed Oct. 8, 2004, 60/613,811, filed Sep. 27, 2004, and 60/607,858, filed Sep. 7, 2004, 60/675,282, Filed Apr. 27, 2005, and 60/675,284, Filed Apr. 27, 2005. The contents of these preceding applications are hereby incorporated in their entireties by reference into this application.

Throughout this application, various publications are referenced. Disclosures of these publications in their entireties are hereby incorporated by reference into this application in order to more fully describe the state of the art to which this invention pertains.

FIELD OF THE INVENTION

This invention relates to saponins, and compounds with angeloyl groups isolated from plants, their uses and functions, and methods of their preparations.

SUMMARY OF THE INVENTION

In accordance with these and other objects of the invention, a brief summary of the present invention is presented. Some simplifications and omission may be made in the following summary, which is intended to highlight and introduce some aspects of the present invention, but not to limit its scope. Detailed descriptions of a preferred exemplary embodiment adequate to allow those of ordinary skill in the art to make and use the invention concepts will follow in later sections.

This invention provides a compound comprising a triterpenoidal saponin, triterpenoid, triterpenoidal compound or sapongenin, comprising two angeloyl groups, or at least two side groups selected from the group consisting of: angeloyl groups, tigloyl groups and senecioyl groups, wherein the side groups are attached to carbon 21, 22 or/and 28 of triterpenoidal saponin, triterpenoid, triterpenoidal compound or sapongenin backbone.

This invention provides a composition for inhibiting tumor cell growth, comprising an appropriate amount of a triterpenoidal saponin, triterpenoid, triterpenoidal compound or sapongenin, wherein the triterpenoidal saponin, triterpenoid, triterpenoidal compound or sapongenin comprises two angeloyl groups or any two side groups selected from the group consisting of: angeloyl groups, tigloyl groups and senecioyl groups, wherein the side groups are attached to carbon 21 and 22 of triterpenoidal saponin, triterpenoid, triterpenoidal compound or sapongenin backbone. In an embodiment, the side groups are attached to carbon 21, 22 or/and 28 of triterpenoidal saponin, triterpenoid, triterpenoidal compound or sapongenin backbone.

This invention provides a composition for inhibiting tumor cell growth, comprising an appropriate amount of a triterpenoidal saponin, triterpenoid, triterpenoidal compound or sapongenin, wherein the triterpenoidal saponin, triterpenoid, triterpenoidal compound or sapongenin comprises two angeloyl groups or any two side groups selected from the group consisting of: angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl, wherein the side groups are attached to carbon 21 and 22 of triterpenoidal saponin, triterpenoid, triterpenoidal compound or sapongenin backbone. In an embodiment, the side groups are attached to carbon 21, 22 or/and 28 of triterpenoidal saponin, triterpenoid, triterpenoidal compound or sapongenin backbone.

The invention provides the methods and uses of triterpenoidal saponins purified and isolated from plants.

This invention provides compositions comprising the triterpenoidal saponins or their derivatives for inhibition of tumor growth. The compounds comprise angeloyl group(s) or tigloyl group(s) or senecioyl group(s) or combinations thereof which are attached to carbon 21, 22 or/and 28 of their sapongenines. In an embodiment, the compounds may comprise any two angeloyl groups or tigeloyl groups or senecioyl groups or combinations thereof attached to a sugar moiety which bonds to carbon 21 or 22 of their sapongenines. In an embodiment, the side groups are attached to carbon 21, 22 or/and 28 of triterpenoidal saponin, triterpenoid, triterpenoidal compound or sapongenin backbone.

This invention provides compositions comprising the triterpenoidal saponins or their derivatives for inhibition of tumor growth. The compounds comprise angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or combinations thereof which are attached to carbon 21, 22 or/and 28 of their sapongenines. In an embodiment, the compounds may comprise any two angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or combinations thereof attached to a sugar moiety which bonds to carbon 21 or 22 of their sapongenines. In an embodiment, the side groups are attached to carbon 21, 22 or/and 28 of triterpenoidal saponin, triterpenoid, triterpenoidal compound or sapongenin backbone.

In an embodiment, the saponin comprises a sugar moiety, wherein the sugar moiety comprises at least one sugar, or D-glucose, or D-galactose, or L-rhamnose, or L-arabinose, or D-xylose, or alduronic acid, or D-glucuronic acid or D-galacturonic acid, or their derivative thereof, or the combination thereof.

DETAILED DESCRIPTION OF THE FIGURES

FIG. 1 shows structure of saponins.
FIG. 2 shows structure of saponins.
FIG. 3 shows structure of saponins
R5=B or C or S1 (see note 1)
R1=A or B or C
R2=A or B or C
R4=A or B or C Note 1:
A=angeloyl or Tigloyl or Senecioyl
B=acetyl
C=H
S1=sugar moiety comprising one or more sugar, D-glucose, D-galactose, L-rhamnose, L-arabinose, D-xylose, alduronic acid, D-glucuronic acid, D-galacturonic acid, or their derivatives.
Positions 23-27, 29-30 are attached with CH3 or CH2OH or COOH or acetyl group FIG. 4 shows structure of saponins
FIG. 5 shows a structure of saponins
R5=B or C or S1 (see note 1)
R1=A or B or C
R2=A or B or C
R3=A or B or C
R4=A or B or C
Note 1:
A=angeloyl or Tigloyl or Senecioyl
B=acetyl
C=H
S1=sugar moiety comprising one or more sugar, D-glucose, D-galactose, L-rhamnose, L-arabinose, D-xylose, alduronic acid, D-glucuronic acid, D-galacturonic acid, or their derivatives.
positions 23-27, 29-30 are attached with CH3 or CH2OH or COOH or acetyl group FIG. 6 shows a structure of saponins
R5=B or C or S1 (see note 1)
R1=A or B or C
R2=A or B or C
R3=A or B or C
R4=A or B or C
Note 1:
A=angeloyl or Tigloyl or Senecioyl
B=acetyl
C=H
S1=sugar moiety comprising one or more sugar, D-glucose, D-galactose, L-rhamnose, L-arabinose, D-xylose, alduronic acid, D-glucuronic acid, D-galacturonic acid, or their derivatives.
positions 23-27, 28-30 are attached with CH3 or CH2OH or COOH or acetyl group FIG. 7. A shows a structure of saponins
Wherein R1=angeloyl group or tigloyl group or senecioyl group or H.
R2=angeloyl group or tigloyl group or senecioyl group or acetyl group or H.
R3=angeloyl group or tigloyl group or senecioyl group or acetyl group or H.

FIG. 7 B, C, D shows a structure of saponins
Wherein R1=angeloyl group or tigloyl group or senecioyl group or H.
R2=angeloyl group or tigloyl group or senecioyl group or acetyl group or H.
R3=angeloyl group or tigloyl group or senecioyl group or acetyl group or H.
R6=H or OH
Position 23-27 and 28-30 are attached with CH3 or CH2OH or COOH or CHO FIG. 8 shows a structure of saponins:
Wherein R1=angeloyl group or tigloyl group or senecioyl group or H.
R2=angeloyl group or tigloyl group or senecioyl group or acetyl group or H.
R3=angeloyl group or tigloyl group or senecioyl group or acetyl group or H.
R4=OH or H FIG. 9 A shows a structure of saponins:
Wherein R1=angeloyl group or tigloyl group or senecioyl group or acetyl group or H.
R2=angeloyl group or tigloyl group or senecioyl group or acetyl group or H.
R3=Acetyl or H.
R8=H or OH FIG. 9 B shows a structure of saponins:
Wherein R1=angeloyl group or tigloyl group or senecioyl group or acetyl group or H.
R2=angeloyl group or tigloyl group or senecioyl group or acetyl group or H.
R3=Acetyl or H.
R4=CH3 or CH2OH or COOH
R6=CH3 or CH2OH or COOH
R8=H or OH FIG. 10 shows a structure of saponins:
Wherein R1=angeloyl group or tigloyl group or senecioyl group or acetyl group or H.
R2=angeloyl group or tigloyl group or senecioyl group or acetyl group or H.
R3=Acetyl or H.
R4=COOH OR COOMe or $CH_2OH$
R5=$\alpha$-L-araf and R6=$\alpha$-L-arap and R7=$\beta$-D-glup; or R5, R6, and R7 is a sugar moiety, or D-glucose, or D-galactose, or L-rhamnose, or L-arabinose, or D-xylose, or alduronic acid, or D-glucuronic acid, or D-galacturonic acid, or their derivatives.

FIG. 11 A shows a structure of saponins:
Wherein R1=angeloyl group or tigloyl group or senecioyl group or acetyl group or H.
R2=angeloyl group or tigloyl group or senecioyl group or acetyl group or H.
R3=$CH_2OH$ or $CH_3$ or CHO FIG. 11 B shows a structure of saponins:
Wherein R1=angeloyl group or tigloyl group or senecioyl group or acetyl group or H.
R2=angeloyl group or tigloyl group or senecioyl group or acetyl group or H.
R3=$CH_2OH$ or $CH_3$ or CHO FIG. 12 A shows a structure of saponins:
Wherein R1=angeloyl group or tigloyl group or senecioyl group or acetyl group or H.
R2=angeloyl group or tigloyl group or senecioyl group or acetyl group or H.
R3=$CH_2OH$ or $CH_3$ or CHO or $COOCH_3$
R4=S1=sugar moiety comprising one or more sugar, D-glucose, D-galactose, L-rhamnose, L-arabinose, D-xylose, alduronic-acid, D-glucuronic acid, D-galacturonic acid, or/and their derivatives.

FIG. 12 B shows a structure of saponins:
Wherein R1=angeloyl group or tigloyl group or senecioyl group or acetyl group or H.
R2=angeloyl group or tigloyl group or senecioyl group or acetyl group or H.
R3=$CH_2OH$ or $CH_3$ or CHO or $COOCH_3$
R4=sugar moiety comprising one or more sugar, D-glucose, D-galactose, L-rhamnose, L-arabinose, D-xylose, alduronic acid, D-glucuronic acid, D-galacturonic acid, or/and their derivatives.

FIG. 13 shows a structure of saponins:
Wherein R2=angeloyl group or tigloyl group or senecioyl group or acetyl group or H.

R3=angeloyl group or tigloyl group or senecioyl group or acetyl group or H.
R4=CH₂OH or CH₃ or CHO or COOCH₃
R1=sugar moiety comprising one or more sugar, D-glucose, D-galactose, L-rhamnose, L-arabinose, D-xylose, alduronic acid, D-glucuronic acid, D-galacturonic acid, or/and their derivatives.

FIG. 14 shows a structure of saponins:

Wherein R1=angeloyl group or tigloyl group or senecioyl group or propanoyl or butanoly or acetyl group or H.
R2=angeloyl group or tigloyl group or senecioyl group or propanoyl or butanoly or acetyl group or H.
R3=angeloyl group or tigloyl group or senecioyl group or propanoyl or butanoly or acetyl group or H.
R4=sugar moiety comprising one or more sugar, D-glucose, D-galactose, L-rhamnose, L-arabinose, D-xylose, alduronic acid, D-glucuronic acid, D-galacturonic acid, or/and their derivatives.

FIG. 15 shows a structure of saponins
FIG. 16 A, 16 B shows a structure of saponins
R1=angeloyl or Tigloyl or Senecioyl or acetyl or H
R2=angeloyl or Tigloyl or Senecioyl or acetyl or H
R6=angeloyl or Tigloyl or Senecioyl or acetyl or H
R3=H or OH
R10=CH3 or CH2OH or CHO
R5=D-glucose or D-galactose or L-rhamnose or L-arabinose or, D-xylose or alduronic acid or D-glucuronic acid or D-galacturonic acid or H
R7=D-glucose or D-galactose or L-rhamnose or L-arabinose or, D-xylose or alduronic acid or D-glucuronic acid or D-galacturonic acid or H
R8=D-glucose or D-galactose or L-rhamnose or L-arabinose or, D-xylose or alduronic acid or D-glucuronic acid or D-galacturonic acid or H
R9=COOH or CH2OH FIG. 17 shows a structure of saponins
FIG. 18 shows a structure of saponins
FIG. 19 shows a structure of saponins
FIG. 20 shows a structure of saponins
FIG. 21 shows a structure of saponins
R1=angeloyl or tigloyl or senecioly or acetyl group or H
R2=angeloyl or tigloyl or senecioly or acetyl group or H
R3=angeloyl or tigloyl or senecioly or acetyl group or H
R6=H
R4=CH3 or CH2OH or COOH
Position 23-27, 29, 30 are attached a CH3 or CH2OH or COOH or acetyl group
Positions 28=CH3 or CH2OH or COOH or acetyl group or angeloyl or tigloyl or senecioly or sugar chains FIG. 22 shows a structure of saponins
R1=angeloyl or tigloyl or senecioly or acetyl group or H
R2=angeloyl or tigloyl or senecioly or acetyl group or H
R3=angeloyl or tigloyl or senecioly or acetyl group or H
R6=angeloyl or tigloyl or senecioly or acetyl group or H
R4=CH3 or CH2OH or COOH
R5=acetyl or H or S1 (see note 1)
Note 1: S1=sugar moiety one or more sugar, D-glucose, D-galactose, L-rhamnose, L-arabinose, D-xylose, alduronic acid, D-glucuronic acid, D-galacturonic acid or/and their derivatives.
Positions 23-27, 29, 30 are attached a CH3 or CH2OH or COOH or acetyl group.
Position 28=CH3 or CH2OH or COOH or acetyl group or angeloyl or tigloyl or senecioly or sugar chains FIG. 23 shows a structure of saponins
R1=angeloyl or tigloyl or senecioly or acetyl group or H
R2=angeloyl or tigloyl or senecioly or acetyl group or H
R3=angeloyl or tigloyl or senecioly or acetyl group or H
R6=angeloyl or tigloyl or senecioly or acetyl group or H
R4=CH3 or CH2OH or COOH
R5=acetyl or H or S1 (see note 1)
Note 1:
S1=sugar moiety comprises one or more sugar, D-glucose, D-galactose, L-rhamnose, L-arabinose, D-xylose, alduronic acid, D-glucuronic acid, D-galacturonic acid, or/and their derivatives.
Positions 23-27, 29, 30 are attached a CH3 or CH2OH or COOH or acetyl group
Position 28=CH3 or CH2OH or COOH or acetyl group or angeloyl or tigloyl or senecioly or sugar chains FIG. 24 shows a structure of saponins
R2, R3, R5, R6, R8, R9=angeloyl or tigloyl or senecioly or acetyl or H
R4=CH3 or CH2OH or COOH
S1=Sugar moiety comprises one or more sugar, D-glucose, D-galactose, L-rhamnose, L-arabinose, D-xylose, alduronic acid, D-glucuronic acid, D-galacturonic acid, or/and their derivatives.
Positions 23-27, 29, 30 are attached a CH3 or CH2OH or COOH or acetyl group
Position 28=CH3 or CH2OH or COOH or acetyl group or angeloyl or tigloyl or senecioly or sugar chains or sugar chain with angeloyl group FIG. 25 shows a structure of saponins
R2, R3, R5, R6, R8, R9=angeloyl or tigloyl or senecioly or acetyl or H
R4, R7=CH3 or CH2OH or COOH
Positions 23-27, 29, 30 are attached a CH3 or CH2OH or COOH
Position 28=CH3 or CH2OH or COOH or acetyl group or angeloyl or tigloyl or senecioly or sugar chains or sugar chain with angeloyl group.

FIG. 26 shows a structure of compounds with angeloyl groups
For structure A, B, C, D, E, F, G and H where R1, R2=angeloyl or tigloyl or senecioly FIG. 27 shows a structure of saponins
FIGS. 28 A and B shows the comparison of potency of Compound Y (saponin with 2 angeloyl groups) and compound X (saponin with 1 angeloyl) in ovarian cancer cells. The IC50 for Compound Y in ovary cells is about 1.5 ug/ml while the IC50 for compound X is 30 ug/ml.

FIG. 28 C shows the inhibition of the purified Compound Y on the growth of skin cancer cell. The IC50 is 0.23 ug/ml.

Figure 33:
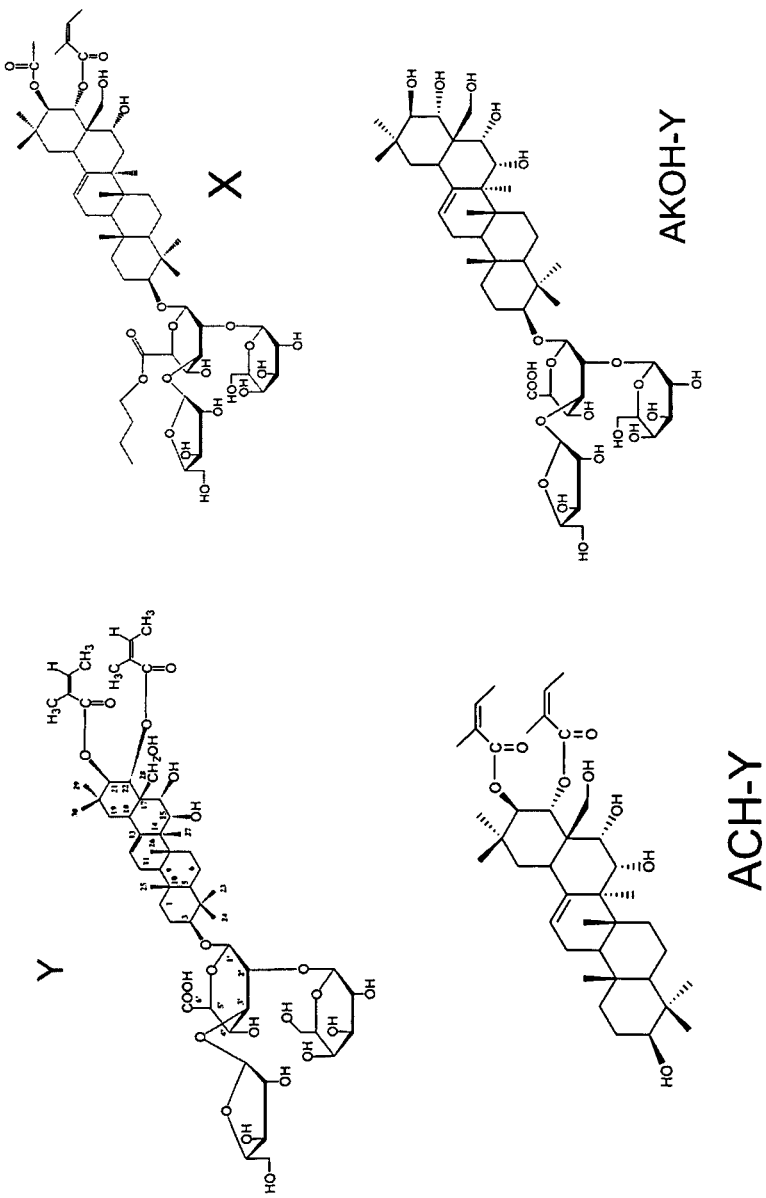

FIG. 33 shows the saponin compounds Y, X ACH—Y, AKOH—Y of the invention. These compounds are purified and their structures were verified by NMR and MS. These compounds are then used for cell growth inhibition studies (MTT).

Figure 34:
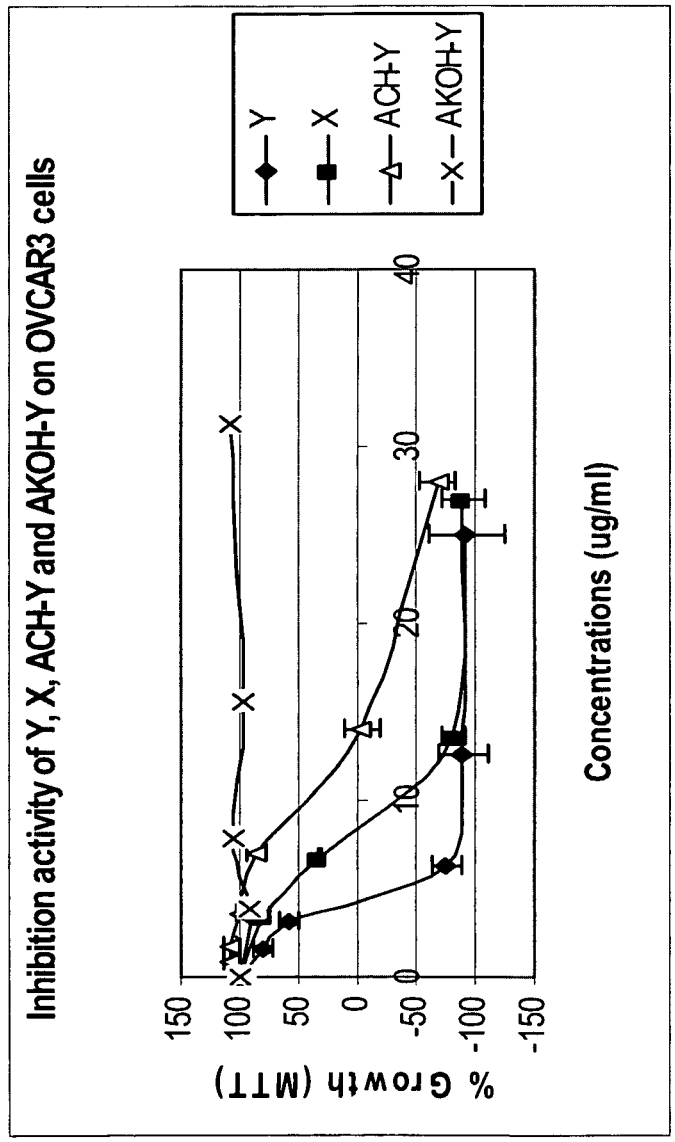

FIG. 34 The experiment results show that Y inhibits tumor growth (with IC50=4 ug/ml). Compound X which has a similar structure to Y but with only one angeloyl group at C22, has less activity (IC50=6 ug/ml) than Y. Removal of sugars from Y (ACH—Y) but retaining the diangeloyl group retains 40% of activity (IC50=9.5 ug/ml). However, removal of both angeloyl groups from C21 and C22 of Y (AKOH—Y) completely abolishes its activity (no activity even at 120 ug/ml). Results indicate that diangeloyl groups in compound Ys are important for anti-tumor activity.

DETAILED DESCRIPTION OF THE INVENTION

This invention describes the results of a program of screening the bioactive compounds from natural plants. Most of the plants are in Sapindaceae family, which has 1400-2000 species with 140-150 genera. The program of screening for bioactive compounds is based on our purification methods and biological assays including the MTT assay.

The invention provides methods and uses of saponins including triterpenoidal saponins purified or isolated from plants in the following genus:

*Acer, Aesculus, Alectryon, Allophylus, Allosanthus, Amesiodendron, Aphania, Aporrhiza, Arfeuillea, Arytera, Atalaya, Athyana, Averrhoidium, Blighia, Boniodendron, Camellia, Camptolepis, Cardiospermum, Castanospora, Chonopetalum, Chouxia, Chytranthus, Conchopetalum, Cossinia, Cubilia, Cupania, Cupaniopsis, Deinbollia, Delavaya, Diatenopteryx, Dictyoneura, Dilodendron, Dimocarpus, Diploglottis, Diplokelepa, Diplopeltis, Dipteronia, Distichostemon, Dodonaea, Doratoxylon; Elattostachys, Eriocoelum, Erioglossum, Erythrophysa, Euchorium, Euphorianthus, Eurycorymbus, Exothea, Filicium, Ganophyllum, Glenniea, Gloeocarpus, Gongrodiscus, Gongrospermum, Guindilia, Guioa, Handeliodendron, Haplocoelum, Harpullia, Hippobromus, Hornea, Houssayanthus, Hypelate, Hypseloderma, Jagera, Koelreuteria, Laccodiscus, Lecaniodiscus, Lepiderema, Lepidopetalum, Lepisanthes, Litchi, Llagunoa, Lophostigma, Loxodiscus, Lychnodiscus, Macphersonia, Maesa, Magonia, Majidea, Matayba, Melicoccus, Mischocarpus, Molinaea, Negundo, Neotina, Nephelium, Otonephelium, Otophora, Pappea, Paranephelium, Paullinia, Pavieasia, Pentascyphus, Phyllotrichum, Pittosporum, Placodiscus, Plagioscyphus, Podonephelium, Pometia, Porocystis, Pseudima, Pseudopancovia, Pseudopteris, Ptelea, Radlkofera, Rhysotoechia, Sapindus, Sarcopteryx, Sarcotoechia, Scyphonychium, Serjania, Sisyrolepis, Smelophyllum, Stadmania, Stocksia, Storthocalyx, Synima, Talisia, Thinouia, Thouinia, Thouinidium, Tina, Tinopsis, Toechima, Toulicia, Trigonachras, Tripterodendron, Tristira, Tristiropsis, Tsingya, Ungnadia, Urvillea, Vouarana, Xanthoceras, Xeropspermum, Zanha, Zollingeria.*

Saponins including triterpenoidal saponins may also be purified or isolated from the following species of plants:

*Acer campestre* L., *Acer chienii* Hu et Cheng, *Acer chingii* Hu, *Acer davidii* Franch, *Acer laxiflorum* Pax, *Acer mandshuricum* Maxim., *Acer mono* Maxim., *Acer orientale* L., *Acer palmatum* Thunb., *Acer sinense* Pax, *Acer wilsonii* Redhd., *Acer yui* Fang, *Aesculus arguta, Aesculus assamica* Griff., *Aesculus californica* (Spach) Nutt., *Aesculus chinensis* Bunge, *Aesculus chinensis* var. *Chekiangensis* (Hu et Fang) Fang, *Aesculus chuniana* Hu et Fang, *Aesculus flava* (*A. octandra*), *Aesculus glabra* Willd., *Aesculus hippocastanum*, *Aesculus indica, Aesculus lantsangensis* Hu et Fang, *wangii Aesculus megaphylla* Hu et Fang, *chinensis Aesculus neglecta, Aesculus octandra* Marsh., *Aesculus parviflora*, *Aesculus pavia, Aesculus polyneura* Hu et Fang, *Aesculus tsianguii* Hu et Fang, *Aesculus sylvatica, Aesculus turbinata*, *Aesculus wangii* Hu, *Aesculus wangii* var. *ruticola* Hu et Fang, *Aesculus wilsonii, Allophylus caudatus* Radlk. [*A. racemosus* auct. Non (L.) Radlk], *Allophylus chartaceus* (Kurz.) Radlk., *Allophylus cobbe* (Linn.) Raeuch. var. *velutinus* Corner, *Allophylus dimorphus* Radlk., *Allophylus hirsutus* Radlk., *Allophylus longipes* Radlk., *Allophylus petelotii* Merr., *Allophylus repandifolius* Merr. et Chun, *Allophylus timomsis* (DC.) Bl., *Allophylus tricophyllus* Merr. et Chun, *Allophylus viridis* Radlk., *Amesiodendron chinense* (Merr.) Hu, *Amesiodendron integrifoliolatum* H. S. Lo, *Amesiodendron tienlinense* H. S. Lo, *Aphania oligophylla* (Merr. et Chun) H. S. Lo, *Aphania rubra* (Roxb.) Radlk., *Arytera littoralis* Bl., *Blighia sapida, Boniodendron minus* (Hemsl.) T. Chen, *Barringtonia, Camellia axillaris* Roxb. ex Ker, *Camellia cordifolia* (Mech.) Hakai, *Camellia édithae* Hance, *Camellia irrawadiensis* Barua, *Camellia pitardii* Coh. Stuart, *Camellia reticulate* Lindl., *Camellia rosthomiana* Hand.-Mazz., *Camellia sinensis* O. Ktze., *Camellia tenli* Sealy, *Camellia tsaii* Hu, *Camellia wardii* Kobuski, *Camellia yunnanensis* Coh. Stuart, *Cardiospermum halicacabum* L., *Cupaniopsis anacardioides, Delavaya toxocarpa* Franch., *Dimocarpus confinis* (How et Ho) H. S. Lo, *Dimocarpus fumatus* (Bl.) Leenh. subsp. *cacicola* C. Y. Wu, *Dimocarpus longan* Lour. (*Euphoria longan* Lour.) Steud., *Dimocarpus yunanensis* (W. T. Wang) C. Y. Wu et T. Y. Ming, *Dipteronia dyerana* Henry, *Dipteronia sinensis* Oliv., *Dipteronia sinensis* Oliv. var. *taipeiensis* Fang et Fang f., *Dodonaea microzyga, Dodonaea viscosa* (L) Jacq. [*Ptelea viscosa* L.], *Erioglossum rubiginosum* (Roxb.) Bl., *Erythrophysa alata*, *Eurycorymbus austrosinensis* Hand.-Mazz., *Eurycorymbus cavaleriei* (Lével.) Rehd. et Hand.-Mazz., *Handeliodendron bodnieri* (Lévl.) Rehd., *Harpullia alata* F. Mueller, *Harpullia arborea* (Blanco) Rdlk., *Harpullia austro-calcdonica* Baillon, *Harpullia camptoneura* Radlk., *Harpullia cauliflora* K. Schum. & Lauterb., *Harpullia crustacea* Radlk., *Harpullia cupanoides* Roxb., *Harpullia frutescens* F. M. Bailey, *Harpullia giganteacapsula* M. Vente, *Harpullia hillii* F. Muell., *Harpullia hirsuta* Radlk., *Harpullia largifolia* Radlk., *Harpullia leptococca* Radlk., *Harpullia myrmecophila* Merr. & Perry, *Harpullia longipetala* Leench, *Harpullia peekeliana* Melch., *Harpullia pendula* Planch. ex F. muell., *Harpullia petiolaris* Radlk., *Harpullia ramiflora* Radlk., *Harpullia rhachiptera* Rdlk., *Harpullia rhyticarpa* C. T. White & Francis, *Harpullia solomenensis* M. Vente, *Harpullia vaga* Merr. & Perry, *Hypelate trifoliate, Koelreuteria apiculata* Rehd. et Wils., *Koelreuteria bipinnata* Franch., *Koelreuteria bipinnata* var. *integrifoliola* (Merr.) T. chen (*K. integrifoliola* Merr.), *Koelreuteria elegans* (Seem.) A. C. Smith susp. *formosana* (Hayata) Meye, *Koelreuteria monor* Hemsl., *Koelreuteria paniculata* Laxm., *Lepisanthes basicardia* Radlk., *Lepisanthes browniana* Hiern, *Lepisanthes hainanensis* H. S. Lo, *Litchi chinensis* Sonn., *Maesa hupehensis* Rehl., *Maesa japonica* (Thunb.) Moritzi, *Maesa lanceolata, Maesa laxiflora, Maesa montana* A. DC., *Maesa perlarius* (Lour.) Merr. *Maesa tenera* Mez, *Melicoccus bijuatus, Mischocarpus hainanensis* H. S. Lo, *Mischocarpus pentapetalus* (Roxb.) Radlk., *Mischocarpus sundaicus* Bl., *Nephelium Chryseum* Bl., *Nephelium lappaceum, Nephelium topengii* (Merr.) H. S. Lo, *Otophora unilocularis* (Leenh.) H. S. Lo, *Paranephelium hainanensis* H. S. Lo, *Paranephelium hystrix* W. W. Smith, *Pavieasia kwangsiensis* H. S. Lo, *Pavieasia yunnanensis* H. S. Lo, *Pittosporum balancae* DC., *Pittosporum brevicalyx* (Oliv.) Gagnep., *Pittosporum crassifolium* A. Cunn., *Pittosporum crispulum* Gagnep., *Pittosporum daphyniphylloides* Hayata, *Pittosporum elevaticostatum* H. T. Chang et Yan, *Pittosporum eugennioides* A. Cunn., *Pittosporum glabratum* Lindl., *Pittosporum glabratum* Lindl. var. *neriifolium* Rehd., *Pittosporum heterophyllum* Franch., *Pittosporum illicioides* Makino, *Pittosporum kerrii* Craib, *Pittosporum kunmingense* H. T. Chang et Yan, *Pittosporum leptosepalum*

Gowda, *Pittosporum napaulense* (DC.) Rehd. et Wils., *Pittosporum omeiense* H. T. Chang et Yan, *Pittosporum ovoideum* Gowda, *Pittosporum parvicapsulare* H. T. Chang et Yan, *Pittosporum pauciflorum* Hook. et Am., *Pittosporum pentandrum* var. *hainanense* (Gangnep.) H. L. Li, *Pittosporum perryanum* Gowda, *Pittosporum phillyraeoides* DC., *Pittosporum planilobum* H. T. Chang et Yan, *Pittosporum podocarpum* Gagnep., *Pittosporum podocarpum* Gagnep., *Pittosporum pulchrum* Gagnep., *Pittosporum rehderianum* Gowda, *Pittosporum rhombifolium* A. Cunn. ex Hook., *Pittosporum sahnianum* Gowda, *Pittosporum subulisepalum* Hu et Wang, *Pittosporum tenuifolium* Gaertn., *Pittosporum tobira* (Thunb.) Ait., *Pittosporum tobira* (Thunb.) Ait., var. *calvescens* Ohwi, *Pittosporum tonkenese* Gagnep., *Pittosporum trigonocarpum* Lévl., *Pittosporum truncatum* Pritz., *Pittosporum undulatifolium* H. T. Chan et Yan, *Pittosporum undulatum* Venten., *Pittosporum viridiflorum*, *Pittosporum xylocarpum* Hu et Wang, *Pometia pinnata* J. R. et G. Forst., *Ptelea trifoliate*, *Ptelea viscosa* Linn., *Sapindus abruptus* Lour., *Sapindus Chinesis* Murray, *Sapindus delavayi* (Franch.) Radlk. [*Pancovia delavayi* Franch], *Sapindus mukorossi* Gaertn., *Sapindus rarak* DC., *Sapindus rarak* DC., var. *velutinus* C. Y. Wu, *Sapindus saponaria* var. *drummondii*, *Sapindus tomentosus* Kurz, *Ungnadia speciosa*, *Xanthoceras sorbifolia* Bunge. *Xeropspermum bonii* (Lecomte) Radlk.

This invention provides a compound comprising the structures recited in FIGS. 1 to 27. This invention provides a compound comprising a triterpenoidal saponin, triterpenoid, triterpenoidal compound or sapongenin, comprising two angeloyl group or at least two side groups selected from the group consisting of: angeloyl groups, tigloyl groups and senecioyl groups, wherein the side groups are attached to carbon 21 and 22 of triterpenoidal saponin, triterpenoid, triterpenoidal compound or sapongenin backbone. In an embodiment, the saponin comprising a sugar moiety, wherein the sugar moiety comprises at least one sugar, or D-glucose, or D-galactose, or L-rhamnose, or L-arabinose, or D-xylose, or alduronic acid, or D-glucuronic acid or D-galacturonic acid, or their derivative thereof, or the combination, thereof. A sugar moiety is a segment of molecule comprising one or more sugar group. The above compounds are obtainable from the above-described plants. The compounds comprising the structure in FIG. 1 to 27 are obtainable from the above-described plants.

This invention further provides composition comprising the structures recited in FIGS. 1 to 27, or a compound comprising a triterpenoidal saponin, triterpenoid, triterpenoidal compound or sapongenin, comprising at least two side groups selected from the group consisting of: angeloyl groups, tigloyl groups and senecioyl groups, wherein the side groups are attached to carbon 21, 22 or 28 of triterpenoidal saponin, triterpenoid, triterpenoidal compound or sapongenin backbone. These compositions are obtainable from the above-identified plants.

This invention further provides composition comprising the structures recited in FIGS. 1 to 27, or a compound comprising two angeloyl groups or at least two side groups selected from the group consisting of: angeloyl groups, tigloyl groups and senecioyl groups, This invention provides uses of the saponins isolated from the roots, kernel, leave, bark, stem, husk, seed, seed shell or fruit of the above plants, and methods of their preparations.

This invention provides a method of preparing the saponins, comprising the steps of:

(a) extracting roots, kernel, leave, bark, stem, husk, seed, seed shell or fruit or combinations thereof of the above plant with organic solvents such as ethanol or methanol to obtain a organic extract;

(b) collecting the organic extract;

(c) refluxing the organic extract to obtain a second extract;

(d) removing the organic solvent from the second extract to obtain a third extract;

(e) drying and sterilizing the third extract to obtain a crude extract powder;

(f) fractionating the crude extract powder into fractions or components. Fractionation may be achieved by HPLC and FPLC chromatography with silica gel, C18 or other equivalent solid phase materials;

(g) monitoring the fractions. If using HPLC or FPLC, absorption wavelength at 207 nm to 500 nm may be used;

(h) identifying the bioactive components of the crude extract;

(i) purifying one or more bioactive components of the crude extract with chromatographic techniques that employ FPLC to obtain one or more fraction of the bioactive component; and (j) isolating the bioactive components with chromatographic techniques that employ preparative columns and HPLC.

The following is an example of methods and materials that were used to test the bioactivities of Saponins or compounds of this invention.

Cells. Human cancer cell lines were obtained from American Type Culture Collection: HTB-9 (bladder), HeLa-S3 (cervix), DU145 (prostate), H460 (lung), MCF-7 (breast), K562 (leukocytes), HCT116 (colon), HepG2 (liver), U2OS (bone), T98G (brain), SK-MEL-5 (Skin) and OVCAR-3 (ovary). Cells were grown in culture medium (HeLa-S3, DU145, MCF-7, Hep-G2 and T98G in MEN (Earle's salts); HTB-9, H460, K562, OVCAR-3 in RPMI-1640; HCT-116, U2OS in McCoy-5A) supplemented with 10% fetal calf serum, glutamine and antibiotics in a 5% $CO_2$ humidified incubator at 37° C.

MTT Assay. The procedure for MTT assay followed the method described in (Carmichael et al., 1987) with modifications. Cells were seeded into a 96-wells plate at concentrations of 10,000/well (HTB-9, HeLa, H460, HCT116, T98G, OVCAR-3), 15,000/well (DU145, MCF-7, HepG2, U2OS), or 40,000/well (K562), for 24 hours before drug-treatment. Cells were then exposed to drugs for 48 hours (72 hours for HepG2, U2OS, and 96 hours for MCF-7). After the drug-treatment, MTT (0.5 mg/ml) was added to cultures for an hour. The formation of formazan (product of the reduction of tetrazolium by viable cells) was dissolved with DMSO and the O.D. at 490 nm was measured by an ELISA reader. The MTT level of cells before drug-treatment was also measured (T0). The % cell-growth (% G) is calculated as:

$$\% G = (TD-T0/TC-T0) \times 100 \quad (1),$$

where TC or TD represent O.D. readings of control or drug-treated cells. When T0>TD, then the cytotoxicity (LC) expressed as % of the control is calculated as:

$$\% LC = (TD-T0/T0) \times 100 \quad (2)$$

This invention provides a composition effective in reducing or inhibiting cancer growth. The cancer includes but is not limited to bladder cancer, bone cancer and ovary cancer.

This invention provides a composition comprising triterpenoidal saponins or their derivatives for inhibiting tumor growth.

This invention provides a compound selected from a compound of formula (1):

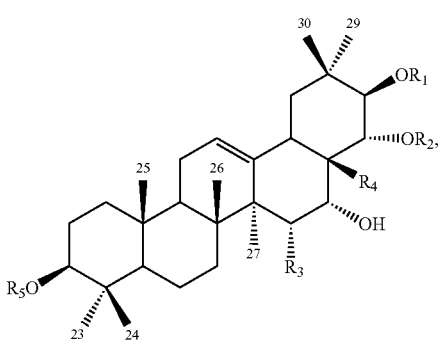

(1)

or a salt, ester, metabolite or derivative thereof, wherein R1 and R2 represent angeloyl group; R3 represents H or OH; R4 represent CH2OR6; and wherein R6 is H; R5 represents at least one sugar moiety or its derivatives.

In an embodiment, R1 and R2 represent angeloyl group; R3 represents H or OH; R4 represents COOR6 wherein R6 is H.

In an embodiment, R1 represents H; R2 represents angeloyl group; R3 represents H or OH; R4 represents CH2OR6 or COOR6; wherein R6 is an angeloyl group.

In another embodiment, R4 represents CH2OR6 or COOR6; at least two of R1, R2, and R6 comprise an angeloyl group or acid having five carbons; R3 represents H or OH; and wherein R6 is angeloyl group, H, acetyl group, tigloyl group, senecioly group, or an acid having two to five carbons.

In a further embodiment, at least one angeloyl of R1 or R2 is replaced by acetyl group, tigloyl group, senecioly group, or an acid having two to five carbons; R3 represents H or OH; R4 represents CH2OR6 or COOR6; and wherein R6 is angeloyl group.

In a further embodiment, the R4 represents CH2OR6 or COOR6; and wherein R6 is H or acetyl.

In a further embodiment, at least one of R1, R2, and R4 comprises a sugar moiety or is a compound comprises sugar moiety, wherein the sugar moiety comprises at least two angeloyl groups, acetyl group, tigloyl group, senecioly group, or an acid having two to five carbons or combination thereof. In a further embodiment, positions 23, 24, 25, 26, 29, 30 of the compound independently comprise CH3, CH2OH, CHO, COOH, alkyls group, acetyl group or derivative thereof.

In a further embodiment, R5 represents sugar moiety comprising glucose, galactose or/and arabinose.

In a further embodiment, R5 represents sugar moiety, wherein the sugar moiety comprises two sugars selected from D-glucose, D-galactose, L-rhamnose, L-arabinose, D-xylose, alduronic acid, D-glucuronic acid, D-galacturonic acid, and derivative thereof, and the combination thereof.

In a further embodiment, R5 represents sugar moiety, wherein the sugar moiety comprises three sugars selected from D-glucose, D-galactose, L-rhamnose, L-arabinose, D-xylose, alduronic acid, D-glucuronic acid, D-galacturonic acid, and derivative thereof, and the combination thereof.

In a further embodiment, R5 represents sugar moiety, wherein the sugar moiety comprises three sugars selected from D-glucose, D-galactose, L-rhamnose, L-arabinose, D-xylose, and derivative thereof, and the combination thereof.

In a further embodiment, R5 represents sugar moiety, wherein the sugar moiety comprises at least one sugar, or D-glucose, D-galactose, or L-rhamnose, or L-arabinose, or D-xylose, or alduronic acid, or D-glucuronic acid or D-galacturonic acid, or derivative thereof, or the combination thereof.

In an embodiment, R5 represents a compound capable of performing the function of the sugar moiety.

In a further embodiment, the R5 represents H. In a further embodiment, R4 represents H or OH or CH3. In a further embodiment, R1 or/and R2 is a functional group capable of performing the function of the angeloyl. R5 represents a compound capable of performing the function of the sugar moiety.

A sugar moiety is a segment of molecule comprising one or more sugar group. Substitution, deletion and/or addition of any group in the above-described compounds will be apparent to one of ordinary skill in the art based on the teaching of this application. In a further embodiment, the substitution, deletion and/or addition of the group(s) in the compound of the invention does not substantially affect the biological function of the compound. In a further embodiment, the angeloyl groups are in a trans-position on a structure.

This invention provides a compound selected from a compound of formula (2):

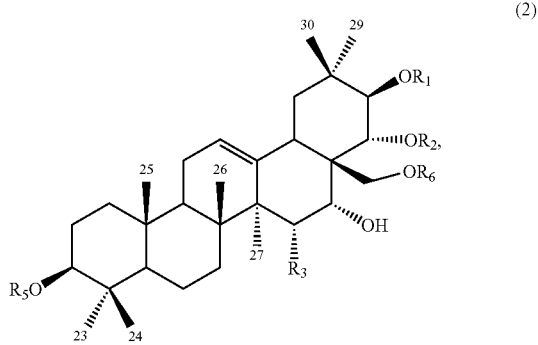

(2)

or a salt, ester or derivative thereof, wherein R1 represents angeloyl group; R2 represents angeloyl group; R3 represents OH or H; Positions 23, 24, 25, 26, 27, 29, of the compound independently comprise CH3, or CH2OH, or CHO, or COOH, alkyls group, or acetyl group, or derivative; R6 represents Ac or H; and R5 represents sugar moiety, wherein the sugar moiety comprises at least one sugar, or D-glucose, or D-galactose, or L-rhamnose, or L-arabinose, or D-xylose, or alduronic acid, or D-glucuronic acid, or D-galacturonic acid, or their derivative thereof, or the combination thereof. In an embodiment, R5 represents a compound capable of performing the function of the sugar moiety. In another embodiment the sugar moiety comprises L-arabinose, D-glucose and/or D-galactose, or combinations thereof. In a further embodiment, any two of R1, R2 or R6 are angeloyl groups, or any one of R1, R2 or R6 is attached to a sugar moiety in which two angeloyl groups are attached to adjacent carbons of the monosaccharides. In a further embodiment, R1, R2, and R6 comprises angeloyl group, acetyl group, tigloyl group, senecioly group, or an acid with two to five carbons or combination thereof. In a further embodiment, at least one of R1, R2 or R6 is attached a sugar moiety, wherein sugar moiety comprises two angeloyl group, acetyl group, tigloyl group, senecioly group, acid having two to five carbons, or combinations thereof.

This invention provides a compound selected from a compound of formula (3):

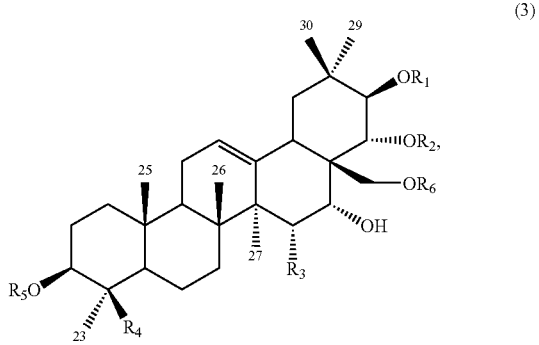

(3)

or a salt, ester or derivative thereof, wherein R1 represents angeloyl group; R2 represents angeloyl group; R3 represents OH or H; R4 represents CH3 or CH2OH or alkyls group or their derivatives; R6 represents Ac or H and R5 represents sugar moiety, wherein the sugar moiety comprises at least one sugar, or D-glucose, or D-galactose, or L-rhamnose, or L-arabinose, or D-xylose, or alduronic acid, or D-glucuronic acid, or D-galacturonic acid, or derivative thereof, or the combination thereof. In an embodiment, R5 represents a compound capable of performing the function of sugar moiety. In another embodiment the sugar moiety comprises L-arabinose, or D-glucose, or D-galactose, or combinations thereof. In a further embodiment, at least one of R1, R2 or R6 is attached a sugar moiety or rhamnose, wherein sugar moiety or rhamnose comprises two angeloyl group, acetyl group, tigloyl group, senecioly group, acid having two to five carbons, or combinations thereof.

This invention provides a compound selected from a compound of formula (4):

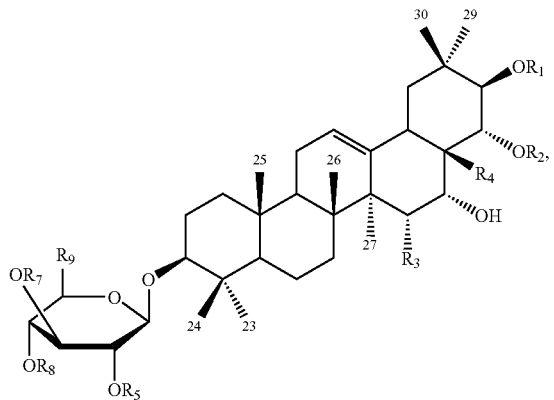

(4)

or a salt, ester, metabolite or derivative thereof, wherein R1 and R2 represent angeloyl group; R3 represents H or OH; R4 represent CH2OR6; and wherein R6 is H or acetyl; R5 represents sugar moiety or D-glucose; R7 represents a sugar moiety or L-arabinose; R8 represents sugar moiety or D-galactose; R9 represent COOH or CH2OH.

In an embodiment, R4 represents COOR6, wherein the R6 is H or acetyl. In an embodiment, the R5, R7 or/and R8 are H or sugar moiety, wherein the sugar moiety comprises at least one sugar, or glucose, or galactose, or rhamnose, or arabinose, or xylose, or alduronic acid, or glucuronic acid or galacturonic acid, or derivative thereof. In an embodiment, at least 2 of R1, R2 and R6 are angeloyl group; R4 represent CH2OR6 or COOR6, wherein R6, R1 and R2 are angeloyl group, acetyl group, tigloyl group, senecioly group, an acid having two to five carbons or H. In a further embodiment, at least two of R1, R2 and R6 are angeloyl group, acetyl group, tigloyl group, senecioly group, or an acid having two to five carbons; R3 represents H or OH; R4 represents CH2OR6 or COOR6, where R6 is H or angeloyl group, acetyl group, tigloyl group, senecioly group.

In an embodiment, R1 and R2 represent angeloyl group; R3 represents H or OH; R4 represents COOR6 wherein R6 is H;

In an embodiment, R1 represents H; R2 represents angeloyl group; R3 represents H or OH; R4 represents CH2OR6 or COOR6; wherein R6 is an angeloyl group.

In another embodiment, at least two of R1, R2, and R6 comprise an angeloyl group; R3 represents H or OH; R4 represents CH2OR6 or COOR6; and wherein R6 is H, angeloyl group, acetyl group, tigloyl group, senecioly group, or an acid having two to five carbons.

In a further embodiment, at least one angeloyl of R1 or R2 is replaced by acetyl group, tigloyl group, senecioly group, or an acid having two to five carbons; R3 represents H or OH; R4 represents CH2OR6 or COOR6; and wherein R6 is angeloyl group.

In a further embodiment, at least one of R1, R2, and R6 is a sugar moiety or rhamnose comprising at least two angeloyl groups, acetyl group, tigloyl group, senecioly group, or an acid having two to five carbons or combination thereof. In a further embodiment, positions 23, 24, 25, 26, 29, 30 of the compound independently comprise CH3, CH2OH, CHO, COOH, alkyls group, acetyl group or derivative thereof. In a further embodiment, R4 represents H or OH or CH3. A sugar moiety is a segment of molecule comprising one or more sugar group.

This invention provides a compound selected from a compound of formula (5):

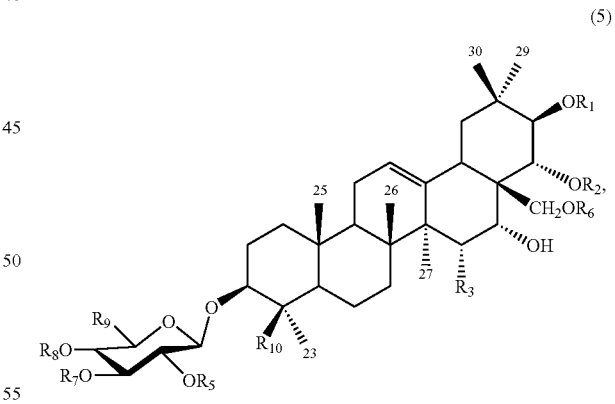

(5)

or a salt, ester, metabolite or derivative thereof, wherein R1 and R2 represent angeloyl group; R3 represents H or OH; R6 represent H or acetyl; R9 represents COOH or CH2OH; R10 represent CH3 or CH2OH or COOH; R5, R7 and R8 are H or/and sugar moiety, wherein the sugar moiety comprises at least one sugar, D-glucose, D-galactose, L-rhamnose, L-arabinose, D-xylose, alduronic acid, D-glucuronic acid, or D-galacturonic acid, or derivative thereof. In an embodiment, at least one of R1, R2, and R6 is a sugar moiety or compound comprising at least two angeloyl groups, acetyl group, tigloyl group, senecioly group, or an acid having two to five carbons or combination thereof. In another embodiment, at least two of R1, R2, and R6 comprise an angeloyl group This invention provides a compound selected from a compound of formula (6):

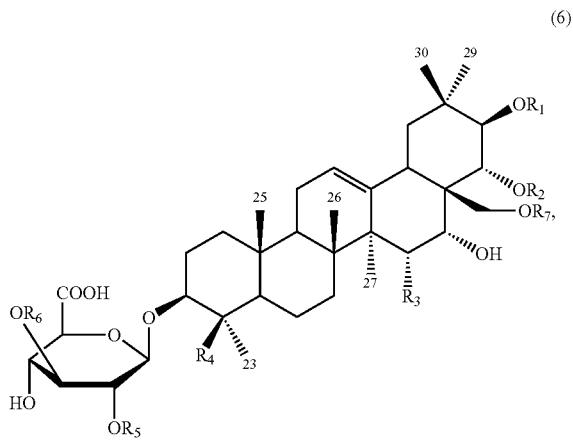

(6)

or a salt, ester or derivative thereof, wherein R1 represents angeloyl group; R2 represents angeloyl group; R3 represents OH or H; R4 represents CH3 or CH2OH; R7 represents H; and R5 represents D-glucose, D-Galactose, L-arabinose or H; and R6 represents D-glucose, D-Galactose, L-arabinose or H. In an embodiment, R5 or/and R6 are H or sugar moiety comprises at least one sugar, D-glucose, D-galactose, L-rhamnose, L-arabinose, D-xylose, alduronic acid, D-glucuronic acid, or D-galacturonic acid, or derivative thereof.

A sugar moiety is a segment of molecule comprising one or more sugar group. Substitution, deletion and/or addition of any group in the above-described compounds will be apparent to one of ordinary skill in the art based on the teaching of this application. In a further embodiment, the substitution, deletion and/or addition of the group(s) in the compound of the invention does not substantially affect the biological function of the compound.

This invention provides a compound selected from a compound of formula (1A):

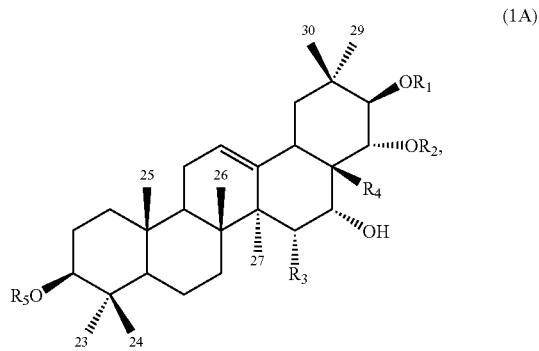

(1A)

or a salt, ester, metabolite or derivative thereof, wherein R1 and R2 independently represent angeloyl group; R3 represents H or OH; R4 represent CH2OR6; and wherein R6 is H; R5 represents at least one sugar moiety or its derivatives.

In an embodiment, R1 and R2 independently represent angeloyl group; R3 represents H or OH; R4 represents COOR6 wherein R6 is H; R5 represents at least one sugar moiety or its derivatives.

In an embodiment, R1 represents H; R2 represents angeloyl group; R3 represents H or OH; R4 represents CH2OR6 or COOR6; wherein R6 is an angeloyl group; and R5 represents at least one sugar moiety or its derivatives.

In another embodiment, R3 represents H or OH; R4 represents CH2OR6 or COOR6; and wherein R6 is angeloyl group, H, acetyl group, tigloyl group, senecioyl group, or an acid having two to five carbons; at least two of R1, R2, and R6 comprise an angeloyl group or acid having five carbons; R5 represents at least one sugar moiety or its derivatives.

In a further embodiment, at least one angeloyl from R1 or R2 is replaced by acetyl group, tigloyl group, senecioyl group, or an acid having two to five carbons; R3 represents H or OH; R4 represents CH2OR6 or COOR6 wherein R6 is angeloyl group; R5 represents at least one sugar moiety or its derivatives.

In a further embodiment, R4 represents CH2OR6 or COOR6; at least one of R1, R2, and R6 is a sugar moiety comprising at least two angeloyl groups, acetyl group, tigloyl group, senecioyl group, or an acid having two to five carbons or combination thereof.

In a further embodiment, position 24 of the compound comprises CH3 or CH2OH.

In a further embodiment, positions 23, 24, 25, 26, 29, 30 of the compound independently comprise CH3 or CH2OH.

In a further embodiment, positions 23, 24, 25, 26, 29, 30 of the compound independently comprise CH3, CH2OH, CHO, COOH, COOalkyl, COOaryl, COO-heterocyclic, COO-heteroaryl, $CH_2$Oaryl, $CH_2$O-heterocyclic, $CH_2$O-heteroaryl, alkyls group, acetyl group or derivative thereof.

In a further embodiment, R5 represents sugar moiety comprising glucose, galactose and arabinose.

In a further embodiment, R5 represents sugar moiety, wherein the sugar moiety comprises at least one sugar, or D-glucose, D-galactose, or L-rhamnose, or L-arabinose, or D-xylose, or alduronic acid, or D-glucuronic acid or D-galacturonic acid, or derivative thereof, or the combination thereof.

In a further embodiment, R5 represents sugar moiety, wherein the sugar moiety comprises two sugars comprising D-glucose, or D-galactose, or L-rhamnose, or L-arabinose, or D-xylose, or alduronic acid, or D-glucuronic acid or D-galacturonic acid, or derivative thereof, or the combination thereof.

In a further embodiment, R5 represents sugar moiety, wherein the sugar moiety comprises at least three sugars selected from D-glucose, or D-galactose, or L-rhamnose, or L-arabinose, or D-xylose, or alduronic acid, or D-glucuronic acid or D-galacturonic acid, or derivative thereof, or the combination thereof.

In a further embodiment, R5 represents sugar moiety, wherein the sugar moiety comprises at least one sugar, glucose, galactose, rhamnose, arabinose, xylose, fucose, allose, altrose, gulose, idose, lyxose, mannose, psicose, ribose, sorbose, tagatose, talose, fructose, alduronic acid, glucuronic acid or galacturonic acid, or derivative thereof, or the combination thereof.

In a further embodiment, R5 represents sugar moiety, wherein the sugar moiety comprises three sugars selected from glucose, galactose, rhamnose, arabinose, xylose, fucose, allose, altrose, gulose, idose, lyxose, mannose, psicose, ribose, sorbose, tagatose, talose, fructose, alduronic acid, glucuronic acid and galacturonic acid, and derivative thereof, and the combination thereof.

In a further embodiment, R5 represents sugar moiety, wherein the sugar moiety comprises three sugars selected from glucose, galactose, rhamnose, arabinose, xylose, fucose, and derivative thereof, and the combination thereof.

In an embodiment, R5 represents a compound capable of performing the function of the sugar moiety. In a further embodiment, the R5 represents H. In a further embodiment, R4 represents H or OH or CH3.

In a further embodiment, R1 or/and R2 is a functional group capable of performing the function of the angeloyl. R5 represents a compound capable of performing the function of the sugar moiety.

In a further embodiment, R1 and R2 are selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl.

In a further embodiment, R1 and R2 comprise angeloyl, tigloyl, senecioyl, benzoyl or alkenoyl.

In a further embodiment, R4 represents CH2OR6; at least two of R1, R2 and R6 are selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl.

In a further embodiment, R4 represents CH2OR6; at least two of R1, R2 and R6 are comprise angeloyl, tigloyl, senecioyl, benzoyl or alkenoyl.

In a further embodiment, R4 represents CH2OR6; at least two of R1, R2 and R6 are comprise angeloyl, benzoyl or alkenoyl.

In a further embodiment, R1 and R2 are selected from H, angeloyl, acetyl, tigloyl, senecioyl, alkyl, acyl, benzoyl, dibenzoyl, alkanoyl, alkenoyl, benzoyl alkyl substituted alkanoyl, aryl, heterocylic or heteroraryl; R4 represents CH2OR6 or COOR6; wherein R6 is selected from H, COCH3, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In a further embodiment, R4 represents CH2OR6, COOR6 or CH2COOR6; at least two of R1, R2 and R6 are selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In a further embodiment, at least two of R1, R2 and R4 are comprising angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In a further embodiment, at least two of R1, R2 and R4 comprise angeloyl, acetyl, tigloyl, senecioyl, benzoyl, alkenoyl, or derivative thereof.

In a further embodiment, at least two of R1, R2 and R4 comprise angeloyl, tigloyl, senecioyl, benzoyl, alkenoyl, or derivative thereof.

In a further embodiment, at least two of R1, R2 and R4 comprise a compound capable of performing the function of angeloyl.

In a further embodiment, at least two of R1, R2 and R4 comprise a compound capable of performing the function of benzoyl.

In a further embodiment, R4 represents CH2OR6, COOR6 or CH2COOR6; at least two of R1, R2 and R6 are comprise angeloyl, tigloyl, senecioyl, benzoyl, alkenoyl, benzoyl or derivative thereof.

In a further embodiment, R4 represents CH2OR6, COOR6 or CH2COOR6; R1, R2 and/or R6 is/are sugar moiety, which comprise compounds selected from H, angeloyl, acetyl, tigloyl, senecioly, alkyl, benzoyl, dibenzoyl, alkanoyl, alkenoyl, benzoyl alkyl substituted alkanoyl, aryl, acyl, heterocylic or heteroraryl or derivative thereof.

In a further embodiment, R4 represents CH2OR6, COOR6 or CH2COOR6; R1, R2 and/or R6 is/are sugar moiety, which comprise at least 2 compounds selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In a further embodiment, R4 represents CH2OR6, COOR6 or CH2COOR6; R1, R2 and/or R6 is/are sugar moiety, which comprise at least 2 compounds selected from angeloyl, tigloyl, senecioyl, benzoyl, alkenoyl or derivative thereof.

In a further embodiment, R4 represents CH2OR6, COOR6 or CH2COOR6; R1, R2 and/or R6 is/are sugar moiety, which comprise at least 2 compounds selected from angeloyl, benzoyl, alkenoyl or derivative thereof.

In a further embodiment, a compound selected from formula (1A) comprises at least 2 compounds selected from angeloyl, acetyl, tigloyl, senecioyl, or derivative thereof or a compound capable performing the function of angeloyl.

In a further embodiment, a compound selected from formula (1A) comprise at least 2 compounds selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In a further embodiment, a compound selected from formula (1A) comprises a sugar moiety or a compound capable of performing function of sugar moiety and at least 2 compounds selected from angeloyl, acetyl, tigloyl, senecioyl, or derivative thereof or a compound capable performing the function of angeloyl.

In a further embodiment, a compound selected from formula (1A) comprise a sugar moiety or a compound capable of performing the function of sugar moiety and at least 2 compounds selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In a further embodiment, a compound selected from formula (1A) wherein R1 and R2 comprise compound selected from hydrogen, angeloyl, acetyl, tigloyl, senecioyl, alkyl, benzoyl, dibenzoyl, alkanoyl, alkenoyl, benzoyl alkyl substituted alkanoyl, aryl, acyl, acyl, heterocylic or heteroraryl or derivative thereof. R4 is a compound comprising CH2OCCH3, CH2COOalkyl, CH2OH, COOH, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

A sugar moiety is a segment of molecule comprising one or more sugar group. Substitution, deletion and/or addition of any group in the above-described compounds will be apparent to one of ordinary skill in the art based on the teaching of this application. In a further embodiment, the substitution, deletion and/or addition of the group(s) in the compound of the invention does not substantially affect the biological function of the compound.

This invention provides a compound selected from a compound of formula (1B):

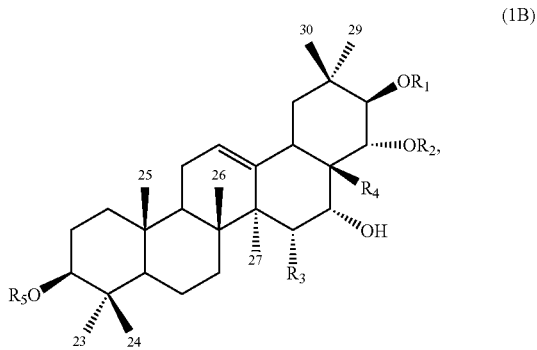

(1B)

or a salt, ester, metabolite or derivative thereof, wherein R1 comprise compound selected from hydrogen, angeloyl, acetyl, tigloyl, senecioyl, alkyl, dibenzoyl, benzoyl, alkanoyl, alkenoyl, benzoyl alkyl substituted alkanoyl, aryl, heterocylic or heteroraryl or derivative thereof; R2 comprise compound selected from hydrogen, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof; R4 represents CH2OR6, COOR6 wherein R6 is selected from hydrogen, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof; R3 is H or OH; R5 represents sugar moiety, wherein the sugar moiety comprises at least one sugar, D-glucose, D-galactose, L-rhamnose, L-arabinose, D-xylose, alduronic acid, D-glucuronic acid or D-galacturonic acid or derivative thereof, or the combination thereof.

In an embodiment, R1 represent a sugar moiety comprises at least two compound selected from, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In an embodiment, R1 represent a sugar moiety comprises at least one compound selected from, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In an embodiment, R2 represent a sugar moiety comprises at least one compound selected from, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In an embodiment, R2 represent a sugar moiety or a compound comprises at least two compound selected from, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In an embodiment, R4 represents CH2OR6, COOR6 wherein R6 is a sugar moiety which comprises at least one compound selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In an embodiment, R4 represents CH2OR6, COOR6 wherein R6 is a sugar moiety which comprises at least two compounds selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In an embodiment, R4 represents CH2OR6, COOR6 wherein R6 is a sugar moiety which comprises at least two compounds selected from angeloyl, acetyl, tigloyl, senecioyl, alkyl, In an embodiment, R4 represents CH2OR6, COOR6 wherein R6 is a sugar moiety which comprises at least two compounds selected from angeloyl, acetyl, tigloyl, senecioyl, alkyl, benzoyl, dibenzoyl, alkanoyl, alkenoyl, dibenzoyl, benzoyl alkyl substituted alkanoyl, aryl, acyl, heterocylic or heteroraryl or derivative thereof.

In an embodiment, R4 represents CH2OR6, COOR6 of formula (1B), at least two of R1, R2 and R6 comprise the compound selected from angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In an embodiment, R4 represents CH2OR6, COOR6 of formula (1B), at least two of R1, R2 and R6 comprise angeloyl, benzoyl, alkenoyl, or derivative thereof.

In an embodiment, R4 is a compound comprising CH2OCCH3, CH2COOalkyl, CH2OH, COOH, angeloyl, acetyl, tigloyl, senecioyl, alkyl, benzoyl, dibenzoyl, alkanoyl, alkenoyl, benzoyl alkyl substituted alkanoyl, aryl, acyl, heterocylic or heteroraryl or derivative thereof.

In a further embodiment, R5 represents sugar moiety, wherein the sugar moiety comprises at least one sugar, glucose, galactose, rhamnose, arabinose, xylose, fucose, allose, altrose, gulose, idose, lyxose, mannose, psicose, ribose, sorbose, tagatose, talose, fructose, alduronic acid, glucuronic acid or galacturonic acid, or derivative thereof, or the combination thereof.

In a further embodiment, R5 represents sugar moiety, wherein the sugar moiety comprises two sugars selected from glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivative thereof, and the combination thereof.

In a further embodiment, R5 represents sugar moiety, wherein the sugar moiety comprises three sugars selected from glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivative thereof, and the combination thereof.

In a further embodiment, R5 represents sugar moiety, wherein the sugar moiety comprises at least four sugars selected from glucose, galactose, rhamnose, arabinose, xylose, fucose, allose, altrose, gulose, idose, lyxose, mannose, psicose, ribose, sorbose, tagatose, talose, fructose, alduronic acid, glucuronic acid, galacturonic acid, and derivative thereof, and the combination thereof.

In a further embodiment, R5 represents sugar moiety, wherein the sugar moiety comprises three sugars selected from glucose, galactose, rhamnose, arabinose, xylose, fucose, and derivative thereof, and the combination thereof.

In an embodiment, R5 represents sugar moiety or a compound capable of performing the function of the sugar moiety.

In a further embodiment, the R5 represents H.

In a further embodiment, R4 represents H or OH or CH3.

In a further embodiment, positions 23, 24, 25, 26, 29, 30 of the compound independently comprise CH3, CH2OH, CHO, COOH, COOalkyl, COOaryl, COO-heterocyclic, COO-heteroaryl, CH$_2$Oaryl, CH$_2$O-heterocyclic, CH$_2$O-heteroaryl, alkyls group, acetyl group or derivative thereof.

deletion and/or addition of the group(s) in the compound of the invention does not substantially affect the biological function of the compound.

This invention provides a compound selected from a compound of formula (1C):

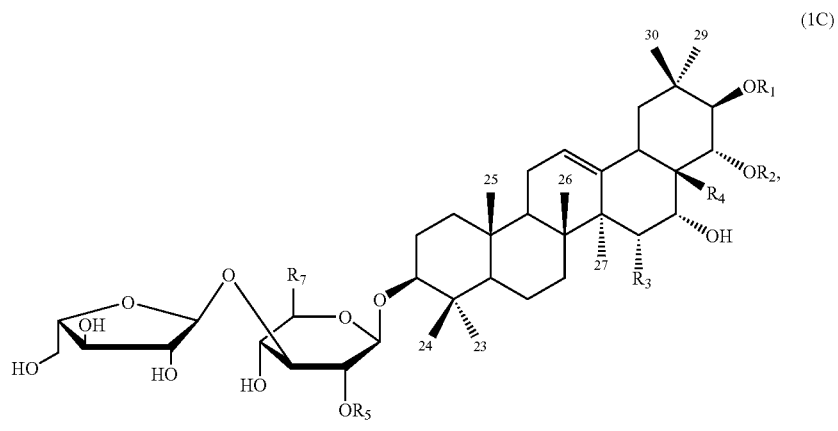

(1C)

In a further embodiment, R5 represents sugar moiety selected from D-glucose, D-galactose, L-rhamnose and L-arabinose and their combination thereof.

In a further embodiment, R5 represents sugar moiety comprising D-glucose, D-galactose and L-arabinose or their combination thereof.

In a further embodiment, R5 represents sugar moiety comprising D-glucose, D-galactose, L-rhamnose, D-xylose or L-arabinose or their combination thereof or derivative thereof.

In a further embodiment, R5 represents sugar moiety, wherein the sugar moiety comprises at least two sugar selected from D-glucose, D-galactose, L-rhamnose, L-arabinose, D-xylose, alduronic acid, D-glucuronic acid, D-galacturonic acid and derivative thereof, and the combination thereof.

In a further embodiment, R5 represents sugar moiety, wherein the sugar moiety comprises three sugars selected from D-glucose, D-galactose, L-rhamnose, L-arabinose, D-xylose, alduronic acid, D-glucuronic acid, D-galacturonic acid and derivative thereof, and the combination thereof.

In a further embodiment, R5 represents sugar moiety, wherein the sugar moiety comprises at least three sugars selected from D-glucose, D-galactose, L-rhamnose, L-arabinose, D-xylose, alduronic acid, D-glucuronic acid, D-galacturonic acid and derivative thereof, and the combination thereof.

In a further embodiment, R1 and R2 independently comprise an angeloyl group.

In a further embodiment, R1 is a sugar moiety or a compound which comprise two angeloyl groups.

In a further embodiment, R1 and R2 independently comprise a benzoyl group.

In a further embodiment, R1 is a sugar moiety which comprises two benzoyl groups.

In a further embodiment, R3 represents H or OH.

A sugar moiety is a segment of molecule comprising one or more sugar group. Substitution, deletion and/or addition of any group in the above-described compounds will be apparent to one of ordinary skill in the art based on the teaching of this application. In a further embodiment, the substitution, or a salt, ester, metabolite or derivative thereof, wherein R1 and R2 independently represent angeloyl group; R3 represents H or OH; R4 represent CH2OR6 wherein R6 is H; R5 represents sugar moiety or D-glucose, D-galactose or its derivatives. R7 represent COOH In an embodiment, R1 and R2 independently represent angeloyl group; R3 represents H or OH; R4 represents COOR6 wherein R6 is H; R5 represents sugar moiety or D-glucose, D-galactose or its derivatives. R7 represent COOH.

In an embodiment, R1 represents H; R2 represents angeloyl group; R3 represents H or OH; R4 represents CH2OR6 or COOR6; wherein R6 is an angeloyl group or acetyl group.

In another embodiment, at least two of R1, R2, and R6 comprise an angeloyl group or acid having five carbons; R3 represents H or OH; R4 represents CH2OR6 or COOR6; and wherein R6 is angeloyl group, H, acetyl group, tigloyl group, senecioyl group, or an acid having two to five carbons.

In a further embodiment, at least one angeloyl from R1 or R2 is replaced by acetyl group, tigloyl group, senecioyl group, or an acid having two to five carbons; R3 represents H or OH; R4 represents CH2OR6 or COOR6 wherein R6 is angeloyl group.

In a further embodiment, R4 represents CH2OR6 or COOR6; at least one of R1, R2, and R6 is a sugar moiety comprising at least two angeloyl groups, acetyl group, tigloyl group, senecioyl group, or an acid having two to five carbons or combination thereof.

In a further embodiment, positions 24 of the compound comprise CH3 or CH2OH.

In a further embodiment, R7 represent COOH, CH2OH or CH3.

In a further embodiment, R7 represent CH3, CH2OH, CHO, COOH, COOalkyl.

In a further embodiment, R7 represent CH3, CH2OH, CHO; COOH, COOalkyl, COOaryl, COO-heterocyclic, COO-heteroaryl, CH$_2$Oaryl, CH$_2$O-heterocyclic, CH$_2$O-heteroaryl, alkyls group, acetyl group or derivative thereof.

In a further embodiment, positions 24 of the compound comprise CH3 or CH2OH.

In a further embodiment, positions 23, 24, 25, 26, 29, 30 of the compound independently comprise CH3, CH2OH.

In a further embodiment, positions 23, 24, 25, 26, 29, 30 of the compound independently comprise CH3, CH2OH, CHO, COOH, COOalkyl, COOaryl, COO-heterocyclic, COO-heteroaryl, CH$_2$Oaryl, CH$_2$O-heterocyclic, CH$_2$O-heteroaryl, alkyls group, acetyl group or derivative thereof.

In a further embodiment, R5 represents sugar moiety comprising glucose or galactose.

In a further embodiment, R5 represents sugar moiety, or D-glucose, D-galactose, or L-rhamnose, or L-arabinose, or D-xylose, or alduronic acid, or D-glucuronic acid or D-galacturonic acid, or derivative thereof, or the combination thereof.

In a further embodiment, R5 represents sugar moiety, glucose, galactose, rhamnose, arabinose, xylose, fucose or derivative thereof.

In a further embodiment, R5 represents sugar moiety, glucose, galactose, rhamnose, arabinose, xylose, fucose, allose, altrose, gulose, idose, lyxose, mannose, psicose, ribose, sorbose, tagatose, talose, fructose, alduronic acid, glucuronic acid or galacturonic acid, or derivative thereof, or the combination thereof.

In an embodiment, the R5 represents H.

In a further embodiment, R4 represents CH2OR6 wherein R6 represent H or acetyl group.

In a further embodiment, R4 represents H or OH or CH3.

In a further embodiment, R1 or/and R2 is a functional group capable of performing the function of the angeloyl. R5 represents a compound capable of performing the function of the sugar moiety.

In a further embodiment, R1 and R2 are selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof.

In a further embodiment, R1 or/and R2 is a sugar moiety comprise two of compounds selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof.

In a further embodiment, R1 and R2 are selected from H, angeloyl, acetyl, tigloyl, senecioyl, alkyl, benzoyl, alkanoyl, alkenoyl, benzoyl alkyl substituted alkanoyl, aryl, acyl, heterocylic or heteroraryl; R4 represents CH2OR6 or COOR6; wherein R6 is selected from H, COCH3, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof.

In a further embodiment, R4 represents CH2OR6, COOR6 or CH2COOR6; at least two of R1, R2 and R6 are selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof.

In a further embodiment, R4 represents CH2OR6, COOR6 or CH2COOR6; R1, R2 and/or R6 is/are sugar moiety, which comprise compounds selected from H angeloyl, acetyl, tigloyl, senecioly, alkyl, benzoyl, alkanoyl, alkenoyl, benzoyl alkyl substituted alkanoyl, aryl, acyl, heterocylic or heteroraryl or derivative thereof.

In a further embodiment, R4 represents CH2OR6, COOR6 or CH2COOR6; R1, R2 and/or R6 is/are sugar moiety, which comprise at least 2 compounds selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof.

In a further embodiment, a compound selected from formula (1C) comprises at least 2 compounds selected from angeloyl, acetyl, tigloyl, senecioyl, or derivative thereof or a compound capable performing the function of angeloyl.

In a further embodiment, a compound selected from formula (1C) comprise at least 2 compounds selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof.

In a further embodiment, a compound selected from formula (1C) wherein R1 and R2 comprise compound selected from hydrogen, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof. R4 is a compound comprising CH2OCCH3, CH2COOalkyl, CH2OH, COOH, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof.

A sugar moiety is a segment of molecule comprising one or more sugar group.

Substitution, deletion and/or addition of any group in the above-described compounds will be apparent to one of ordinary skill in the art based on the teaching of this application. In a further embodiment, the substitution, deletion and/or addition of the group(s) in the compound of the invention does not substantially affect the biological function of the compound.

This invention provides a compound selected from a compound of formula (1D):

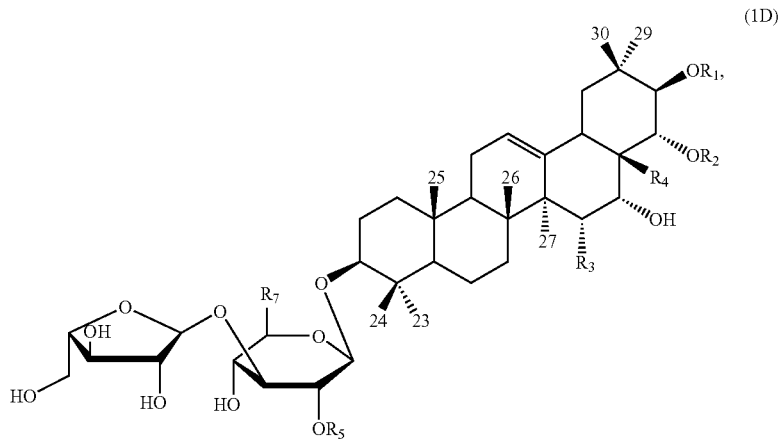

or a salt, ester, metabolite or derivative thereof, wherein R1 comprise compound selected from hydrogen, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof; R2 comprise compound selected from hydrogen, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof; R4 represents CH2OR6, COOR6 wherein R6 is selected from hydrogen, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof; R3 is H or OH; R5 represents sugar moiety, or D-glucose or D-galactose; R7 represent COOH In an embodiment, R7 represent CH3, CH2OH, COOH, COOalkyl, In an embodiment, R7 represent CH3, CH2OH, CHO, COOH, COOalkyl, COOaryl, COO-heterocyclic, COO-heteroaryl, $CH_2O$aryl, $CH_2O$-heterocyclic, $CH_2O$-heteroaryl, alkyls group, acetyl group or derivative thereof.

In an embodiment, R1 represent a compound comprising a sugar moiety comprises at least two compound selected from, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof;

In an embodiment, R1 represent a compound comprising a sugar moiety comprises at least one compound selected from, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof;

In an embodiment, R2 represent a compound comprising a sugar moiety comprises at least one compound selected from, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof;

In an embodiment, R2 represent a compound comprising a sugar moiety or a compound which comprises at least two compound selected from, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof;

In an embodiment, R4 represents CH2OR6, COOR6 wherein R6 is a sugar moiety which comprises at least one compound selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof;

In an embodiment, R4 represents CH2OR6, COOR6 wherein R6 is a sugar moiety which comprises at least two compounds selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof;

In an embodiment, R4 represents CH2OR6, COOR6 wherein R6 is a sugar moiety which comprises at least two compounds selected from angeloyl, acetyl, tigloyl, senecioyl, alkyl, In an embodiment, R4 represents CH2OR6, COOR6 wherein R6 is a sugar moiety which comprises at least two compounds selected from angeloyl, acetyl, tigloyl, senecioyl, alkyl, benzoyl, alkanoyl, alkenoyl, dibenzoyl, benzoyl alkyl substituted alkanoyl, aryl, acyl, heterocylic or heteroraryl or derivative thereof;

In an embodiment, R4 represents CH2OR6, COOR6 wherein at least two of R1, R2 and R6 comprise the compound selected from angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof;

In an embodiment, R4 is a compound comprising CH2OCCH3, CH2COOalkyl, CH2OH, COOH, angeloyl, acetyl, tigloyl, senecioyl, alkyl, benzoyl, alkanoyl, alkenoyl, benzoyl alkyl substituted alkanoyl, aryl, acyl, heterocylic or heteroraryl or derivative thereof.

In a further embodiment, R5 represents sugar moiety, glucose, galactose, rhamnose, arabinose, xylose, fucose, allose, altrose, gulose, idose, lyxose, mannose, psicose, ribose, sorbose, tagatose, talose, fructose, alduronic acid, glucuronic acid or galacturonic acid, or derivative thereof, or the combination thereof.

In an embodiment, R5 represents a compound capable of performing the function of the sugar moiety. In a further embodiment, the R5 represents H. In a further embodiment, R4 represents H or OH or CH3.

In an embodiment, position 24 of the compound comprise CH3 or CH2OH,

In a further embodiment, positions 23, 24, 25, 26, 29, 30 of the compound independently comprise CH3, CH2OH, CHO, COOH, COOalkyl, COOaryl, COO-heterocyclic, COO-heteroaryl, $CH_2O$aryl, $CH_2O$-heterocyclic, $CH_2O$-heteroaryl, alkyls group, acetyl group or derivative thereof.

In a further embodiment, R5 represents sugar moiety comprising L-glucose, D-galactose, L-rhamnose, or/and L-arabinose.

In a further embodiment, R1 and R2 independently represent angeloyl group; In a further embodiment, R1 is a sugar moiety or rhamnose which comprise two angeloyl groups.

In a further embodiment, R3 represents H or OH; A sugar moiety is a segment of molecule comprising one or more sugar group. Substitution, deletion and/or addition of any group in the above-described compounds will be apparent to one of ordinary skill in the art based on the teaching of this application. In a further embodiment, the substitution, deletion and/or addition of the group(s) in the compound of the invention does not substantially affect the biological function of the compound.

This invention provides a method of inhibiting tumor cell growth comprising administering to a subject, in need thereof, an appropriate amount of triterpenoidal saponins comprising two or more angeloyl groups or comprising the structure of FIGS. 1-27.

This invention provides a composition comprising the compounds as described above effective in reducing or inhibiting cancer growth. The cancer includes but is not limited to bladder cancer, bone cancer, skin cancer and ovarian cancer.

The saponins isolated from *Xanthoceras sorbifolia* with the characteristic structure described in the present invention can be used for anti-cancer therapy. The cancer includes but is not limited to bladder cancer, bone cancer, skin cancer and ovarian cancer.

Figure 1:
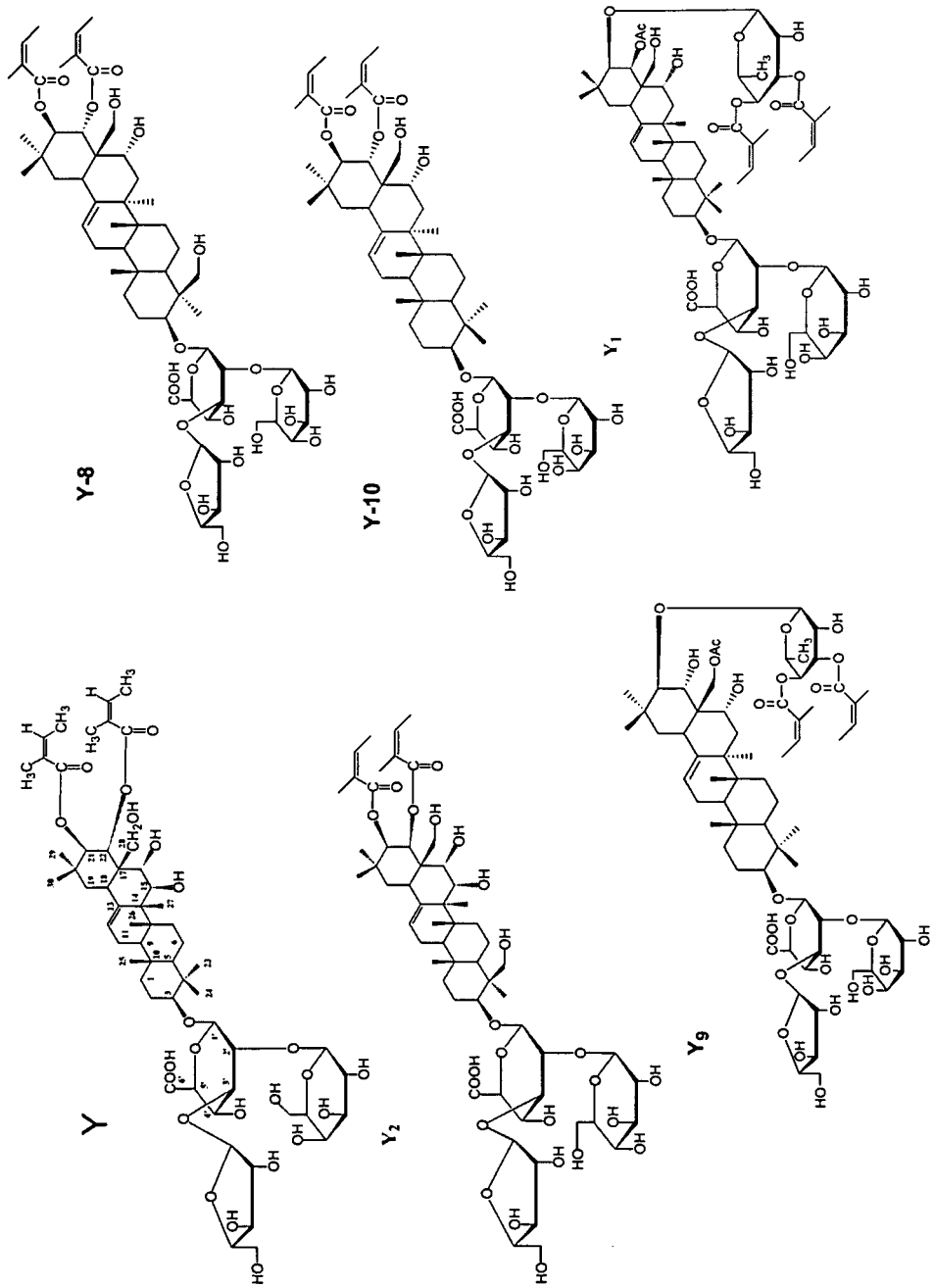
Figure 2:
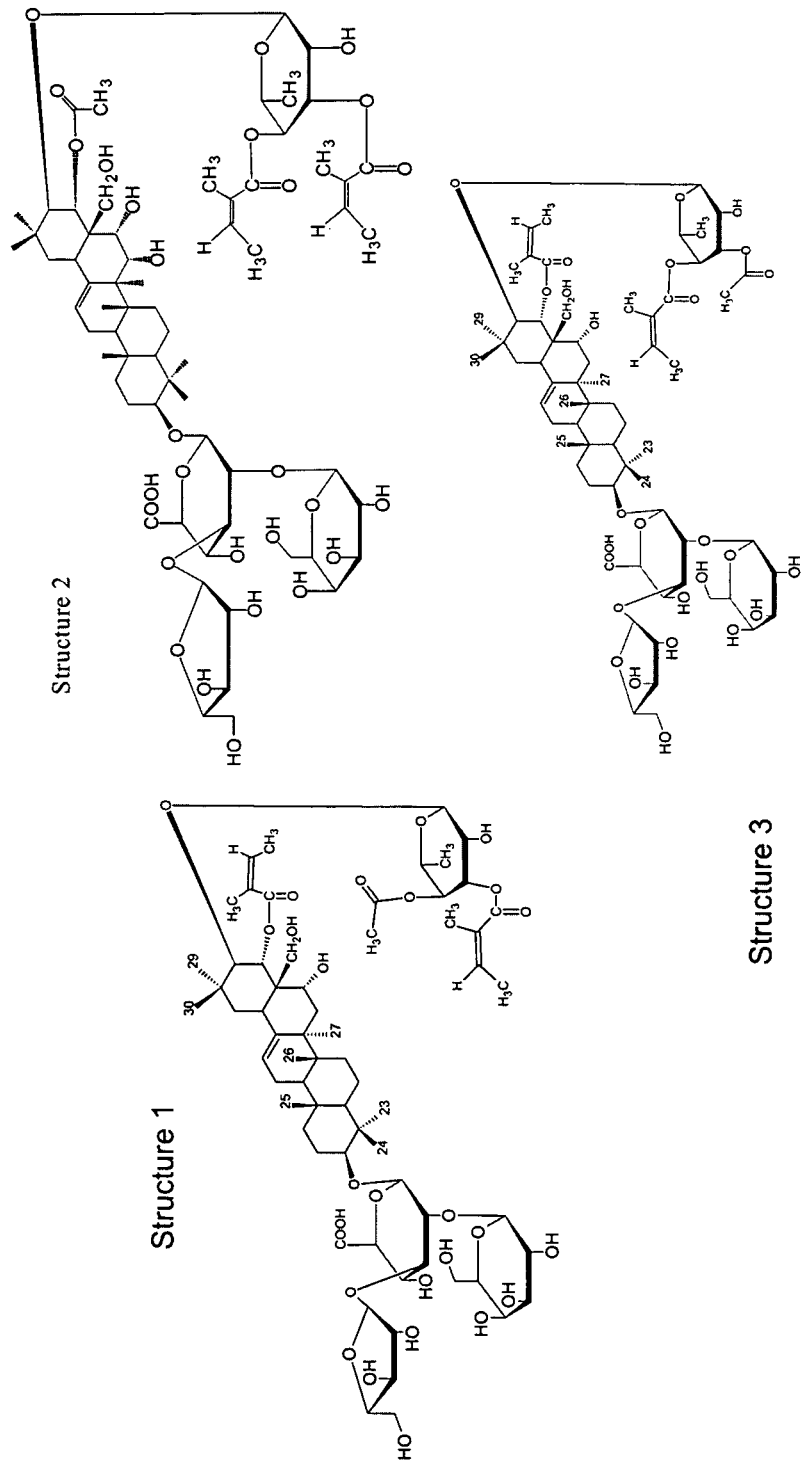
Figure 3:
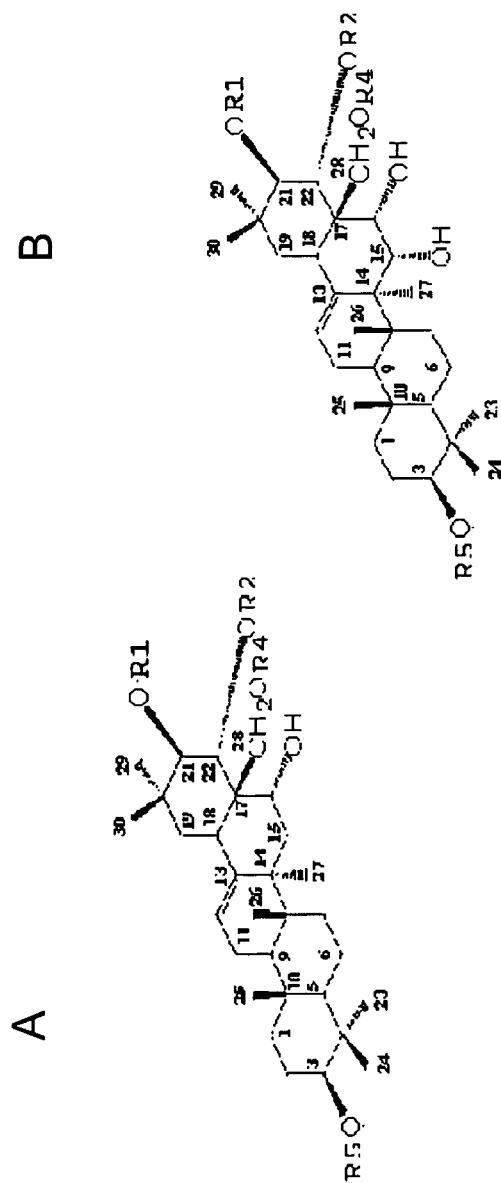
Figure 4:
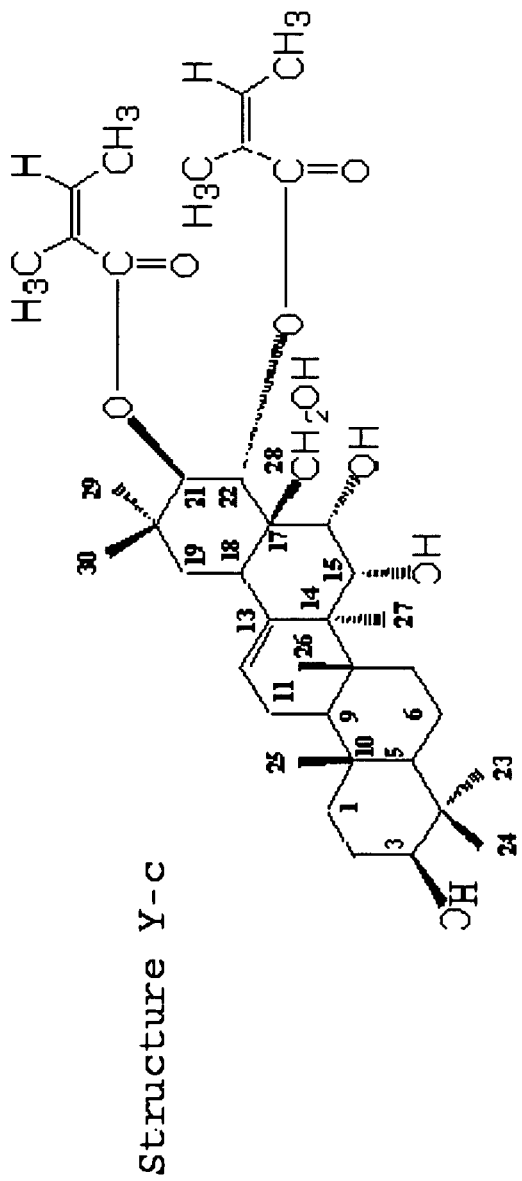
Figure 5:
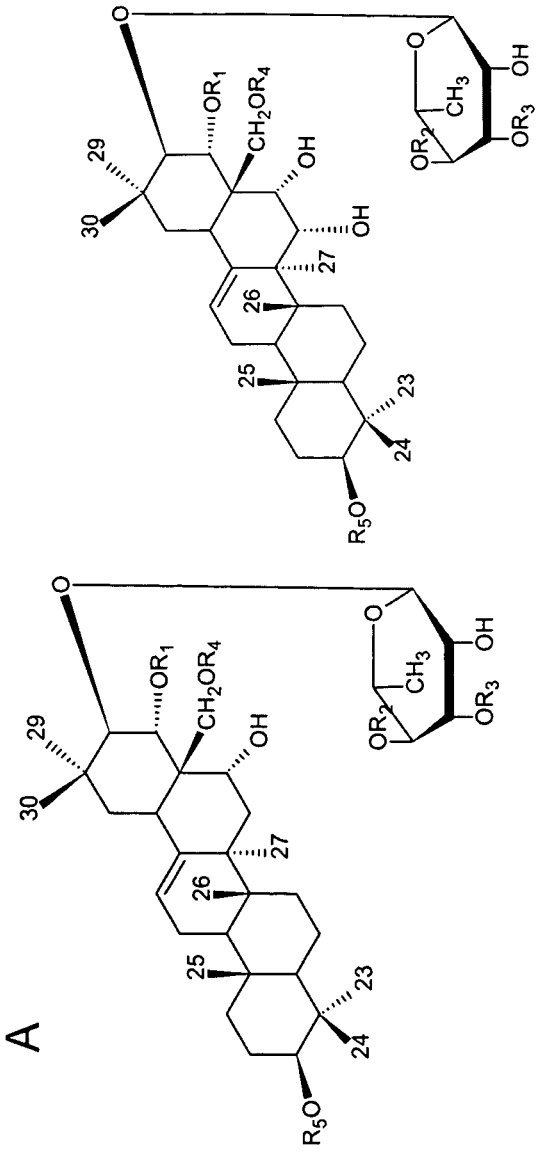
Figure 6:
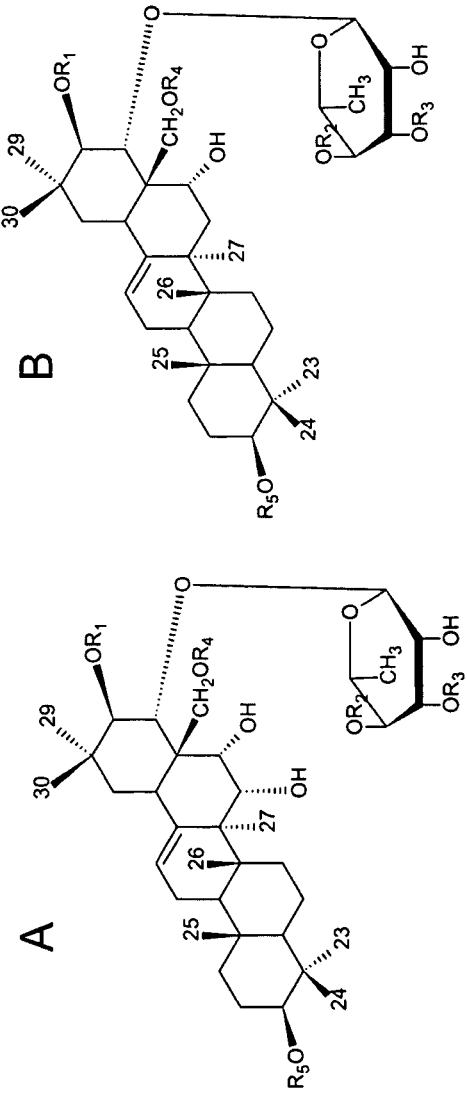
Figure 7:
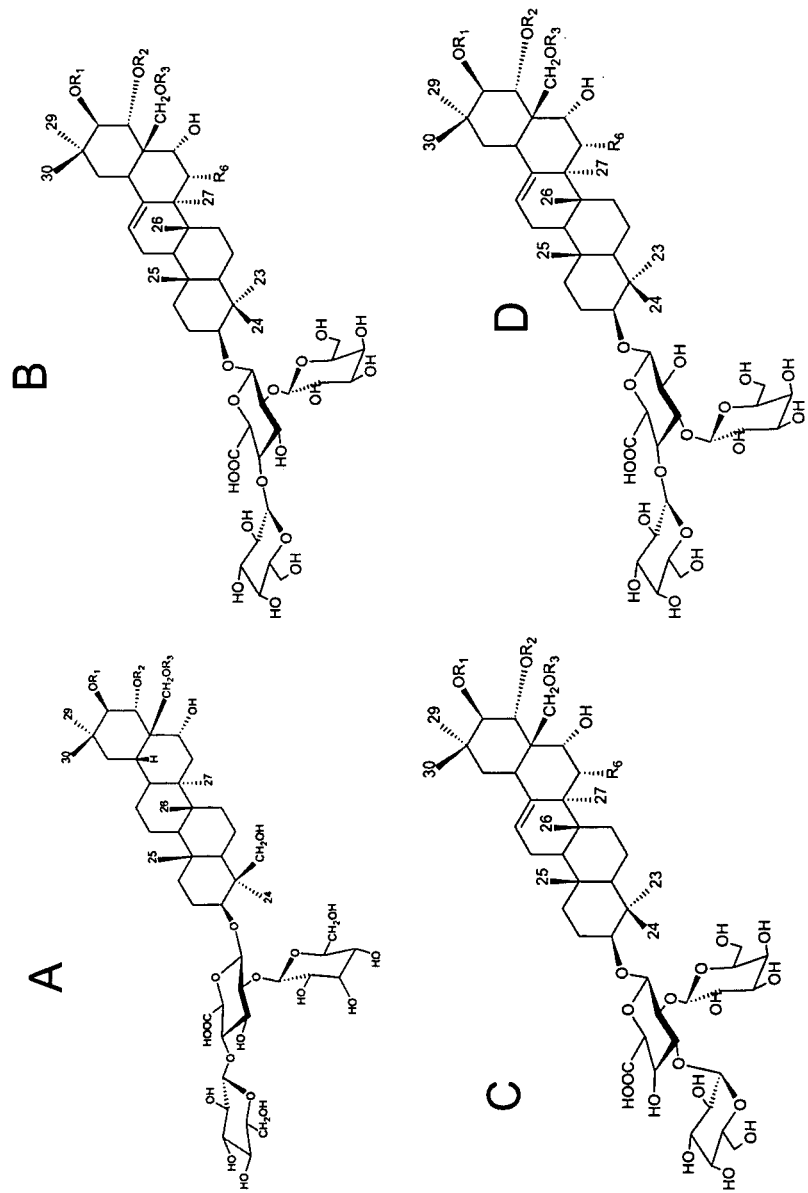

This invention provides a composition comprising the above described compounds or their derivatives for treating human immunodeficiency virus (HIV), Severe Acute Respiratory Syndrome (SARS), flu disease or inhibits virus activities. The biologically active triterpenoid saponins structures are shown in FIG. 1

Triterpenoid saponins comprises the formula as following: 3-O-{[β-D-galactopyranosyl(1→2)]-[α-L-arabinofuranosyl (1→3)]-β-D-glucuronopyranoside butyl ester}-21-O-acetyl-22-O-angeloyl-3β, 16α, 21β, 22α, 28-pentahydroxyolean-12-ene.

3-O-[β-D-galactopyranosyl(1→2)]-α-L-arabinofuranosyl(1→3)-β-D-glucuronopyranosyl-21,22-O-diangeloyl-3β, 15α, 16α, 21β, 22α, 28-hexahydroxyolean-12-ene, 3-O-[β-D-galactopyranosyl(1→2)]-α-L-arabinofuranosyl(1→3)-β-D-glucuronopyranosyl-21-O-(3,4-diangeloyl)-α-L-rhamnophyranosyl-22-O-acetyl-3β, 16α, 21β, 22α, 28-pentahydroxyolean-12-ene, 3-O-[β-D-glucopyranosyl-(1→2)]-α-L-arabinofuranosyl(1→3)-β-D-glucuronopyranosyl-21,22-O-diangeloyl-3β, 15α, 16α, 21β, 22α, 24β, 28-heptahydroxyolean-12-ene, 3-O-[β-glucopyranosyl(1→2)]-α-arabinofuranosyl(1→3)-β-glucuronopyranosyl-21,22-O-diangeloyl-3β, 16α, 21β, 22α, 24β, 28-hexahydroxyolean-12-ene, 3-O-[β-galactopyranosyl(1→2)]-α-arabinofuranosyl(1→3)-β-glucuronopyranosyl-21-O-(3,4-diangeloyl)-α-rhamnopyranosyl-28-O-acetyl-3β, 16α, 21β, 22α, 28-pentahydroxyolean-12-ene, 3-O-[β-galactopyranosyl(1→2)]-α-arabinofuranosyl(1→3)-β-glucuronopyranosyl-21,22-O-diangeloyl-3β, 16α, 21β, 22α, 28-pentahydroxyolean-12-ene, This invention provides a composition comprising the compounds as described above effective in reducing or inhibiting cancer growth. The cancer includes but is not limited to bladder cancer, bone, cancer, skin cancer and ovarian cancer.

This invention provides a composition for reducing or inhibiting cancer growth comprising any of compound selected from following:

A) 3-O-[β-D-galactopyranosyl(1→2)]-α-L-arabinofuranosyl(1→3)-β-D-glucuronopyranosyl-21,22-O-diangeloyl-3β, 15α, 16α, 21β, 22α, 28-hexahydroxyolean-12-ene, B) 3-O-[β-D-galactopyranosyl(1→2)]-α-L-arabinofuranosyl(1→3)-β-D-glucuronopyranosyl-21-O-(3,4-diangeloyl)-α-L-rhamnophyranosyl-22-O-acetyl-3β, 16α, 21β, 22α, 28-pentahydroxyolean-12-ene C) 3-O-[β-D-glucopyranosyl-(1→2)]-α-L-arabinofuranosyl(1→3)-(-D-glucuronopyranosyl-21,22-O-diangeloyl-3β, 15α, 16α, 21β, 22α, 24β, 28-heptahydroxyolean-12-ene D) 3-O-[β-galactopyranosyl(1→2)]-α-arabinofuranosyl(1→3)-β-glucuronopyranosyl-21,22-O-diangeloyl-3β, 16α, 21β, 22α, 28-pentahydroxyolean-12-ene E) 3-O-[β-galactopyranosyl(1→2)]-α-arabinofuranosyl(1→3)-β-glucuronopyranosyl-21-O-(3,4-diangeloyl)-α-rhamnopyranosyl-28-O-acetyl-3β, 16α, 21β, 22α, 28-pentahydroxyolean-12-ene F) 3-O-[β-galactopyranosyl(1→2)]-α-arabinofuranosyl(1→3)-β-glucuronopyranosyl-21,22-O-diangeloyl-3β, 16α, 21β, 22α, 28-pentahydroxyolean-12-ene G) 3-O-[β-D-galactopyranosyl(1→2)]-α-L-arabinofuranosyl(1→3)-β-D-glucuronopyranosyl-21,22-O-dibenzoyl-3β, 15α, 16α, 21β, 22α, 28-hexahydroxyolean-12-ene, H) 3-O-[β-D-galactopyranosyl(1→2)]-α-L-arabinofuranosyl(1→3)-β-D-glucuronopyranosyl-21-O-(3,4-dibenzoyl)-α-L-rhamnophyranosyl-22-O-acetyl-3β, 16α, 21β, 22α, 28-pentahydroxyolean-12-ene I) 3-O-[β-D-glucopyranosyl-(1→2)]-α-L-arabinofuranosyl(1→3)-(-D-glucuronopyranosyl-21,22-O-dibenzoyl-3β, 15α, 16α, 21β, 22α, 24β, 28-heptahydroxyolean-12-ene J) 3-O-[β-galactopyranosyl(1→2)]-α-arabinofuranosyl(1→3)-β-glucuronopyranosyl-21,22-O-dibenzoyl-3β, 16α, 21β, 22α, 28-pentahydroxyolean-12-ene K) 3-O-[β-galactopyranosyl(1→2)]-α-arabinofuranosyl(1→3)-β-glucuronopyranosyl-21-O-(3,4-dibenzoyl)-α-rhamnopyranosyl-28-O-acetyl-3β, 16α, 21β, 22α, 28-pentahydroxyolean-12-ene L) 3-O-[β-galactopyranosyl(1→2)]-α-arabinofuranosyl(1→3)-β-glucuronopyranosyl-21,22-O-dibenzoyl-3β, 16α, 21β, 22α, 28-pentahydroxyolean-12-ene M) 3-O-[β-D-galactopyranosyl(1→2)]-β-D-xyopyranosyl(1→3)-β-D-glucuronopyranosyl-21,22-O-dibenzoyl-3β, 15α, 16α, 21β, 22α, 28-hexahydroxyolean-12-ene, N) 3-O-[β-D-galactopyranosyl(1→2)]-β-D-xyopyranosyl(1→3)-β-D-glucuronopyranosyl-21-O-(3,4-dibenzoyl)-α-L-rhamnophyranosyl-22-O-acetyl-3β, 16α, 21β, 22α, 28-pentahydroxyolean-12-ene O) 3-O-[β-D-glucopyranosyl-(1→2)]-β-D-xyopyranosyl(1→3)-(-D-glucuronopyranosyl-21,22-O-dibenzoyl-3β, 15α, 16α, 21β, 22α, 24β, 28-heptahydroxyolean-12-ene P) 3-O-[β-D-galactopyranosyl(1→2)]-β-D-xyopyranosyl(1→3)-β-D-glucuronopyranosyl-21,22-O-dibenzoyl-3β, 16α, 21β, 22α, 28-pentahydroxyolean-12-ene Q) 3-O-[β-galactopyranosyl(1→2)]-β-xyopyranosyl(1→3)-β-glucuronopyranosyl-21-O-(3,4-dibenzoyl)-α-rhamnopyranosyl-28-O-acetyl-3β, 16α, 21β, 22α, 28-pentahydroxyolean-12-ene R) 3-O-[β-galactopyranosyl(1→2)]-β-xyopyranosyl(1→3)-β-glucuronopyranosyl-21,22-O-dibenzoyl-3β, 16α, 21β, 22α, 28-pentahydroxyolean-12-ene S) 3-O-[β-D-galactopyranosyl(1→2)]-β-D-xyopyranosyl(1→3)-β-D-glucuronopyranosyl-21,22-O-diangeloyl-3β, 15α, 16α, 21β, 22α, 28-hexahydroxyolean-12-ene, T) 3-O-[β-D-galactopyranosyl(1→2)]-β-D-xyopyranosyl(1→3)-β-D-glucuronopyranosyl-21-O-(3,4-diangeloyl)-α-L-rhamnophyranosyl-22-O-acetyl-3β, 16α, 21β, 22α, 28-pentahydroxyolean-12-ene U) 3-O-[β-D-glucopyranosyl-(1→2)]-β-D-xyopyranosyl(1→3)-(-D-glucuronopyranosyl-21,22-O-diangeloyl-3β, 15α, 16α, 21β, 22α, 24β, 28-heptahydroxyolean-12-ene V) 3-O-[β-D-galactopyranosyl(1→2)]-β-D-xyopyranosyl(1→3)-β-glucuronopyranosyl-21,22-O-diangeloyl-3β, 16α, 21β, 22α, 28-pentahydroxyolean-12-ene W) 3-O-[β-galactopyranosyl(1→2)]-β-D-xyopyranosyl(1→3)-β-glucuronopyranosyl-21-O-(3,4-diangeloyl)-α-rhamnopyranosyl-28-O-acetyl-3β, 16α, 21β, 22α, 28-pentahydroxyolean-12-ene X) 3-O-[β-D-galactopyranosyl(1→2)]-β-D-xyopyranosyl(1→3)-β-D-glucuronopyranosyl-21,22-O-diangeloyl-3β, 16α, 21β, 22α, 28-pentahydroxyolean-12-ene This invention provides a composition for reducing or inhibiting cancer growth comprising any of compound selected from following:

A) 3-O-[β-D-galactopyranosyl(1→2)]-α-L-arabinofuranosyl(1→3)-β-D-glucuronopyranosyl-21-O-angeloyl,22-O-benzoyl-3β, 15α, 16α, 21β, 22α, 28-hexahydroxyolean-12-ene, B) 3-O-[β-D-galactopyranosyl(1→2)]-α-L-arabinofuranosyl(1→3)-β-D-glucuronopyranosyl-21-O-(3-angeloyl,4-benzoyl)-α-L-rhamnophyranosyl-22-O-acetyl-3β, 16α, 21β, 22α, 28-pentahydroxyolean-12-ene C) 3-O-[β-D-glucopyranosyl-(1→2)]-α-L-arabinofuranosyl(1→3)-(-D-glucuronopyranosyl-21-O-angeloyl,22-O-benzoyl-3β, 15α, 16α, 21β, 22α, 24β, 28-heptahydroxyolean-12-ene D) 3-O-[β-galactopyranosyl(1→2)]-α-arabinofuranosyl(1→3)-β-glucuronopyranosyl-21-O-angeloyl,22-benzoyl-3β, 16α, 21β, 22α, 28-pentahydroxyolean-12-ene E) 3-O-[β-galactopyranosyl(1→2)]-α-arabinofuranosyl(1→3)-β-glucuronopyranosyl-21-O—F) (3-angeloyl,4-benzoyl)-α-rhamnopyranosyl-28-O-acetyl-3β, 16α, 21β, 22α, 28-pentahydroxyolean-12-ene F) 3-O-[β-galactopyranosyl(1→2)]-α-arabinofuranosyl(1→3)-β-glucuronopyranosyl-21-O-angeloyl,22-O-benzoyl-3β, 16α, 21β, 22α, 28-pentahydroxyolean-12-ene G) 3-O-[β-D-galactopyranosyl(1→2)]-α-L-arabinofuranosyl(1→3)-β-D-glucuronopyranosyl-21-O-benzoyl,22-O-angeloyl-3β, 15α, 16α, 21β, 22α, 28-hexahydroxyolean-12-ene, H) 3-O-[β-D-galactopyranosyl(1→2)]-α-L-arabinofuranosyl(1→3)-β-D-glucuronopyranosyl-21-O-(3-benzoyl,4-angeloyl)-α-L-rhamnophyranosyl-22-O-acetyl-3β, 16α, 21β, 22α, 28-pentahydroxyolean-12-ene I) 3-O-[β-D-glucopyranosyl-(1→2)]-α-L-arabinofuranosyl (1→3)-(-D-glucuronopyranosyl-21-O-benzoyl,22-O-angeloyl-3β, 15α, 16α, 21β, 22α, 24β, 28-heptahydroxyolean-12-ene J) 3-O-[β-galactopyranosyl(1→2)]-α-arabinofuranosyl (1→3)-β-glucuronopyranosyl-21-O-benzoyl,22-O-angeloyl-3β, 16α, 21β, 22α, 28-pentahydroxyolean-12-ene K) 3-O-[β-galactopyranosyl(1→2)]-α-arabinofuranosyl (1→3)-β-glucuronopyranosyl-21-O-(3-benzoyl,4-angeloyl)-α-rhamnopyranosyl-28-O-acetyl-3β, 16α, 21β, 22α, 28-pentahydroxyolean-12-ene L) 3-O-[β-galactopyranosyl(1→2)]-α-arabinofuranosyl (1→3)-β-glucuronopyranosyl-21-O-benzoyl,22-O-angeloyl-3β, 16α, 21β, 22α, 28-pentahydroxyolean-12-ene M) 3-O-[β-D-galactopyranosyl(1→2)]-β-D-xyopyranosyl (1→3)-β-D-glucuronopyranosyl-21-O-angeloyl,22-O-benzoyl-3β, 15α, 16α, 21β, 22α, 28-hexahydroxyolean-12-ene, N) 3-O-[β-D-galactopyranosyl(1→2)]-β-D-xyopyranosyl (1→3)-β-D-glucuronopyranosyl-21-O-(3-angeloyl,4-dibenzoyl)-α-L-rhamnophyranosyl-22-O-acetyl-3β, 16α, 21β, 22α, 28-pentahydroxyolean-12-ene O) 3-O-[β-D-glucopyranosyl-(1→2)]-β-D-xyopyranosyl (1→3)-(-D-glucuronopyranosyl-21-O-21-O-angeloyl,22-O-benzoyl-3β, 15α, 16α, 21β, 22α, 24β, 28-heptahydroxyolean-12-ene P) 3-O-[β-D-galactopyranosyl(1→2)]-β-D-xyopyranosyl (1→3)-β-D-glucuronopyranosyl-2121-O-angeloyl,22-O-benzoyl-3β, 16α, 21β, 22α, 28-pentahydroxyolean-12-ene Q) 3-O-[β-galactopyranosyl(1→2)]-β-xyopyranosyl(1→3)-β-glucuronopyranosyl-21-O-(3-angeloyl,4-dibenzoyl)-α-rhamnopyranosyl-28-O-acetyl-3β, 16α, 21β, 22α, 28-pentahydroxyolean-12-ene R) 3-O-[β-galactopyranosyl(1→2)]-β-xyopyranosyl(1→3)-β-glucuronopyranosyl-angeloyl,22-O-benzoyl-3β, 16α, 21β, 22α, 28-pentahydroxyolean-12-ene S) 3-O-[β-galactopyranosyl(1→2)]-β-D-xyopyranosyl (1→3)-β-D-glucuronopyranosyl-21-O-benzoyl,22-O-angeloyl-3β, 15α, 16α, 21β, 22α, 28-hexahydroxyolean-12-ene, T) 3-O-[β-D-galactopyranosyl(1→2)]-β-D-xyopyranosyl (1→3)-β-D-glucuronopyranosyl-21-O-(3-benzoyl,4-angeloyl)-α-L-rhamnophyranosyl-22-O-acetyl-3β, 16α, 21β, 22α, 28-pentahydroxyolean-12-ene U) 3-O-[β-D-glucopyranosyl-(1→2)]-β-D-xyopyranosyl (1→3)-(-D-glucuronopyranosyl-21-O-benzoyl,22-O-angeloyl-3β, 15α, 16α, 21β, 22α, 24β, 28-heptahydroxyolean-12-ene V) 3-O-[β-galactopyranosyl(1→2)]-β-D-xyopyranosyl (1→3)-β-glucuronopyranosyl-21-O-benzoyl,22-O-angeloyl-3β, 16α, 21β, 22α, 28-pentahydroxyolean-12-ene W) 3-O-[β-galactopyranosyl(1→2)]-β-D-xyopyranosyl (1→3)-β-glucuronopyranosyl-21-O-(3-benzoyl,4-angeloyl)-α-rhamnophyranosyl-28-O-acetyl-3β, 16α, 21β, 22α, 28-pentahydroxyolean-12-ene X) 3-O-[D-galactopyranosyl(1→2)]-β-D-xyopyranosyl (1→3)-β-D-glucuronopyranosyl-21-O-benzoyl,22-O-angeloyl-3β, 16α, 21β, 22α, 28-pentahydroxyolean-12-ene Triterpenoid saponins with the characteristic structure mentioned above in this invention can be used to reduce or inhibit cancer growth. The cancer includes but is not limited to bladder cancer, bone cancer, skin cancer and ovarian cancer. This invention also provides a composition comprising the above described compounds or their derivatives capable of inhibiting human immunodeficiency virus (HIV), Severe Acute Respiratory Syndrome (SARS) or flu disease, or capable of inhibiting viral activities.

The saponins isolated from *Harpullia austro-calcdonica* with the characteristic structure described in the present invention can be used for anti-cancer therapy. The cancer includes but is not limited to bladder cancer, bone cancer and ovarian cancer.

This invention provides a composition comprising the above described compounds or their derivatives for inhibiting human immunodeficiency virus (HIV), Severe Acute Respiratory Syndrome (SARS), flu disease or inhibits virus activities.

The biologically active triterpenoid saponins structures are shown in FIG. 11A. See also Phytochemistry 59 (2002) 825-832, Triterpenoid saponins and acylated prosapogenins from *Harpullia austro-calcdonica*.

Wherein R1=R2=angeloyl group; R3=CH2OH or CH3 or CHO.

Figure 15:
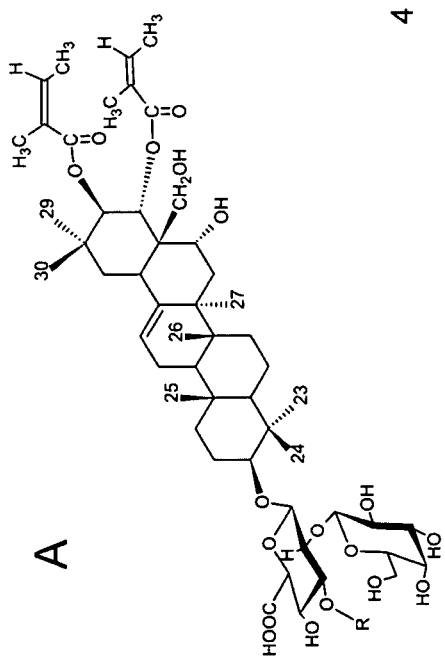
Figure 15:
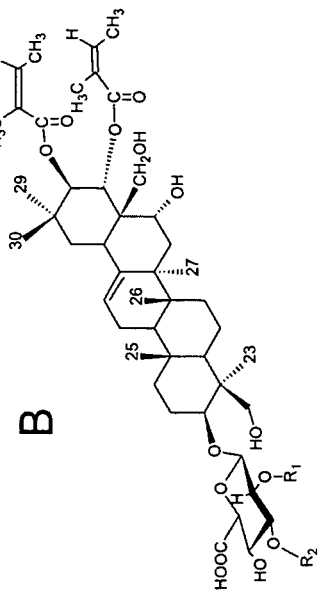

The biologically active triterpenoid saponins structures are shown in FIG. 15. See also Phytochemistry 66 (2005) 825-835, Haemolytic acylated triterpenoid saponins from *Harpullia austro-caledonica*.

Triterpenoid saponins isolated from seeds of *Aesculus chinensis* having the characteristic structure(s) as disclosed in the present invention can be used in anti-cancer therapy. The cancer that triterpenoid saponins is effective against includes but is not limited to bladder cancer, bone cancer and ovarian cancer. This invention provides a composition comprising the above-described compounds and their derivatives for inhibiting cancer, Severe Acute Respiratory Syndrome (SARS), flu disease or inhibits virus activities.

Triterpenoidal saponins comprise the structures shown or described in FIG. 7A.

| Wherein | R1 | R2 | R3 |
|---|---|---|---|
| 1 | Tigloyl | Acetyl | H |
| 2 | Angeloyl | Acetyl | H |
| 3 | Tigloyl | H | H |
| 4 | Angeloyl | H | Acetyl |
| 5 | H | Tigloyl | Acetyl |
| 6 | H | Angeloyl | Acetyl |
| 7 | H | H | Tigloyl |
| 8 | H | H | Angeloyl |

See also J. Nat. Prod. 1999, 62, 1510-1513. Anti-HIV-1 Protease Triterpenoid Saponins from the seed of *Aesculus chinensis*.

Triterpenoid saponins isolated from *Aesculus, Aesculus arguta, Aesculus assamica* Griff., *Aesculus californica* (Spach) Nutt., *Aesculus chinensis* Bunge, *Aesculus* chinensis var. *Chekiangensis* (Hu et Fang) Fang, *Aesculus chuniana* Hu et Fang, *Aesculus flava (A. octandra), Aesculus glabra* Willd., *Aesculus hippocastanum, Aesculus indica, Aesculus lantsangensis* Hu et Fang, *wangii Aesculus megaphylla* Hu et Fang, *chinensis Aesculus neglecta, Aesculus octandra* Marsh., *Aesculus parvifiora, Aesculus pavia, Aesculus polyneura* Hu et Fang, *Aesculus tsianguii* Hu et Fang, *Aesculus sylvatica, Aesculus turbinata, Aesculus wangii* Hu, *Aesculus wangii* var. *ruticola* Hu et Fang or *Aesculus wilsonii*, having the characteristic structure(s) as disclosed in the present invention can be used in anti-cancer therapy. The cancer that triterpenoid saponin is effective against includes but is not limited to bladder cancer, bone cancer and ovarian cancer. This invention provides a composition comprising the above-described compounds and their derivatives for inhibiting cancer, Severe Acute Respiratory Syndrome (SARS), flu disease or inhibits virus activities.

Triterpenoid saponins comprise the structures shown or described in FIG. 7A, 7B, 7C, 7D.

Wherein R1=angeloyl group or tigloyl group or senecioyl group or acetyl or H.

R2=angeloyl group or tigloyl group or senecioyl group or acetyl group or acetyl or H.

R3=angeloyl group or tigloyl group or senecioyl group or acetyl group or acetyl or H.

R6=H or OH

Position 23-27 and 28-30 are attached with CH3 or CH2OH or COOH or CHO

Triterpenoid saponins isolated from *Aesculus, Aesculus arguta, Aesculus assamica* Griff., *Aesculus californica* (Spach) Nutt., *Aesculus chinensis* Bunge, *Aesculus chinensis* var. *Chekiangensis* (Hu et Fang) Fang, *Aesculus chuniana* Hu et Fang, *Aesculus flava* (*A. octandra*), *Aesculus glabra* Willd., *Aesculus hippocastanum, Aesculus indica, Aesculus lantsangensis* Hu et Fang, *wangii Aesculus megaphylla* Hu et Fang, *chinensis Aesculus neglecta, Aesculus octandra* Marsh., *Aesculus parviflora, Aesculus pavia, Aesculus polyneura* Hu et Fang, *Aesculus tsianguii* Hu et Fang, *Aesculus sylvatica, Aesculus turbinata, Aesculus wangii* Hu, *Aesculus wangii* var. *ruticola* Hu et Fang or *Aesculus wilsonii*, having the characteristic structure(s) as disclosed in the present invention can be used in anti-cancer therapy. The cancer that triterpenoid saponin is effective against includes but is not limited to bladder cancer, bone cancer, skin cancer and ovarian cancer. This invention provides a composition comprising the above-described compounds and their derivatives for inhibiting cancer, Severe Acute Respiratory Syndrome (SARS), flu disease or inhibits virus activities.

Figure 16:
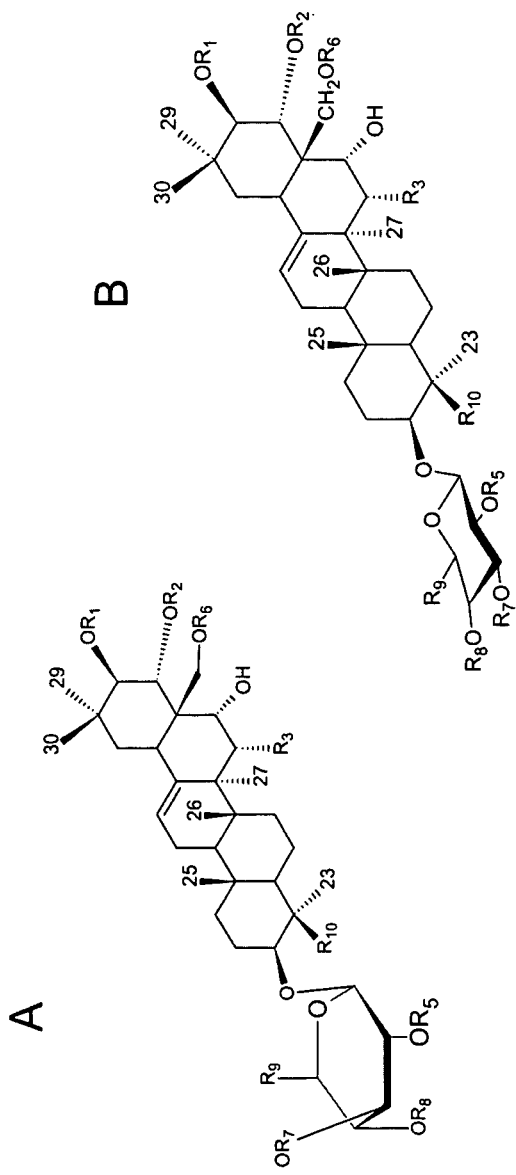

Triterpenoidal saponins comprise the structures shown or described in FIG. 16A, 16 B.

Wherein R1=angeloyl or Tigloyl or Senecioyl or acetyl or H
R2=angeloyl or Tigloyl or Senecioyl or acetyl or H
R6=angeloyl or Tigloyl or Senecioyl or acetyl or H
R3=H or OH
R10=CH3 or CH2OH or CHO
R5=sugar moiety or D-glucose or D-galactose or L-rhamnose or L-arabinose or, D-xylose or alduronic acid or D-glucuronic acid or D-galacturonic acid or H
R7=sugar moiety or D-glucose or D-galactose or L-rhamnose or L-arabinose or, D-xylose or alduronic acid or D-glucuronic acid or D-galacturonic acid or H
R8=sugar moiety or D-glucose or D-galactose or L-rhamnose or L-arabinose or, D-xylose or alduronic acid or D-glucuronic acid or D-galacturonic acid or H
R9=COOH or CH2OH Triterpenoid saponins isolated from the plants described in this invention with the characteristic structure mentioned in this invention can be used to reduce or inhibit cancer growth. The cancer includes but is not limited to bladder cancer, bone cancer, skin cancer and ovarian cancer. This invention also provides a composition comprising the above described compounds or their derivatives capable of inhibiting human immunodeficiency virus (HIV), Severe Acute Respiratory Syndrome (SARS) or flu disease, or capable of inhibiting viral activities.

Figure 17:
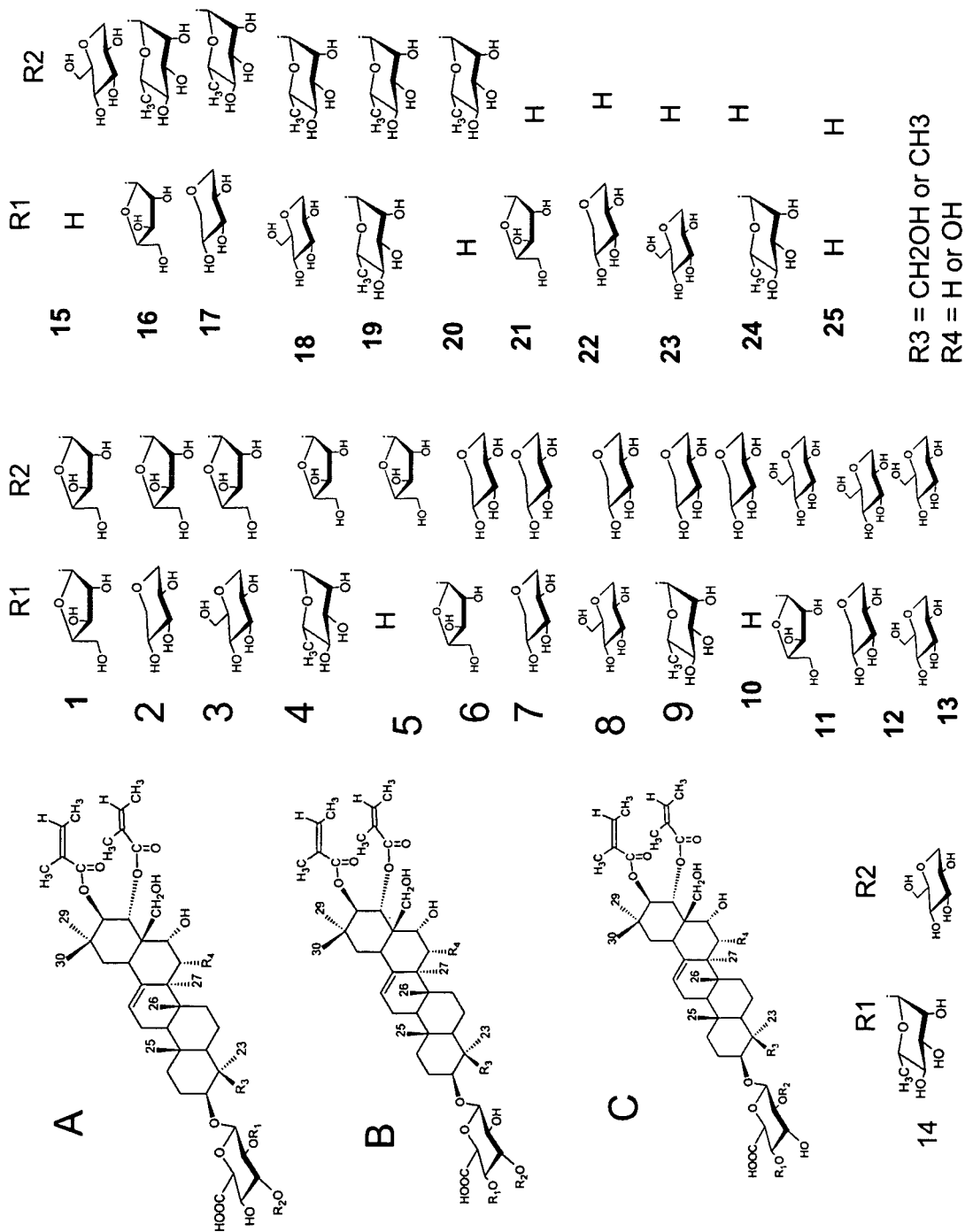
Figure 18:
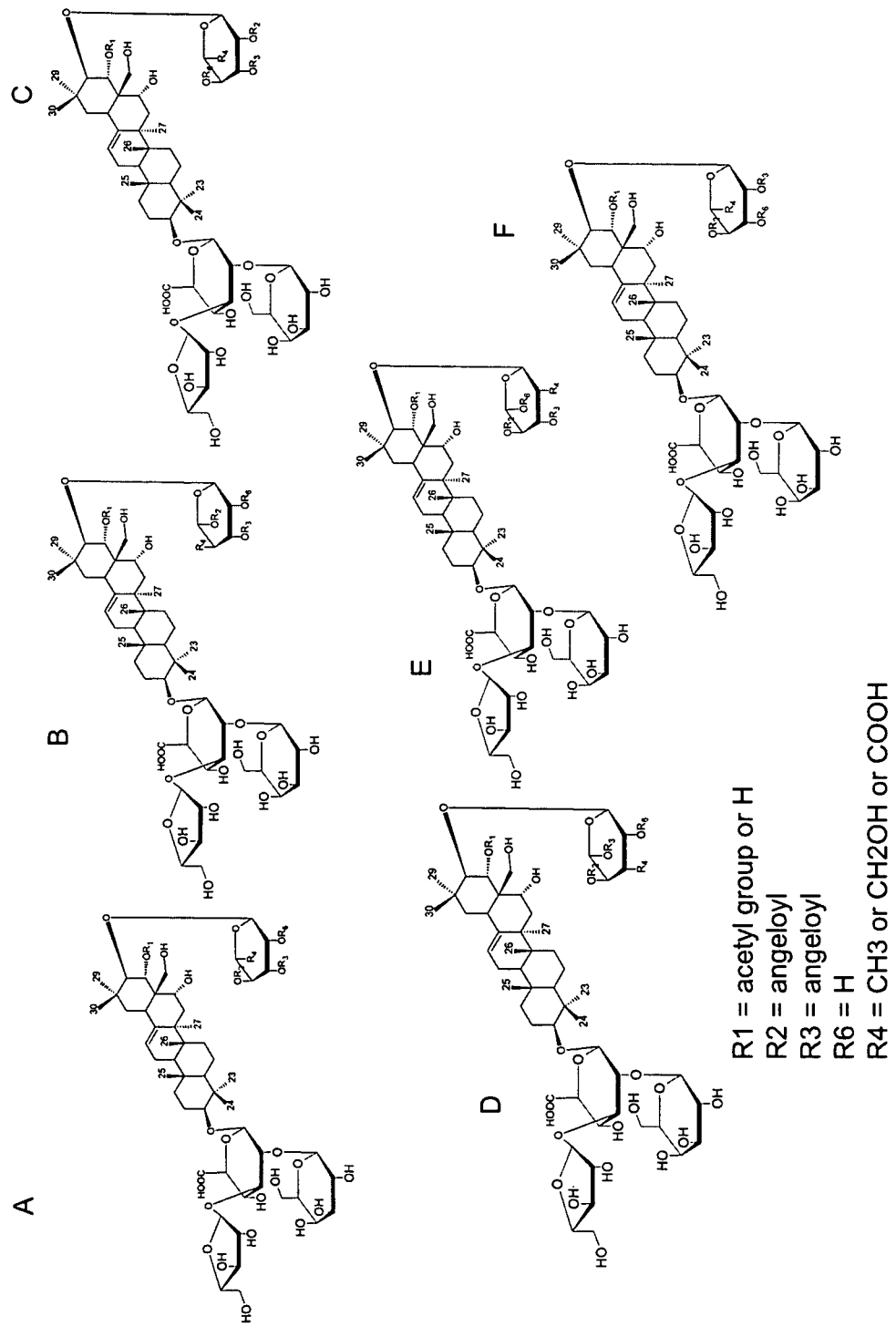
Figure 19:
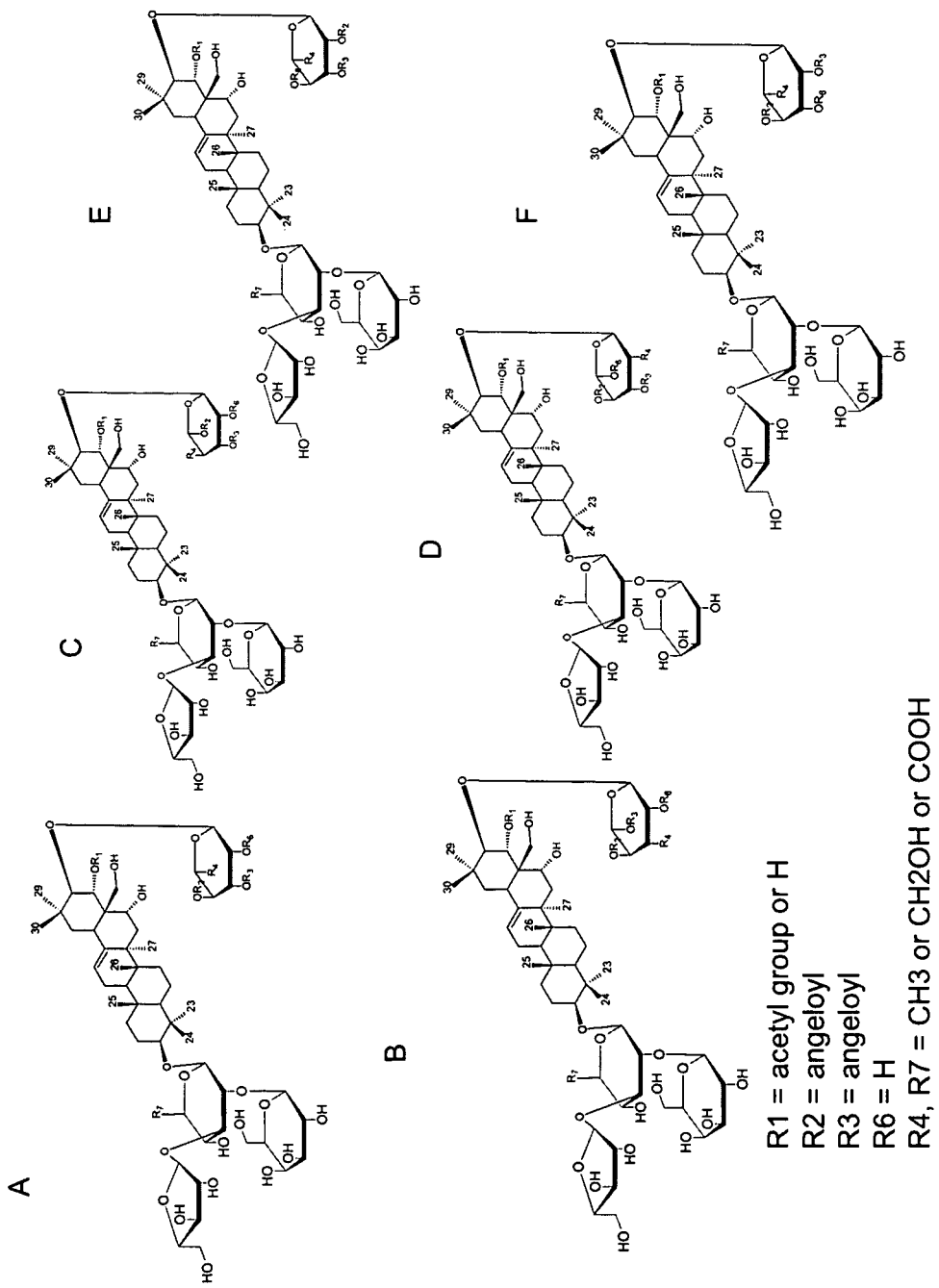
Figure 20:
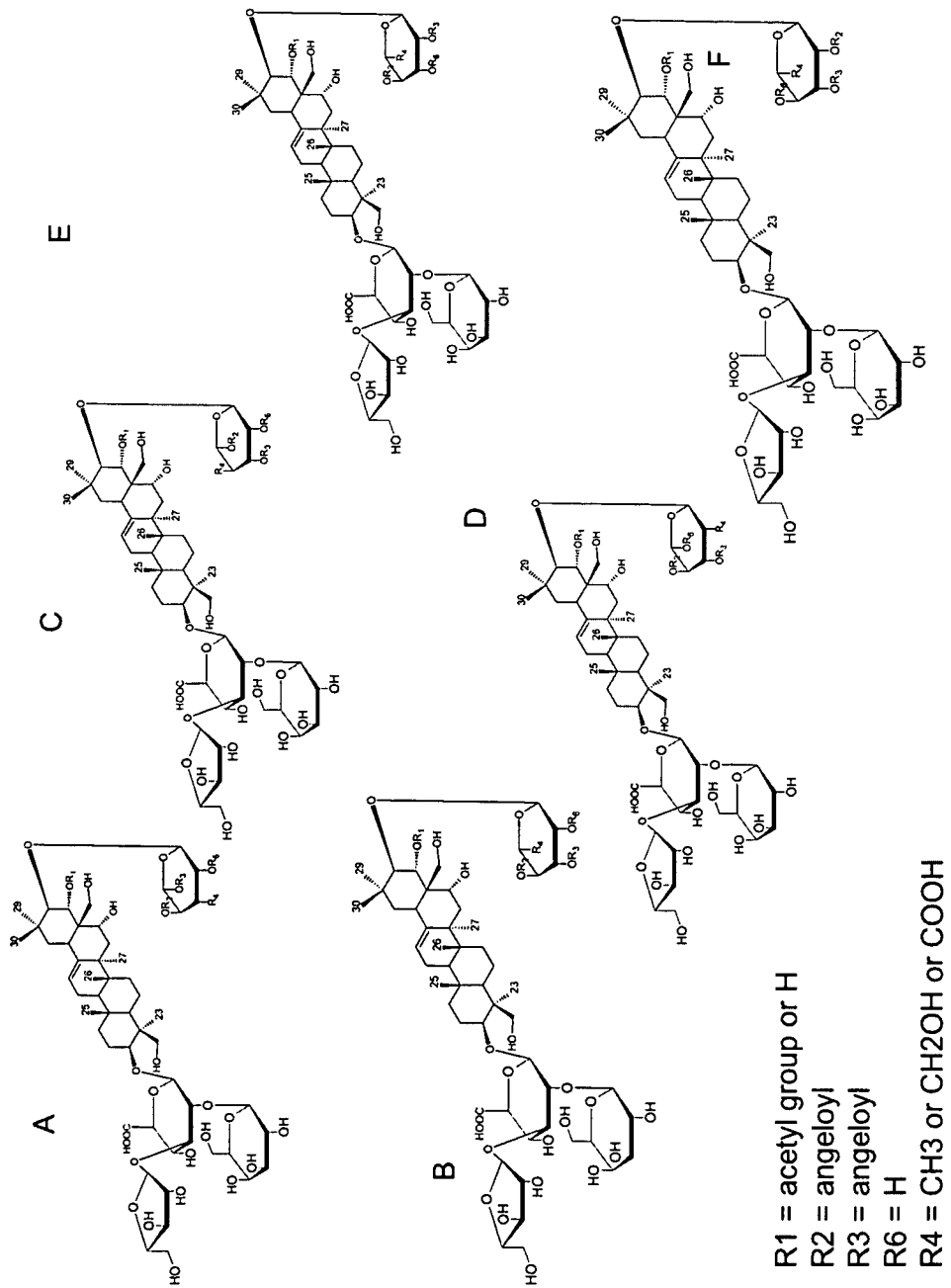
Figure 21:
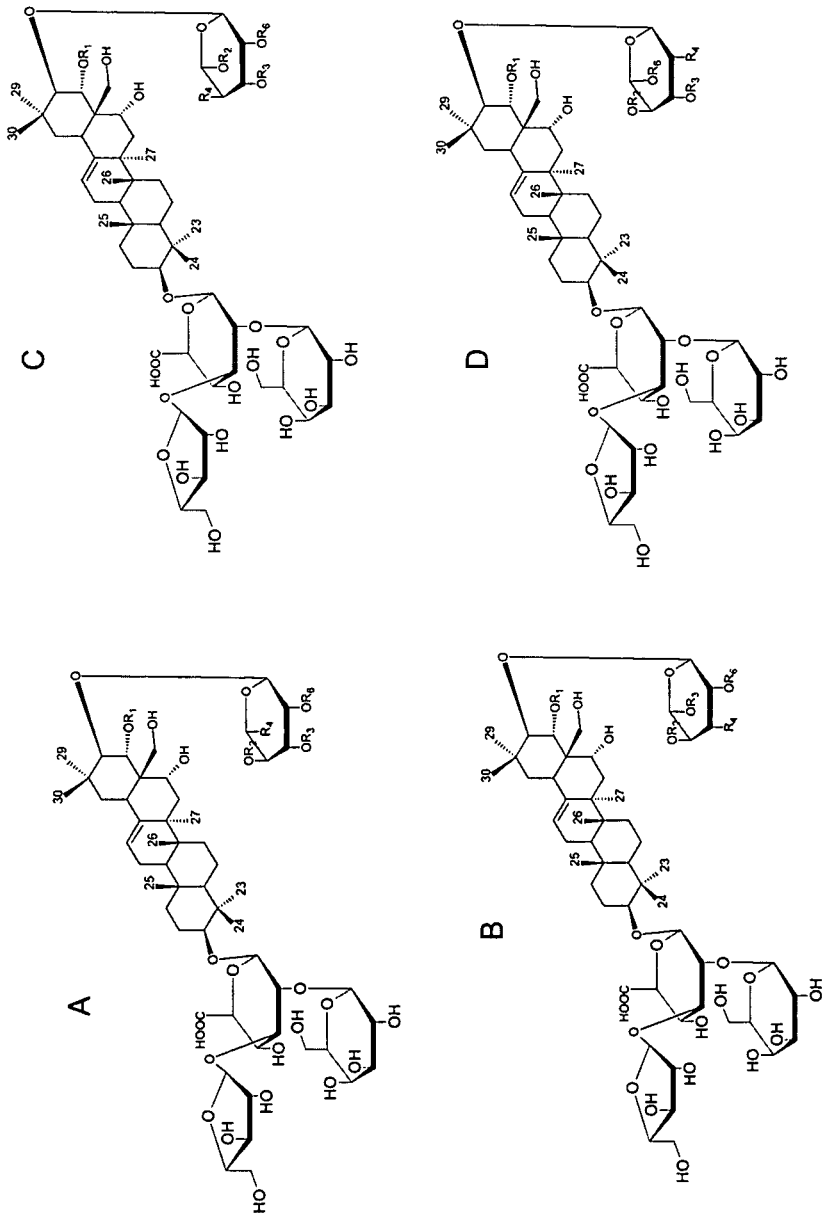
Figure 22:
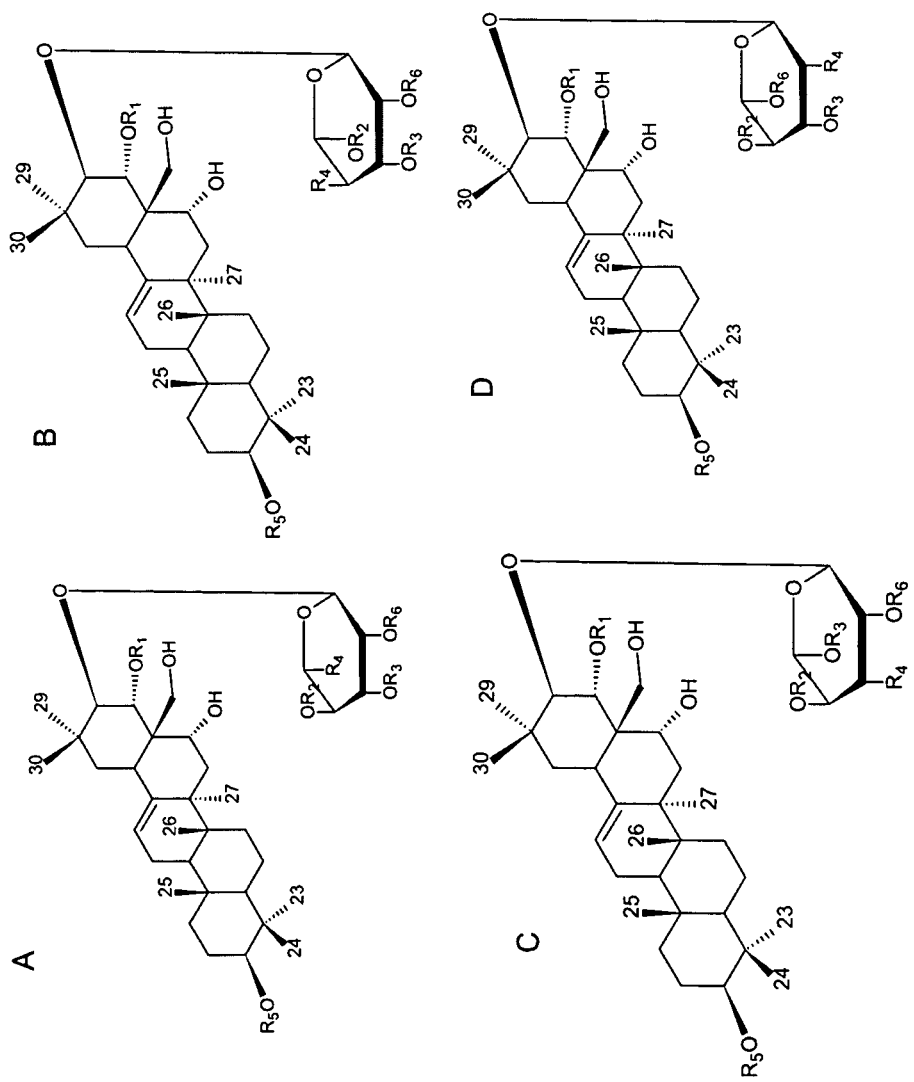
Figure 23:
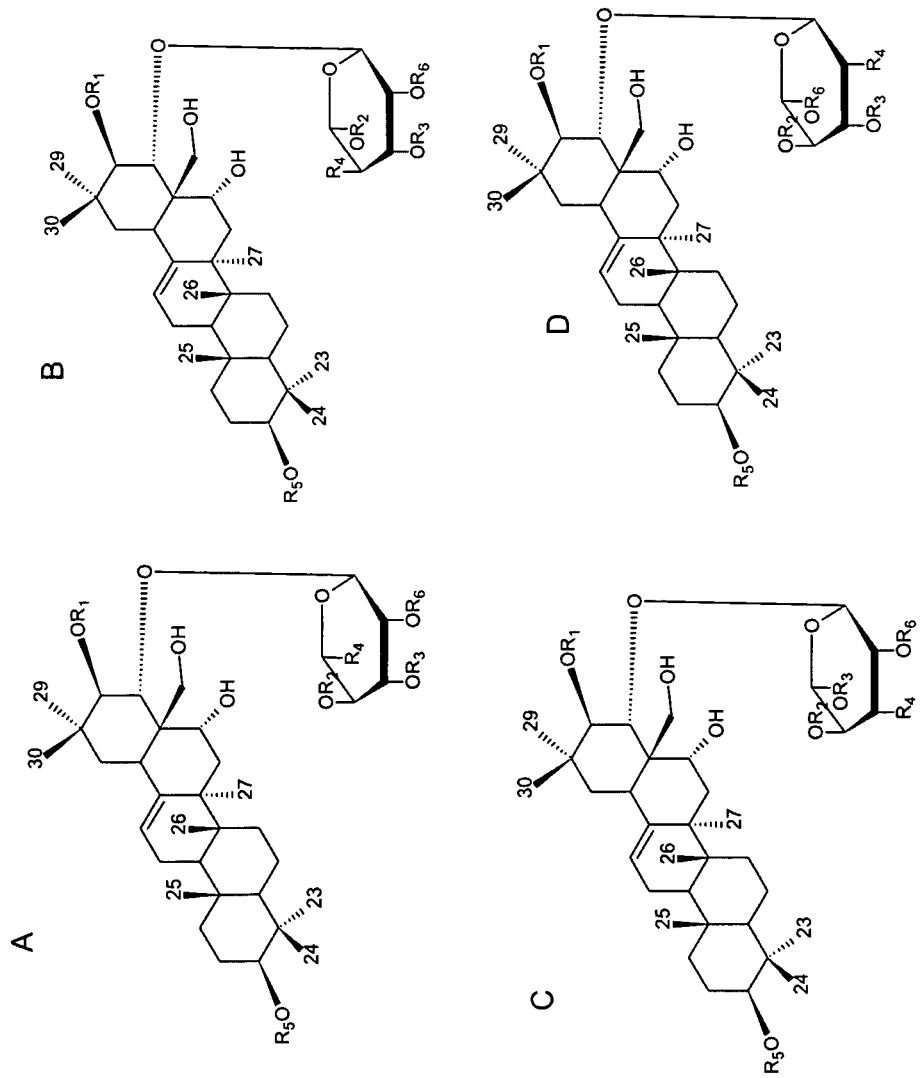
Figure 24:
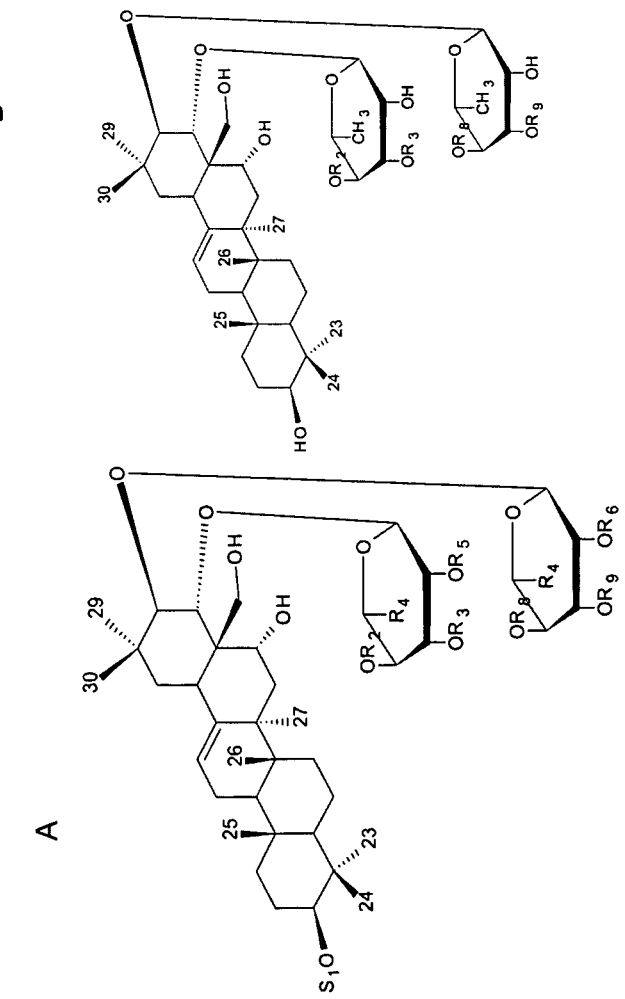
Figure 25:
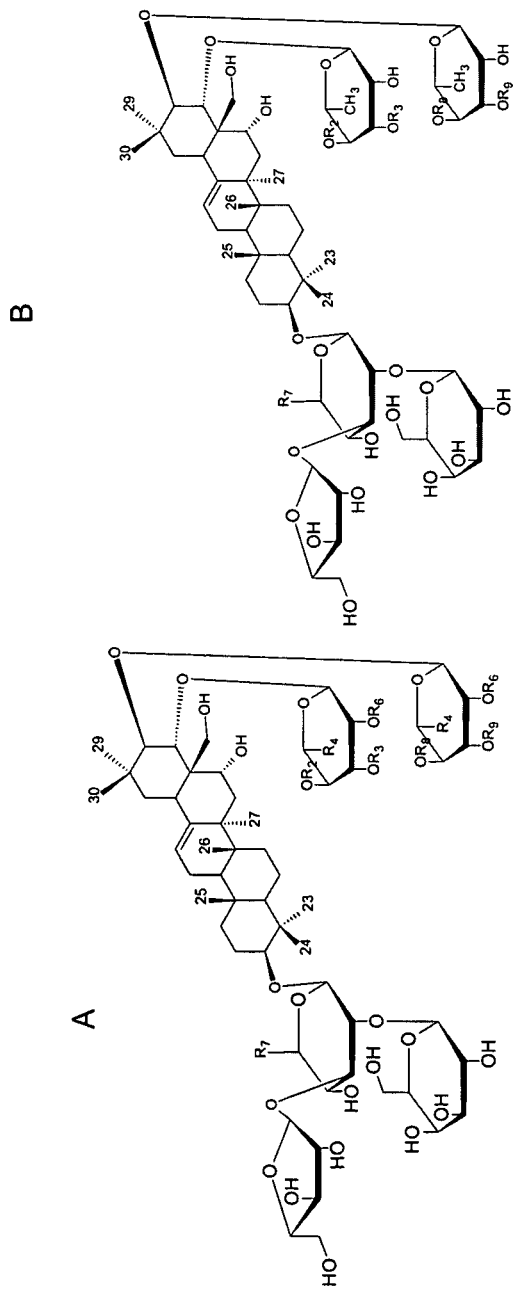
Figure 26:
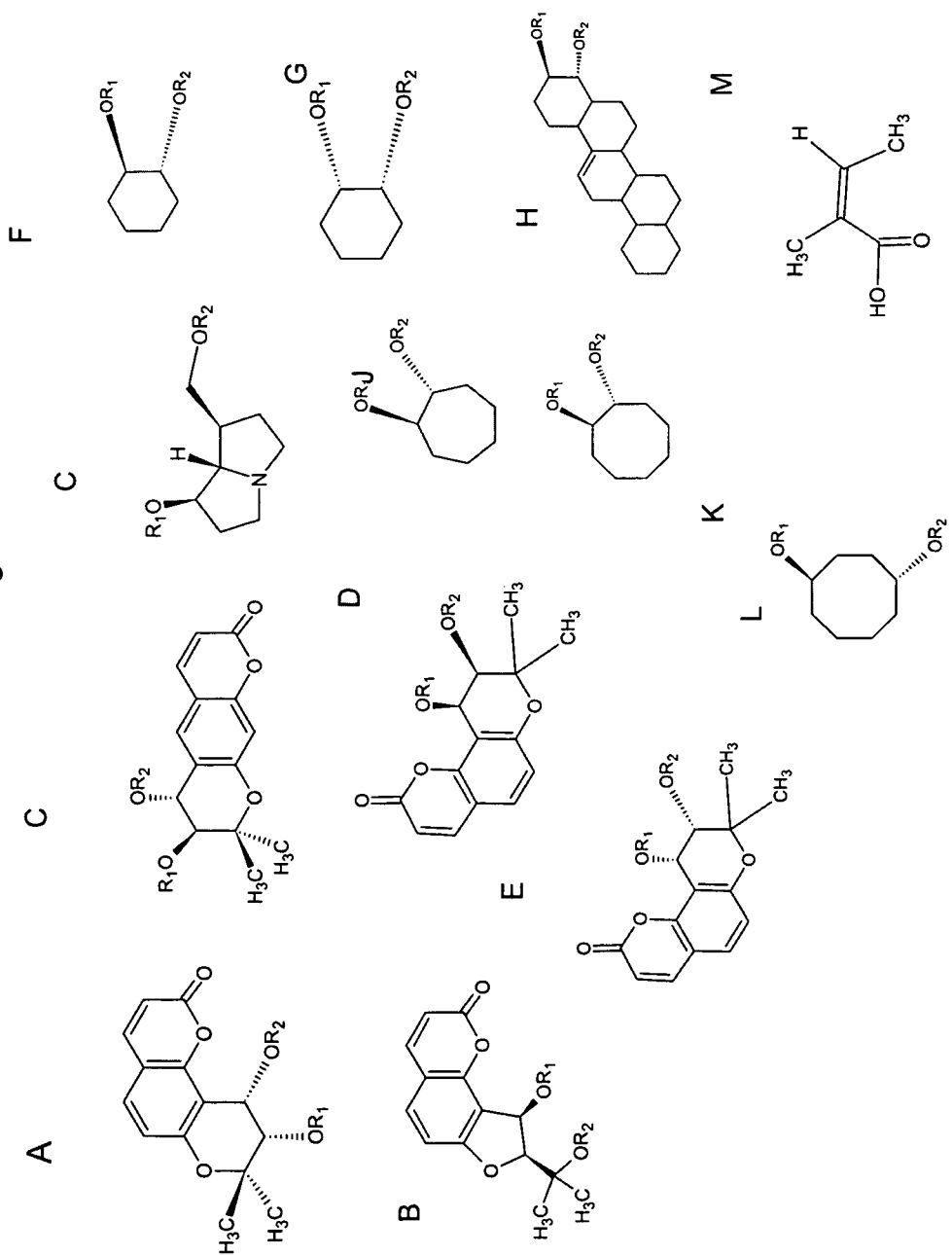
Figure 27:
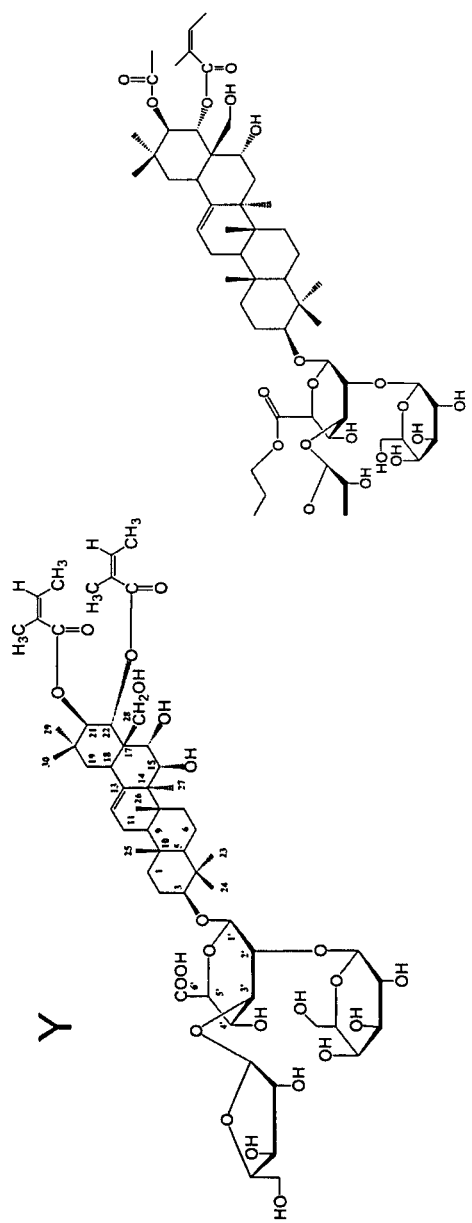

See structure of compounds in FIG. 17.

Figure 13:
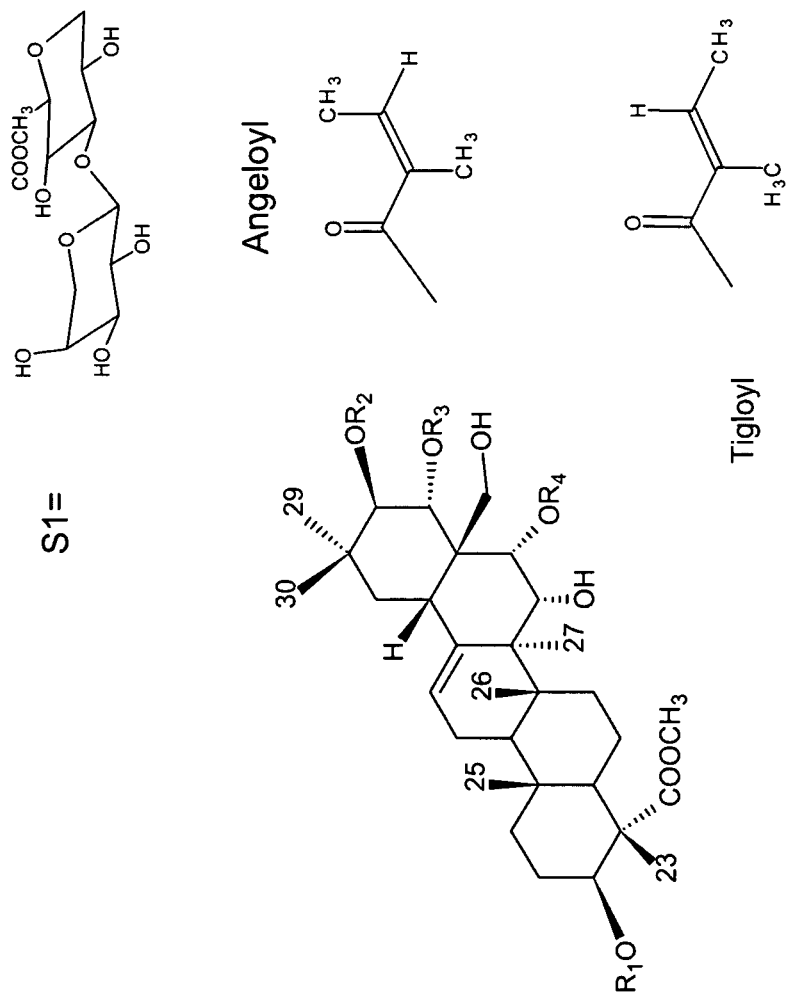

Triterpenoid saponins isolated from roots of *Camellia sinensis* var. *assamica*, showed in FIG. 13 with the characteristic structure mentioned in this invention is effective in inhibiting or reducing cancer growth. The cancer includes but is not limited to bladder cancer, bone cancer, skin cancer and ovarian cancer.

This invention provides a composition comprising the above described compounds and their derivatives for inhibiting human immunodeficiency virus (HIV), Severe Acute Respiratory Syndrome (SARS), flu disease or inhibits virus activities. See also Phytochemistry 53 (2000) 941-946 Triterpenoid saponins from the roots of tea plant (*Camellia sinensis* var. *assamica*).

Triterpenoid saponins isolated from *Pittosporum viridiflorum* with the characteristic structure mentioned in this invention can be used to reduce or inhibit cancer growth. The cancer includes but is not limited to bladder cancer, bone cancer, skin cancer and ovarian cancer. This invention also provides a composition comprising the above described compounds or their derivatives capable of inhibiting human immunodeficiency virus (HIV), Severe Acute Respiratory Syndrome (SARS) or flu disease, or capable of inhibiting viral activities.

Figure 9:
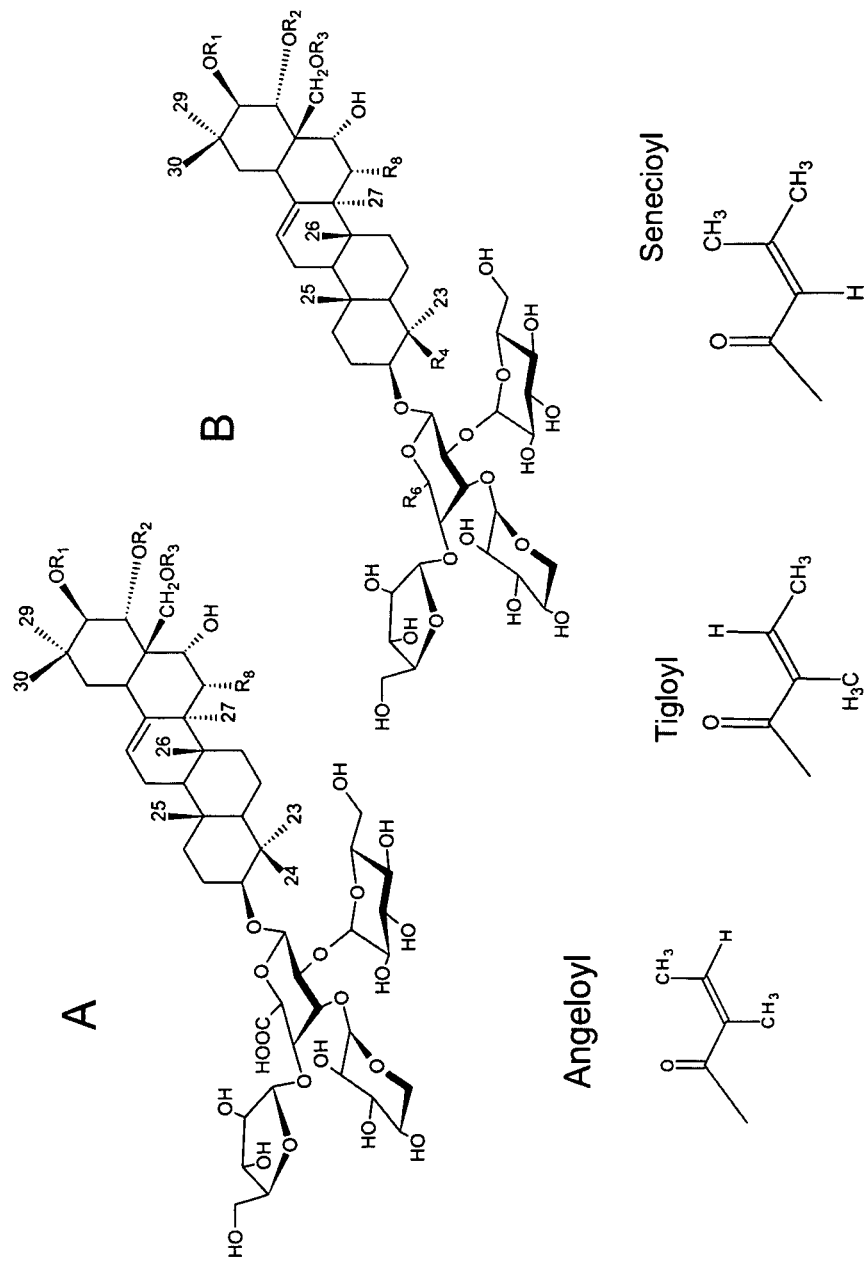

See structure of compounds in FIGS. 9 A and 9B.
Wherein R1=angeloyl group.
R2=senecioyl group.
See also 3: J. Nat. Prod. 2002, 65, 65-68. A New Triterpene Saponin from *Pittosporum viridiflorum* from Madagascar Rainforest.

The triterpenoid saponins isolated from *Pittosporum tobira* with the characteristic structure mentioned in this invention can be used for anti-cancer therapy. The cancer includes but is not limited to bladder cancer, bone cancer and ovary cancer. This invention also provides a composition comprising the above described compounds and their derivatives capable of inhibiting human immunodeficiency virus (HIV), Severe Acute Respiratory Syndrome (SARS) or flu disease, or capable of inhibiting viral activities.

Figure 10:
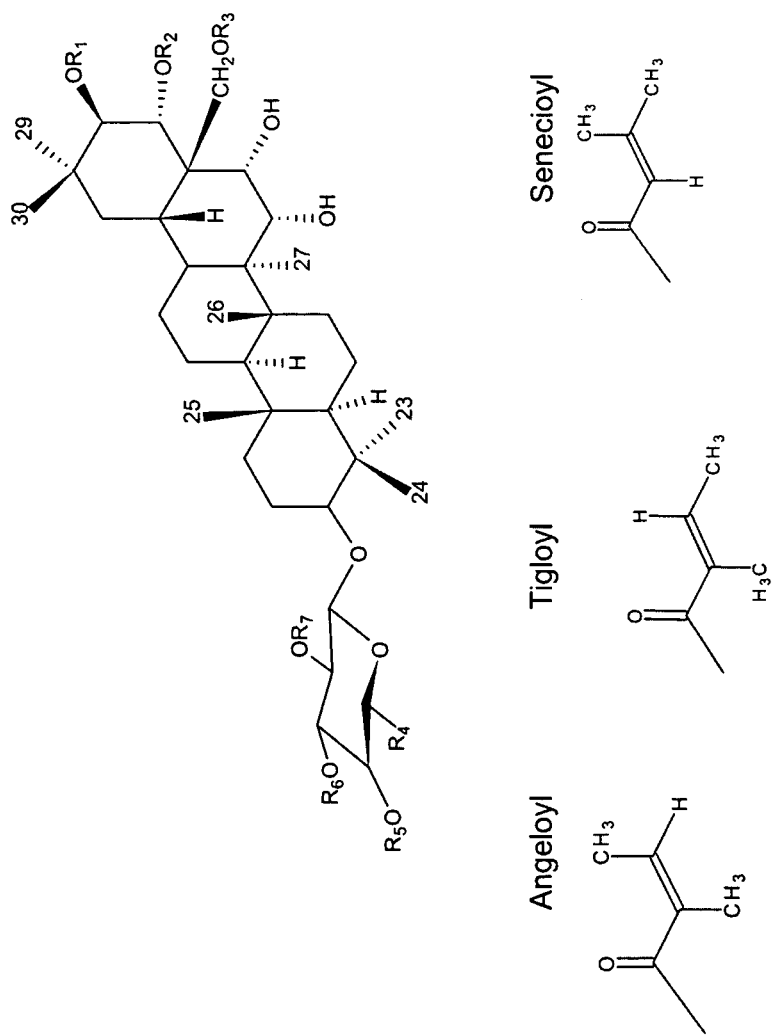

See structure of compounds in FIG. 10.
Wherein

| | R1 | R2 | R3 | R4 |
|---|---|---|---|---|
| 1. | 2-acetoxy-2-methybutanoyl | acetyl | H | COOH |
| 2. | Angeloyl | acetyl | H | COOH |
| 3. | Angeloyl | H | acetyl | COOH |
| 4. | Angeloyl | angeloyl | H | COOH |
| 5. | H | H | H | COOH |
| 7. | H | H | H | COOMe |
| 8. | H | H | H | $CH_2OH$ |

R5 = α-L-araf
R6 = α-L-arap
R7 = β-D-glup

See also Tetrahedron 58 (2002)10127-10136. Isolation and structure elucidation of four new triterpenoid ester saponins from fruit of *Pittosporum tobira* AIT.

The triterpenoid saponins isolated from *Maesa lanceolata* with the characterized structure mentioned in this invention can be used to reduce or inhibit cancer growth.

The cancer includes but is not limited to bladder cancer, bone cancer and ovarian cancer. This invention also provides a composition comprising the above described compounds or their derivatives capable of inhibiting human immunodeficiency virus (HIV), Severe Acute Respiratory Syndrome (SARS) or flu disease, or capable of inhibiting viral activities.

Figure 14:
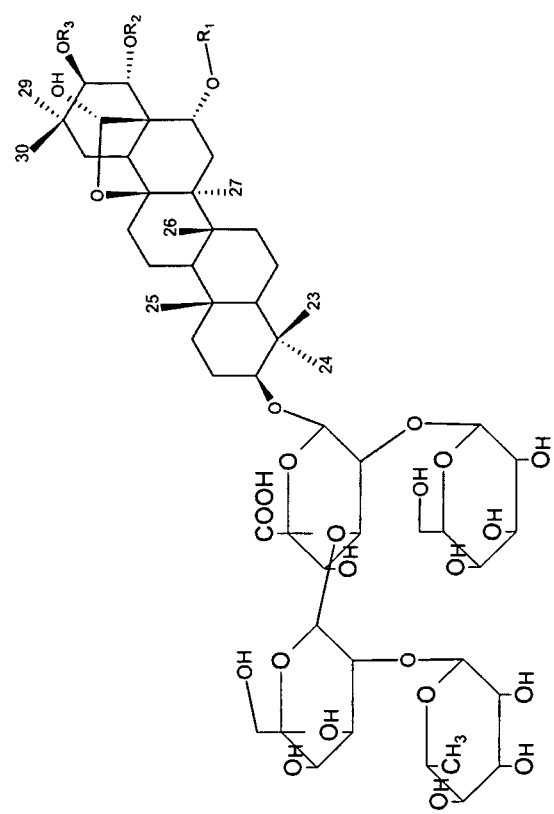

See structure of compounds in FIG. 14.
Wherein:

| compound | R1 | R2 | R3 |
|---|---|---|---|
| 2 | acetyl | H | angeloyl |
| 3 | H | acetyl | angeloyl |
| 5 | H | propanoyl | angeloyl |
| 7 | H | butanoyl | angeloyl |
| 8 | H | angeloyl | angeloyl |
| 4 | acetyl | acetyl | angeloyl |
| 6 | acetyl | propanoyl | angeloyl |
| 9 | acetyl | butanoyl | angeloyl |
| 10 | acetyl | angeloyl | angeloyl |

See also Phytochemistry 52 (1999)1121-1131. New acylated triterpenoid saponins from *Maesa lanceolata*.

The triterpenoid saponins isolated from *Xanthoceras sobifolia* with the characteristic structure mentioned in this invention can be used to reduce or inhibit cancer growth. The cancer includes but is not limited to bladder cancer, bone cancer and ovarian cancer. This invention also provides a composition comprising the above described compounds or their derivatives capable of inhibiting human immunodeficiency virus (HIV), Severe Acute Respiratory Syndrome (SARS) or flu disease, or capable of inhibiting viral activities.

See structures of saponins in FIG. 1 to FIG. 6.
See also PCT/US04/043459 and PCT/US04/043465.

This invention provides a method for inhibiting tumor cell growth, human immunodeficiency virus (HIV), Severe Acute Respiratory Syndrome (SARS) or flu disease, or capable of inhibiting viral activities, comprising contacting an effective amount of the compounds in FIG. 1 to FIG. 27. In an embodiment, the above described compound comprising at least two angeloyl groups at carbon 21, 22 and 28. In an embodiment, the above described compound comprising at least two angeloyl groups, tigloyl groups, senecioyl groups or acetyl group or their combinations.

Figure 8:
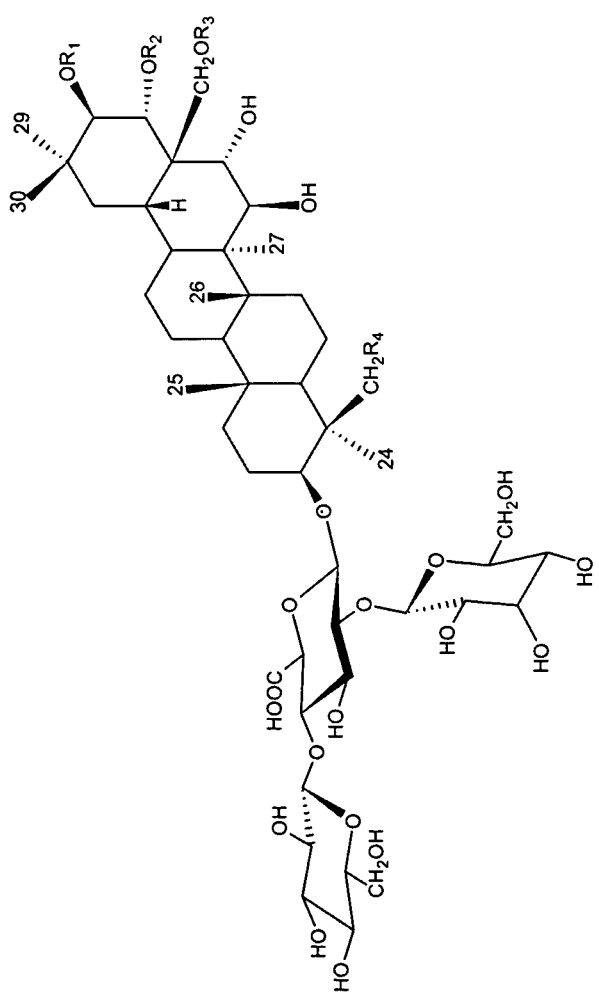
Figure 11:
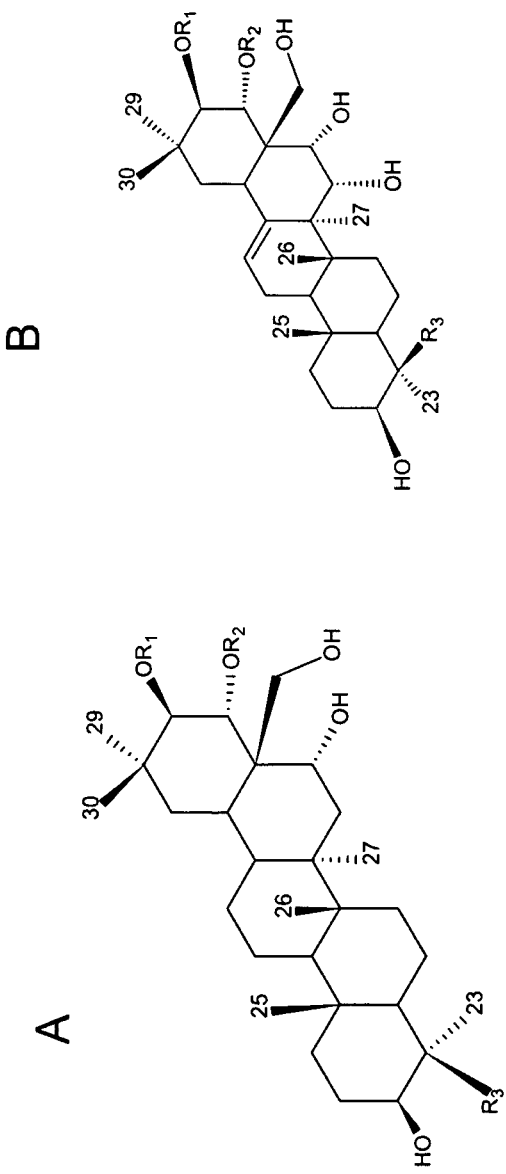
Figure 12:
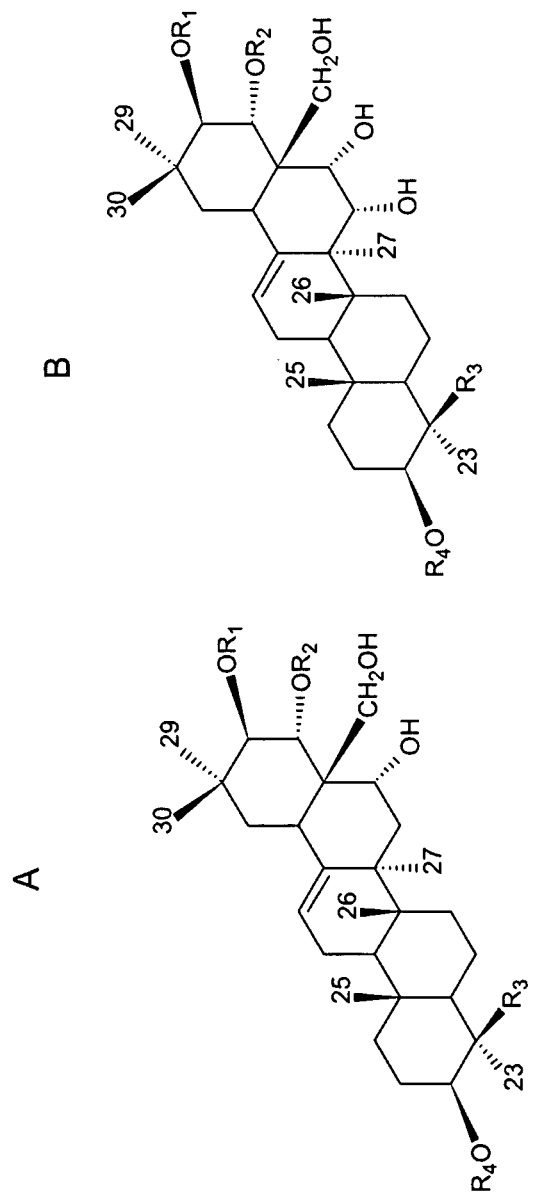

This invention provides a method for inhibiting tumor cell growth, human immunodeficiency virus (HIV), Severe Acute Respiratory Syndrome (SARS) or flu disease, or capable of inhibiting viral activities, comprising contacting an effective amount of the compounds in the FIGS. 3A and B wherein the compound comprises two angeloyl groups at any two of R1, R2 and R4; or the compounds in FIGS. 5A, 5B, 6A and 6B wherein the compound comprises two angeloyl groups at any two of R1, R2, R3 and R4; or the compounds in FIGS. 7A, 7B, 7C and 7D wherein the compound comprises two angeloyl groups at any two of R1, R2 and R3; or the compounds in FIG. 8 wherein the compound comprises two angeloyl groups at any two of R1, R2 and R3; or the compounds in FIGS. 9A, 9B and 10 wherein the compound comprises two angeloyl groups at any two of R1, R2 and R3; or the compounds in FIGS. 11, 12 and 13 wherein the compound comprises angeloyl groups at R1 and R2; or the compounds in FIG. 14 wherein the compound comprises two angeloyl groups at any two of R1, R2 and R3; or the compounds in FIG. 15 wherein the compound comprises two angeloyl groups; or the compounds in FIG. 16 wherein the compound comprises two angeloyl groups at any two of R1, R2 and R6; or the compounds in FIG. 16-25 wherein the compound comprises two angeloyl groups.

This invention provides a method for inhibiting tumor cell growth, human immunodeficiency virus (HIV), Severe Acute Respiratory Syndrome (SARS) or flu disease, or capable of inhibiting viral activities, comprising contacting an effective amount of the above described compounds. In an embodiment, the compound is a triterpenoidal saponin or a sapongenin comprising two angeloyl groups attached to carbon 21 and 22 of its sapogenin. In an embodiment, the sapongenin comprising any two of angeloyl groups, tigloyl groups or senecioyl groups, or their combinations thereof attached to carbon 21 and 22 of its sapogenin. In another embodiment, the compound is a triterpenoidal saponin or a sapongenin comprising any two of angeloyl groups, tigeloyl groups or senecioyl groups, or their combinations thereof attached to a sugar moiety which bonds to carbon 21 or 22.

In a further embodiment, the compound is a triterpenoidal saponin or sapongenin comprising at least any one of angeloyl group, tigloyl group, or senecioyl group, or their combinations thereof attached to carbon 21 and/or 22 of its sapogenin. In a further embodiment, the compound is a triterpenoidal saponin or a sapongenin comprising at least two of angeloyl group or tigloyl group or senecioyl group, or their combinations thereof attached to a sugar moiety which bonds to carbon 21 or 22.

In an embodiment, the compound is a triterpenoidal saponin or a sapongenin comprising at least two angeloyl groups attached to carbon 21, 22 or 28 of its sapogenin. In another embodiment, the compound is a triterpenoidal saponin or a sapongenin comprising any two of angeloyl groups, tigeloyl groups or senecioyl groups, or their combinations thereof attached to a sugar moiety which bonds to carbon 21, 22 or 28. In an embodiment, the compound is a triterpenoidal saponin or a sapongenin comprising a sugar moiety comprises at least two angeloyl groups attached to carbon 21, 22 or 28 of its sapogenin.

In a further embodiment, the compound is a five ring triterpene comprising at least two angeloyl group, attached to the side chains at one end of the five rings of its sapogenin and a sugar moiety is attached to the side chains of the ring at the other end of the triterpene. In an embodiment the compound comprising at least any two of angeloyl group, tigloyl group, or senecioyl group, or their combinations thereof.

In a further embodiment, the compound is a sapogenin or triterpene comprising at least two angeloyl group, attached to the side chains of its sapogenin and a sugar moiety is attached to the side chains of the triterpene or sapogenin. In an embodiment the compound comprising at least any two of angeloyl group, tigloyl group, or senecioyl group, or their combinations thereof.

In a further embodiment, the compound comprises at least two angeloyl group, attached to the side chains of a compound and a sugar moiety is attached to a side chain of the compound. In an embodiment the compound comprising at least any two of angeloyl group, tigloyl group, or senecioyl group, or their combinations thereof. In an embodiment, the angeloyl can be replaced by a function group which has the function as angeloyl group.

In a further embodiment, a sugar moiety or chain with one or more sugar such as D-glucose, D-galactose, L-rhamnose, L-arabinose, D-xylose, alduronic acid, D-glucuronic acid or D-galacturonic acid, or their combinations thereof, or their derivatives thereof is attached to carbon 3.

In a further embodiment, the compound is a triterpene or sapongenin comprising at least any one of angeloyl group, tigloyl group or senecioyl group, or their combinations thereof attached to it. In a further embodiment, the compound is a triterpene or sapongenin comprising at least one of angeloyl group, tigloyl group or senecioyl group, or their combinations thereof attached to a sugar moiety which bonds to it.

In a further embodiment, at least one sugar moiety with one or more sugar, D-glucose, D-galactose, L-rhamnose, L-arabinose, D-xylose, or alduronic acid, D-glucuronic acid or D-galacturonic acid, or their combinations thereof, or their derivatives thereof is attached to the triterpene. In a further embodiment, bonds 23-30 are attached with CH3 or CH2OH or COOH or acetyl group.

The activities of a saponin compound for regulating or inhibiting tumor cell growth are based on or attributed to its structure that comprises functional group(s) such as angeloyl group, tigloyl group, senecioyl group or acetyl group, or their combinations thereof.

Figure 29:
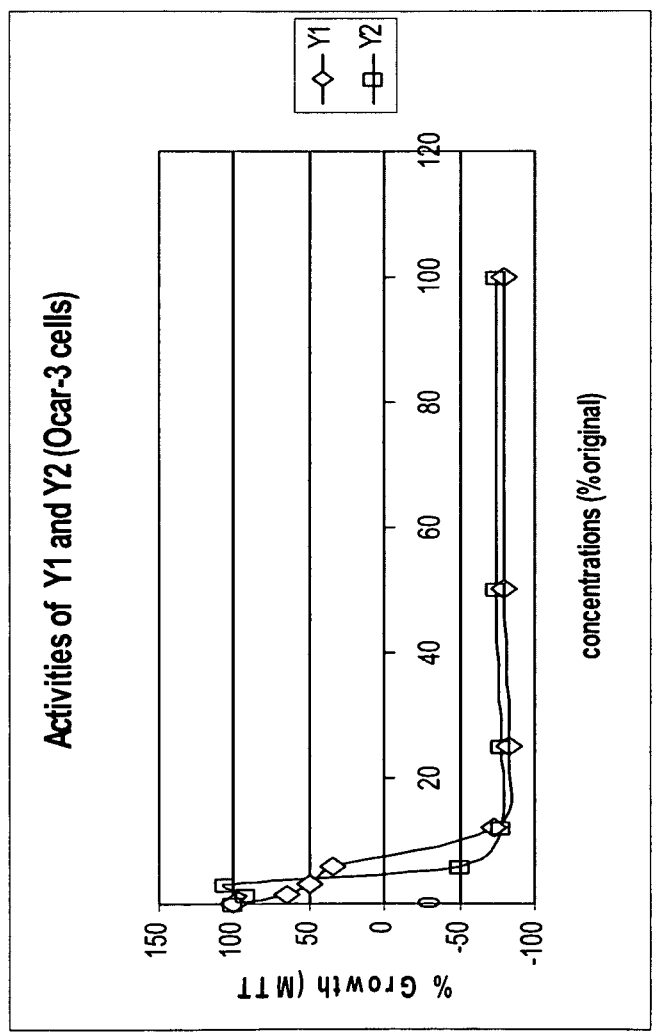
FIG. 29 shows the inhibition of the purified Compound Y1 and Compound Y2 on the growth of ovarian cancer cells.

The Compound Y1 and Compound Y2 which comprise with two angeloyl groups show the inhibition on the growth of ovarian cancer cells. See FIG. 29.

Figure 30:
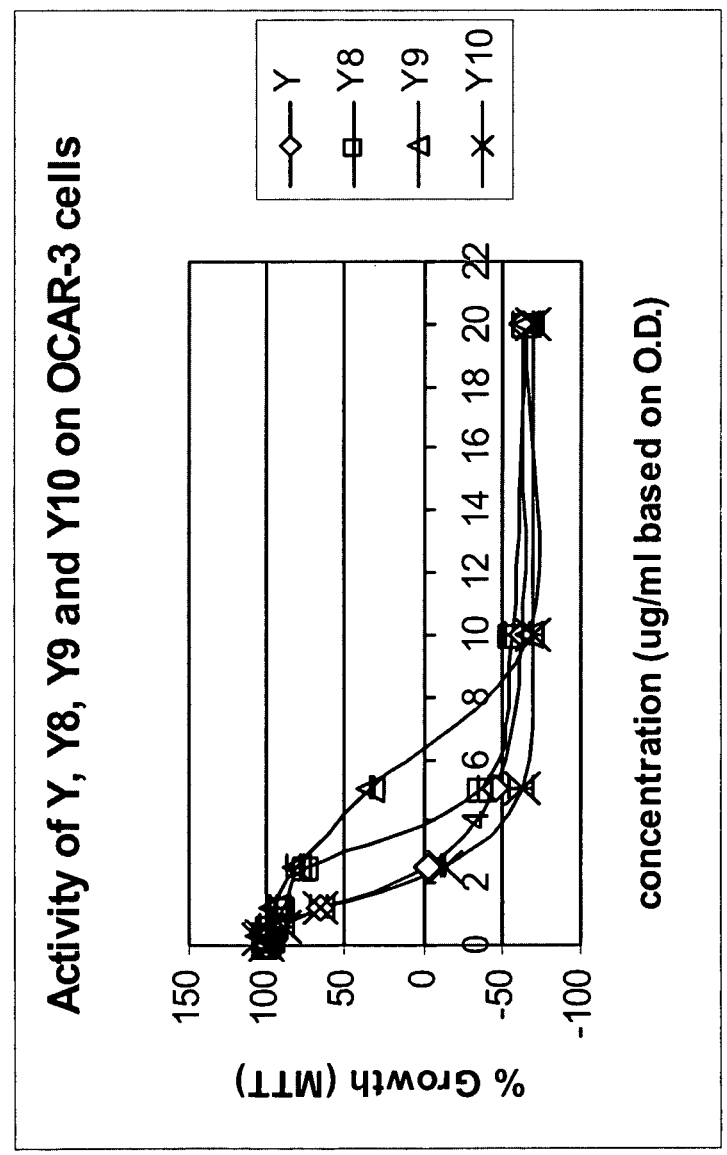
FIG. 30 shows the anticancer activity of Y, Y8, Y9 and Y10 on ovarian cancer cells as determined by MTT assay.
Figure 31:
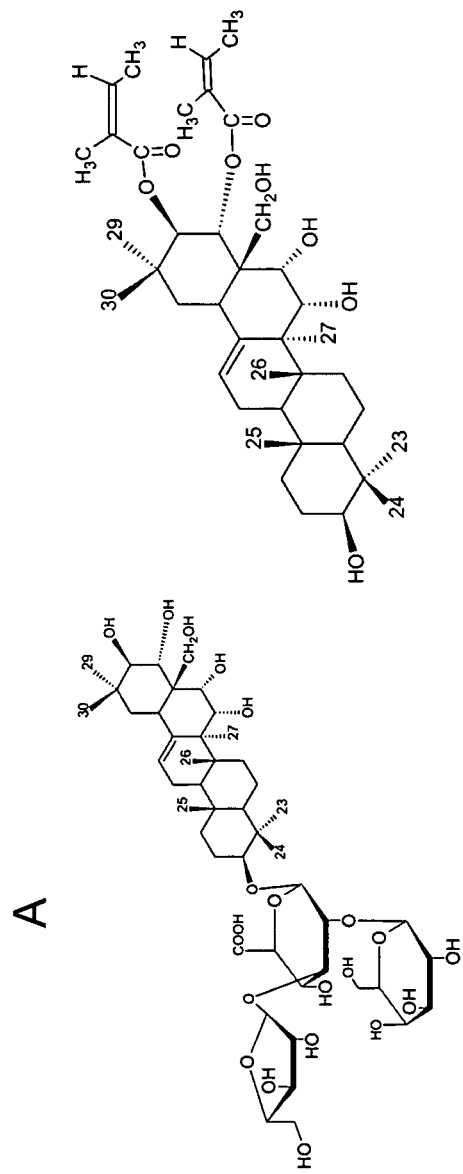
FIG. 31 (A) shows a compound of the invention without angeloyl groups. (B) shows a compound of the invention without sugar moiety.
Figure 32:
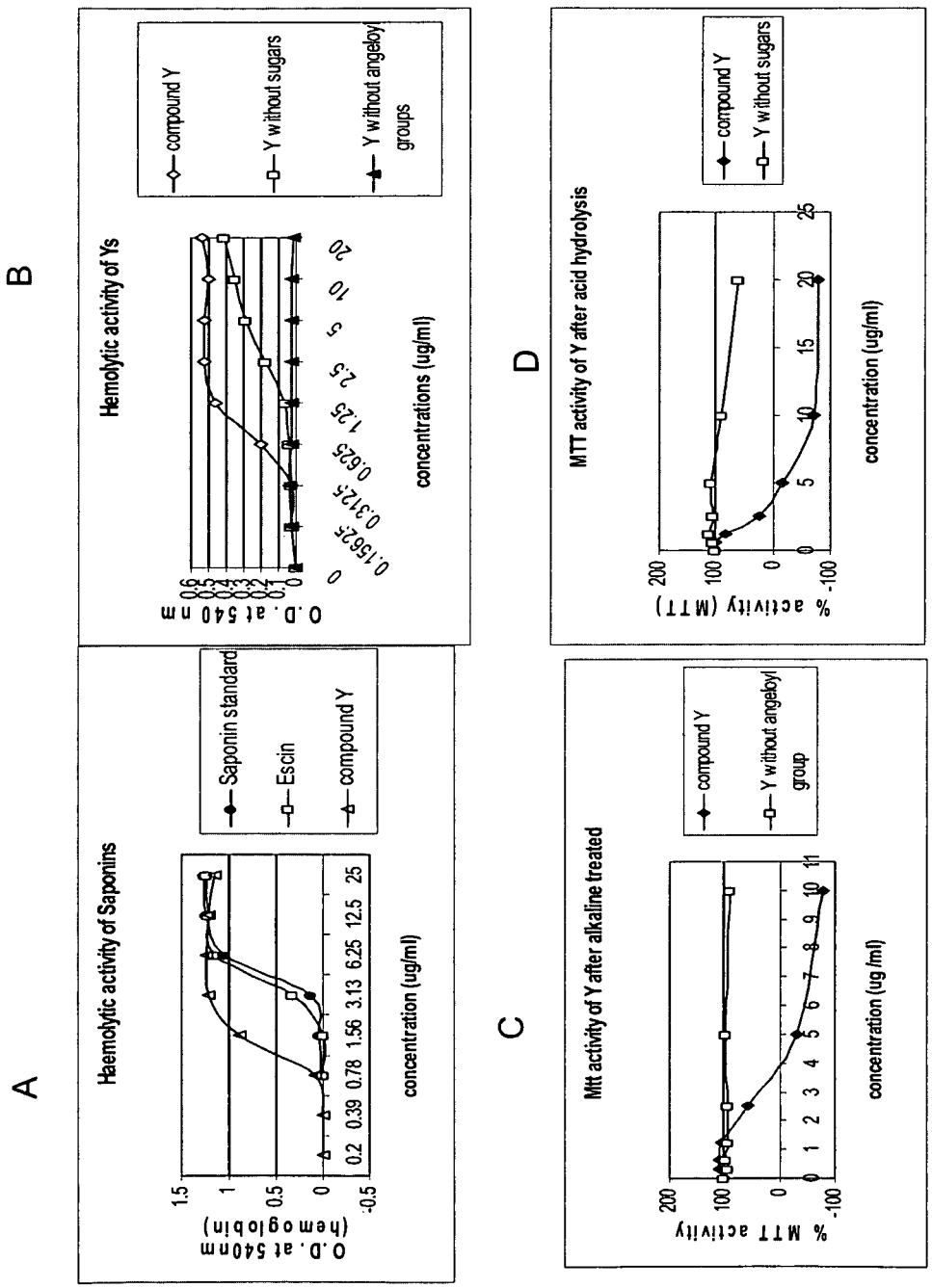
FIG. 32 shows a comparison of MTT and Haemolytic activities of saponin compound and Compound Ys of the invention. (A) and (B) shows hemolytic activities. (C) and (D) show MTT activities.

The Compound Y, Y8, Y9 and Y10 which comprise with two angeloyl groups show the inhibition on ovarian cancer cells as determined by MTT assay. See FIG. 30.

Figure 28:
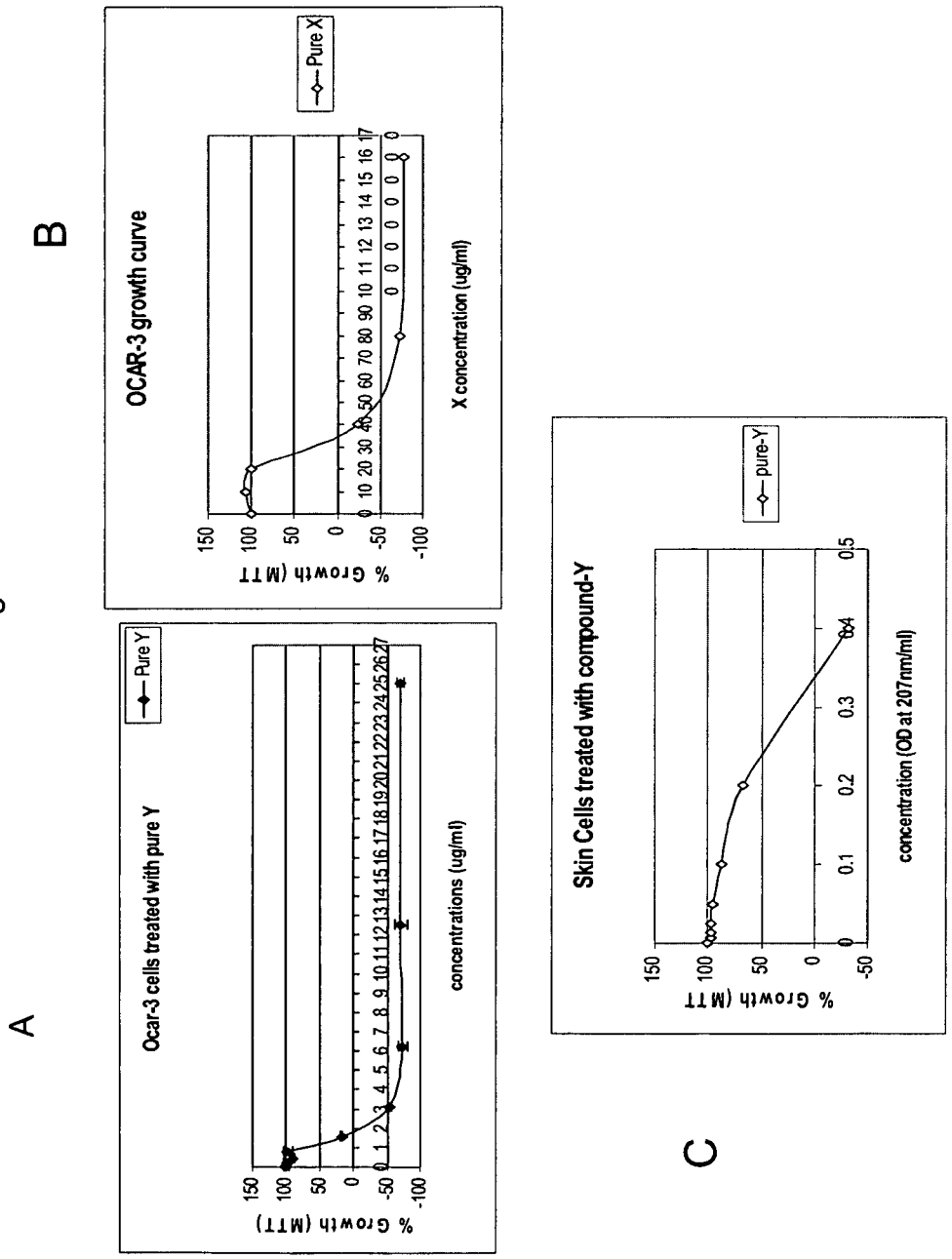

The compound with single angeloyl group shows weaker anticancer activity than a compound with two angeloyl groups. See FIG. 28.

The compound with two angeloyl groups is more potency than the one with on angeloyl for inhibiting human immunodeficiency virus (HIV), Severe Acute Respiratory Syndrome (SARS), flu disease or inhibits virus activities.

This invention provides a composition comprising the compounds comprises the structure of:

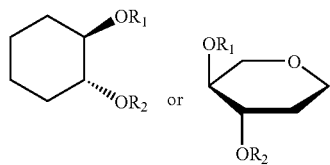

wherein R1 and R2 are angeloyl group. In embodiment, R1 and R2 are angeloyl groups, tigloyl groups, senecioyl groups or acetyl group or their combinations. In embodiment, R1 and R2 comprise compound selected from angeloyl, acetyl, tigloyl, senecioyl, alkyl, benzoyl, dibenzoyl, alkanoyl, alkenoyl, benzoyl alkyl substituted alkanoyl, aryl, heterocyclic or heteroraryl or derivative thereof.

The above compounds can be used for inhibiting tumor cell growth, human immunodeficiency virus (HIV), Severe Acute Respiratory Syndrome (SARS) or flu disease, or capable of inhibiting viral activities, comprising contacting an effective amount of the above described compounds.

This invention provides a method of inhibiting the growth of ovarian cancer, breast cancer, brain cancer, bladder cancer, prostate cancer, bone cancer, skin cancer, leukocyte cancer, liver cancer or leukemia in a subject, comprising administering to a subject, in need thereof, an effective amount of the compound which comprises any of the above structures to said subject.

This invention provides a method for inhibiting tumor cell growth, regulating cell growth, reducing inflammation, in a subject, comprising administering to a subject, in need thereof, an effective amount of the compound which comprises any of the above structures to said subject.

This invention provides a method for reducing leg swelling, reducing the symptom of chronic venous insufficiency, peripheral edema, antilipemic, chronic venous disease, varicose vein disease, varicose syndrome, venous stasis, Expectorant, peripheral vascular disorders, cerebro-organic convulsion, cerebral circulation disorder, cerebral edema, psychoses, dysmenorrheal, hemorrhoids, episiotomies, haemonhoids, peripheral oedema formation or postoperative swelling; for reducing symptoms of leg pain; for treating pruritis, lower leg volume, for reducing symptoms of pain; thrombosis, thromophlebitis; for preventing gastric ulcers antispasmotic comprising administering to a subject, in need thereof, an effective amount of the composition of this invention.

This invention provides a composition comprising the compounds of the invention for treating enuresis and frequency micturition, and for improving the functions of the central nervous system including signaling the bladder to wake up from deep sleep or to relax the bladder so that it can store more urine. The compounds of the invention can be used to relax the detrusor tension caused by aging, stress, nervousness, over-activity, instability, hyper-reflexia, and uninhibited bladder. In another embodiment, the compounds may be used for relaxing the contracted bladder tissue induced by acetylcholine (Ach). The compounds identified and isolated from extract of this invention may be used as acetylcolinesterase, an AChE inhibitor, for regulating Antidiuretic hormone (ADH), which reduces the volume of urine, and as an anti-inflammatory agent.

The compounds of the invention can be used for accelerating the growth of bladder, for suppressing deep sleep, for increasing alertness in a sleeping subject, for modulating the release, breakdown and uptake of Antidieuretic hormone (ADH) and its receptors, for modulating the secretion, breakdown and uptake of Adrenocorticotropic hormone (ACTH) and its receptors, for modulating the release, breakdown and uptake of 5-hydroxytryptamine and its receptors, for modulating the release, breakdown and uptake of Acetylcholine (Ach) and its receptors, for modulating the release, breakdown and uptake of Adrenaline (AD) and its receptors, for modulating the release, breakdown and uptake of Dopamine (DA) and its receptors, for modulating the release, breakdown and uptake of Norepinephrine (NE) and its receptors, for preventing sleep paralysis, for modulating the formation, release, breakdown and activity of neuropeptides and their receptors.

This invention provides a composition comprising the compounds of the invention for treating cancers; for inhibiting virus; for preventing cerebral aging; for improving memory; improving cerebral functions, for curing enuresis, frequent micturition, urinary incontinence, dementia, Alzheimer's disease, autism, brain trauma, Parkinson's disease or other diseases caused by cerebral dysfunctions; for treating arthritis, rheumatism, poor circulation, arteriosclerosis, Raynaud's syndrome, angina pectoris, cardiac disorder, coronary heart disease, headache, dizziness, kidney disorder; cerebrovascular disease; inhibiting NF-Kappa B activation; for treating brain edema, sever acute respiratory syndrome, respiratory viral diseases, chronic venous insufficiency, hypertension, chronic venous disease, anti-oedematous, anti inflammatory, haemonhoids, peripheral oedema formation, varicose vein disease, flu, post traumatic edema and postoperative swelling; for inhibiting ethanol absorption; for lowering blood sugar; for regulating the adrenocorticotropin and corticosterone level; and for treating impotence or premature ejaculation or diabetes. See U.S. Ser. No. 10/906,303, filed Feb. 14, 2005, International Application No. PCT/US04/43465, filed Dec. 23, 2004, International Application No.

PCT/US04/33359, filed Oct. 8, 2004, and U.S. Ser. No. 11/131,551, filed May 17, 2005, the contents of which are incorporated herein by reference.

This invention provides a composition for treating chronic venous insufficiency, peripheral edema, antilipemic, chronic venous disease, varicose vein disease, varicose syndrome, venous stasis, Expectorant, peripheral vascular disorders, cerebro-organic convulsion, cerebral circulation disorder, cerebral edema, psychoses, dysmenorrheal, hemorrhoids, episiotomies, haemonhoids, peripheral oedema formation or postoperative swelling; for reducing symptoms of pain; for reducing symptoms of stomach pain; for reducing symptoms of leg pain; for treating pruritis, lower leg volume, thrombosis, thromophlebitis; for preventing gastric ulcers antispasmotic.

This invention provides a composition for AntiMS, antianeurysm, antiasthmatic, antibradykinic, anticapillarihemorrhagic, anticephalagic, anticervicobrachialgic, antieclamptic, antiedemic, antiencaphalitic, antiepiglottitic, antiexudative, antiflu, antifracture, antigingivitic, antihematomic, antiherpetic, antihistaminic, antihydrathritic, antimeningitic, antioxidant, antiperiodontic, antiphlebitic, antipleuritic, antiraucedo, antirhinitic, antitonsilitic, antiulcer, antivaricose, antivertiginous, cancerostatic, corticosterogenic, diuretic, fungicide, hemolytic, hyaluronidase inhibitor, lymphagogue, natriuretic, pesticide, pituitary stimulant, thymolytic, vasoprotective, venotonic treatment, In an embodiment, an angeloyl group combined with a coumarin shows strong anti-tumor activities.

This invention provides a compound capable of reducing or inhibiting cancer cell growth, comprising the following structure:

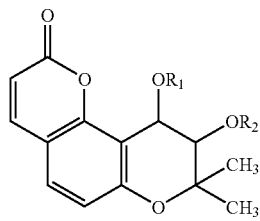

Wherein the R1, R2=Angeloyl, or tigloyl, or senecioyl, or acetyl group.

If the Angeloyl or tigloyl or senecioyl or acetyl in the above compound is replaced with hydroxyl group, the anti-tumor activities will be lost. The replacement of Angeloyl group with tigloyl group also reduces the anti-tumor activities. If we replace the acetyl group with Angeloyl group, the anti-tumor activities is increased.

In an embodiment, Angeloyl group combined with a coumarin shows activities. The structure is shown below:

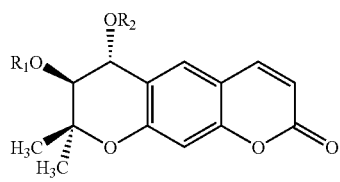

Wherein the R1, R2=Angeloyl or tigloyl or senecioyl or acetyl group.

The structure of the active compounds isolated from *Angelica edulis Miyabe* is shown below:

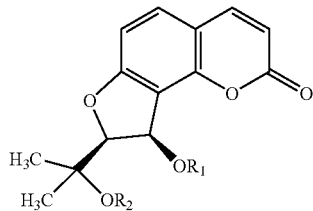

Wherein the R1, R2=Angeloyl or tigloyl or senecioyl or actyl group.

The above described compounds can be used for inhibiting cancer, wherein the cancer is not limited to breast cancer, leukocyte cancer, liver cancer, ovarian cancer, bladder cancer, prostate cancer, bone cancer, skin cancer, lung cancer, brain cancer, cervix cancer, KB cancer or brain cancer.

A sugar moiety is a segment of molecule comprising one or more sugar group.

Alkenyl means, unsaturated linear or branched structures and combinations thereof, having 1-7 carbon atoms, one or more double bonds therein. Non-limiting examples alkenyl groups include vinyl, propenyl, isopropenyl, butenyl, s- and t-butenyl, pentenyl, hexenyl, butadienyl, pentadienyl, hexadienyl.

An aryl is a functional group of organic molecule derived from an aromatic compound such as benzene, a 6-14 membered carbocyclic aromatic ring system comprising 1-3 benzene ring s. If two or more aromatic rings are present, then the rings are fused together, so that adjacent rings share a common bond. Examples include phenyl and naphthyl. The aryl group may be substituted with one or more substitutes independently selected from halogen, alkyl or alkoxy.

Acyl is a function group obtained from an organic acid by the removal of the carboxyl. Acyl groups can be written as having the general formula —COR, where there is a double bond between the carbon and oxygen. The names of acyl groups typically end in -yl, such as formyl, acetyl, propionyl, butyryl, benzoyl.

Benzoyl is one of acyls, C6H5.COR, obtained from benzoic acid by the removal of the carboxyl.

heterocyclic compound—a compound containing a heterocyclic ring which refers to a non-aromatic ring having 1-4 heteroatoms said ring being isolated or fused to a second ring selected from 3- to 7-membered alicyclic ring containing 0-4 heteroatoms, aryl and heteroaryl, wherein said heterocyclic include pyrrolidinyl, piperazinyl, morpholinyl, trahydrofuranyl, imidazolinyl thiomorpholinyl, and the like.

heterocyclyl groups derived from heteroarenes by removal of a hydrogen atom from any ring atom.

alkanoyl is the general name for an organic functional group R.CO—, where R represents hydrogen nor an alkyl group. Preferably alkanoyl is selected from acetyl, propionoyl, butyryl, isobutyryl, pentanoyl and hexanoyl.

Alkenoyl is alkenylcarbonyl in which alkenyl is defined above. Examples are pentenoyl(tigloyl) and hexenoyl(angeloyl).

Alkyl is a radical containing only carbon and hydrogen atoms arranged in a chain, branched, cyclic or bicyclic structure or their combinations, having 1-18 carbon atoms. Examples included but not limited to methyl, ethyl, propyl isopropyl, butyl, s- and t-butyl, pentyl, hexyl, heptyl, octyl, nonyl, undecyl, dodecyl, tridecyl, tetradecyl, pentadecyl, cyclopropyl, cyclobutyl, cyclopentyl, cyclohexyl.

EXPERIMENTAL DETAILS

Experiment 1

Herb Extraction (a) extracting powder of husks or branches or stems or leaves or kernels or roots or barks with organic solvent at ratio of 1:2 for 4-5 times for 20-35 hours each time to form an organic extract; (b) collecting the organic extract; (c) refluxing the organic extract for 2-3 times at 80° C. to form second extract; (d) removing the organic solvent from the second extract; and (e) drying and sterilizing the second extract to form the extract powder.

Experiment 2

Analysis of Extract Components by HPLC Chromatography

Methods

HPLC. A C-18 reverse phase µbondapak column (Water P/N 27324) was equilibrated with 10% acetonitrile, 0.005% Trifluoroacetic acid (equilibration solution). An extract of plants prepared using the methods described in Experiment 1 was dissolved in equilibration solution (1 mg/ml) before applying into the column. 20 ug of samples was applied into column. Elution conditions: Fractions were eluted (with flow rate 0.5 ml/min.) with acetonitrile gradient from 10% to 80% in 70 min, and then remains at 80% for 10 min. The acetonitrile concentration then decreased to 10% and remained at 10% for 25 min. The fractions were monitored at 207 nm and recorded in chart with a chart speed of 0.25 cm/min and with OD full scale of 0.128. Instruments. Waters Model 510 Solvent Delivery System; Waters 484 tunable Absorbance Detector; Waters 745/745B Data Module.

Absorbance analysis: The absorption profile of extract at various wavelengths was determined. An extract of the present invention was dissolved in 10% acetonitrile/TFA and scanned at 200-700 nm with a spectrophotometer [Spectronic Ins. Model Gene Sys2].

Results

HPLC. The peaks can be accounted for in the profile. The major peaks are labelled following increased concentration of acetonitrile elution.

Absorption maximum. Three absorption maximum were identified for plant extract; 207 nm, 278 nm and 500 nm.

Experiment 3

Determination of the Cell-Growth Activity Effected by Extract with Cancer Cells Derived from Different Human Organs Using MTT Assay Methods and Materials Cells. Human cancer cell lines were obtained from American Type Culture Collection: HTB-9 (bladder), HeLa-S3 (cervix), DU145 (prostate), H460 (lung), MCF-7 (breast), K562 (leukocytes), HCT116 (colon), HepG2 (liver), U2OS (bone), T98G (brain), Skin and OVCAR-3 (ovary). Cells were grown in culture medium (HeLa-S3, DU145, MCF-7, Hep-G2 and T98G in MEN (Earle's salts); HTB-9, H460, K562, OVCAR-3 in RPMI-1640; HCT-116, U2OS in McCoy-5A) supplemented with 10% fetal calf serum, glutamine and antibiotics in a 5% CO2 humidified incubator at 37° C.

MTT assay. The procedure for MTT assay followed the method described in (Carmichael et al., 1987) with only minor modifications. Cells were seeded into a 96-wells plate at concentrations of 10,000/well (HTB-9, HeLa, H460, HCT116, T98G, OVCAR-3), 15,000/well (DU145, MCF-7, HepG2, U2OS), or 40,000/well (K562), for 24 hours before drug-treatment. Cells were then exposed to drugs for 48 hours (72 hours for HepG2, U2OS, and 96 hours for MCF-7). After the drug-treatment, MTT (0.5 mg/ml) was added to cultures for an hour. The formation of formazan (product of the reduction of tetrazolium by viable cells) was dissolved with DMSO and the O.D. at 490 nm was measured by an ELISA reader [Dynatech. Model MR700]. The MTT level of cells before drug-treatment was also measured (T0). The % cell-growth (% G) is calculated as:

$$\% \ G = (TD-T0/TC-T0) \times 100 \quad (1)$$

where TC or TD represent O.D. readings of control or drug-treated cells. When T0>TD, then the cytotoxicity (LC) expressed as % of the control is calculated as:

$$\% \ LC = (TD-T0/T0) \times 100. \quad (2)$$

Results

Among the 11 cell lines studies, inhibition of cell-growth after exposure of plant extract was observed. However, their sensitivity toward the extract is different. The response of the cell lines to the tested extract can be categorized into four groups: Most sensitive, Sensitive; Semi-sensitive; and least sensitive.

To investigate the inhibition components of the plant extract, the plant extract was fractionated.

Experiment 4

Purification of the Inhibition Components in Plant Extract (A) Fractionation of Plant Extracts with FPLC Methods Column. Octadecyl functionalized silica gel. Column dimension: 2 cm×28 cm; equilibrated with 10% acetonitrile-0.005% TFA before use.

Sample loading: 1-2 ml, concentration: 100 mg/ml in 10% acetonitrile/TFA.

Gradient elution condition: 10-80% acetonitrile in a total volume of 500 ml.

Monitor absorption wavelength: at 254 nm.

Fraction Collector: 5 ml/fractions (collect from 10% to 72% acetonitrile)

Instrument: AKTA-FPLC, P920 pump; Monitor UPC-900; Frac-900.

(B) Isolation of Component Ys with Preparative HPLC

Methods

Column: A preparative HPLC column (Waters Delta Pak C18-300A);

Elution conditions: 45% acetonitrile isocratic elution with flow rate of 1 ml/min. Fractions are monitored at 207 nm and were collected and lyophilized.

Experiment 5

Determination of the Chemical Structure

Methods

NMR analysis. The pure compound Y of Xanthoceras sorbifolia was dissolved in pyridine-D5 with 0.05% v/v TMS. All NMR spectra were acquired using a Bruker Avance 600 MHz NMR spectrometer with a QXI probe (1H/13C/15N/31P) at 298 K. The numbers of scans for 1D 1H spectra were 16 to 128, depending on the sample concentration. 2D HMQC spectra were recorded with spectral widths of 6000×24,000 Hz and data points of 2024×256 for t2 and t1 dimensions, respectively. The number of scans was 4 to 128. 2D HMBC were acquired with spectral widths of 6000×30,000 Hz and data points of 2024×512 for t2 and t1 dimensions, respectively. The number of scans was 64. The 2D data were zero-filled in t1 dimension to double the data points, multiplied by cosine-square-bell window functions in both t1 and t2 dimensions, and Fourier-transformed using software XWIN-NMR. The final real matrix sizes of these 2D spectra are 2048×256 and 2048×512 data points (F2×F1) for HMQC and HMBC, respectively.

Mass spectral analysis. The mass of samples was analyzed by (A) MALDI-TOF Mass Spectrometry and by (B) ESI-MS Mass spectrometry. (A) Samples for MALDI-TOF were first dissolved in acetonitrile, and then mixed with the matrix CHCA, i.e., Alpha-cyano-4-hydroxycinnamic acid, 10 mg CHCA/mL in 50:50 water/acetonitrile and 0.1% TFA in final concentration. The molecular weight was determined by the high resolution mass spectroscope analysis with standards. (B) For ESI, the sample was analyzed with LCQ DECA XP Plus machine made by Thermo Finnigan. It is ionized with ESI source and the solvent for the compound is acetonitrile.

Experiment 6

Determination the Anti Virus Activities of Compound of this Invention

The major procedures for the determination of antivirus activity are:

A. Determine the production of HIV virus after a non-lethal dosage of compound is added to the viral culture system.

B. Determine the growth activity of HIV virus after contact to compound. The steps for these experiments are:
1. Pre-treat HIV virus with different dosages of test compound for variable length of time.
2. Mix treated virus with cells.
3. Measure Virus production.
4. Negative control: no virus in cell.
5. Positive control—untreated virus mixed with cell.
Result: The virus growth is inhibited after treatments of compound of this invention.

Experiment 7

Determination the Treatment of Venous Insufficiency Particularly Hemorrhoids by Compound (Y) of this Invention 1) 5 groups of rats:
2) 3 dose groups (low, mid, high), 1 positive control (no drug, with croton oil), 1 negative control (no drug, no croton Oil)
3) Give drug (Compound Y) for 7 days in 3 dose groups (low, mid, high) of rats.
4) On day 7, apply croton oil to the Give-Drug-groups after giving drug.
5) At the 24$^{th}$ hour after applying croton oil, isolate the recto-anus tissue (10 mm) of rats.
6) Apply croton oil to control group. At the 24$^{th}$ hour after applying *croton* oil, isolate the recto-anus tissue (10 mm) of rats.
7) Compare the swelling of give-drug-groups with positive control (no drug, with croton oil) and negative control (no drug, no croton oil).
8) The result shows that Compound Y inhibiting the swelling of recto-annus induced by croton oil.

Experiment 8

Determination the Treatment of Leg Swelling by Compound (Y) of this Invention 1) 5 groups of rats:
2) 3 dose groups (low, mid, high), 1 positive control (no drug, with Carrageenin), 1 negative control (no drug, no Carrageenin)
3) Give drug (Compound Y) for 7 days in 3 dose groups (low, mid, high) of rats.
4) On day 7, apply Carrageenin to the Give-Drug-groups after giving drug 10 min.
5) Measure the swell volume of the paw of rats at 0.5, 1, 2, 4, 6 hours after applying the Carrageenin.
6) Compare the swelling of give-drug-groups with positive control (no drug, with Carrageenin) and negative control (no drug, no Carrageenin).
7) The result shows that Compound Y inhibiting the leg swelling.

What is claim is:

1. A method for inhibiting ovarian or skin cancer cell growth in a subject comprising administering to the subject an effective amount of a compound, or its salt or ester thereof, selected from formula,

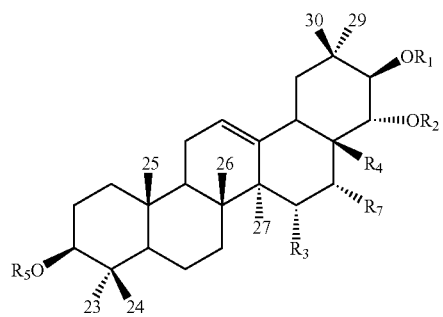

wherein R1 is selected from a group consisting of alkanoyl, alkenoyl, acyl, and sugar moiety with alkenoyl; and R2 is selected from a group consisting of hydrogen, alkanoyl, alkenoyl, acyl, and sugar moiety with alkenoyl; R3 represents H or OH; R4 is selected from a group consisting of CH2OH, and CH2Oacyl; R5 represents hydrogen; R7 is OH; and each of positions 23, 24, 25, 26, 29, 30 of the compound is a methyl group, wherein each methyl group may be independently substituted with alkyl or hydroxyl group; wherein the alkanoyl is acetyl; wherein the alkenoyl is angeloyl; wherein the acyl is acetyl or angeloyl.

2. The method of claim 1, wherein R1 is selected from a group consisting of angeloyl, acetyl group and sugar moiety substituted with two angeloyl groups, wherein the sugar moiety is rhamnose.

3. The method of claim 1, wherein R2 is selected from a group consisting of hydrogen, angeloyl, acetyl group, and sugar moiety with alkenoyl.

4. The method of claim 1, wherein R4 is CH2OH.

5. The method of claim 1, wherein R4 is CH2Oacetyl.

6. The method of claim 1, wherein position 24 of the compound is substituted with hydroxyl group.

7. The method of claim 1, wherein each of positions 23, 24, 25, 26, 29, 30 of the compound is independently substituted with hydroxyl group.

8. The method of claim 1, wherein each of positions 23, 24, 25, 26, 29 and 30 of the compound is methyl group.

9. A method for inhibiting ovarian cancer cell growth in a subject, by administering to the subject an effective amount of a compound, or its salt or ester thereof, selected from formula,

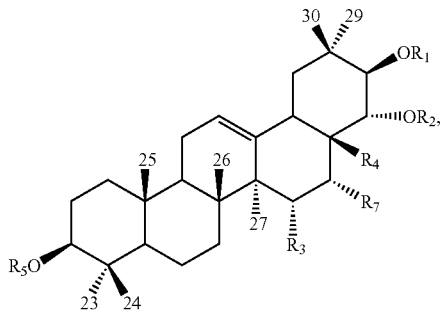

wherein R1 is selected from a group consisting of, alkanoyl, alkenoyl, acyl, and sugar moiety with acyl group; R2 is selected from a group consisting of hydrogen, alkanoyl, alkenoyl, acyl, and sugar moiety with alkenoyl; R3 represents H or OH; R4 is selected from a group consisting of CH2OH, CH2Oacyl; R5 is one or more sugar moieties linked via glycosidic bonds, wherein the sugar moieties are selected from glucose, galactose, arabinose, and their salt, ester or acid thereof; R7 is H or OH; and each of positions 23, 24, 25, 26, 29, 30 of the compound is a methyl, wherein each of the methyl groups may be independently substituted with alkyl or hydroxyl group; wherein the alkanoyl is acetyl; wherein the alkenoyl is angeloyl; wherein the acyl is acetyl or angeloyl.

10. The method of claim 9, wherein R5 represents one or more sugar moieties linked via glycosidic bonds, wherein the sugar moieties is/are glucopyranosyl, arabinofuranosyl or glucuronopyranosyl.

11. The method of claim 9, wherein R5 represents one or more sugar moieties linked via glycosidic bonds, wherein the sugar moieties is/are galactopyranosyl, arabinofuranosyl or glucuronopyranoside butyl ester.

12. The method of claim 9, wherein R5 represents at least three sugar moieties linked via glycosidic bonds, wherein the sugar moieties are selected from D-glucose, D-galactose, L-arabinose, alduronic acid, D-glucuronic acid, D-galacturonic acid, and their acid, ester or salt thereof.

13. The method of claim 9, wherein R1 is selected from a group consisting of angeloyl, acetyl group and sugar moiety with two angeloyl groups, wherein the sugar moiety is rhamnose.

14. The method of claim 9, wherein R4 is CH2OH.

15. The method of claim 9, wherein R2 is selected from a group consisting of angeloyl and acetyl group.

16. The method of claim 9, wherein R4 is CH2OAcetyl.

17. The method of claim 9, wherein position 24 is substituted with hydroxyl group.

18. The method of claim 9, wherein the method is for inhibiting ovarian cancer cell growth.

19. The method of claim 9, wherein wherein R5 represents one or more sugar moieties linked via glycosidic bonds, wherein the sugar moieties is/are galactopyranosyl, arabinofuranosyl or glucuronopyranosyl.

20. The method of claim 9, wherein the compound has at least two acyl groups; wherein the acyl groups are selected from a group consisting of angeloyl, and acetyl, wherein the acyl groups are attached to one or more sugar moieties.

21. The method of claim 1, wherein R4 represents CH2OAcetyl.

22. The method of claim 1, wherein the compound has at least two acyl groups; wherein the acyl groups are selected from acetyl and angeloyl.

23. The method of claim 9, wherein the compound is selected from the following structures:
A) 3-O-[β-D-galactopyranosyl(1→2)]-α-L-arabinofuranosyl -(1→3)-β-D-glucuronopyranosyl-21,22-O-diangeloyl-3β, 15α, 16α, 21β, 22α, 28-hexahydroxyolean-12-ene, (Y3/Y)

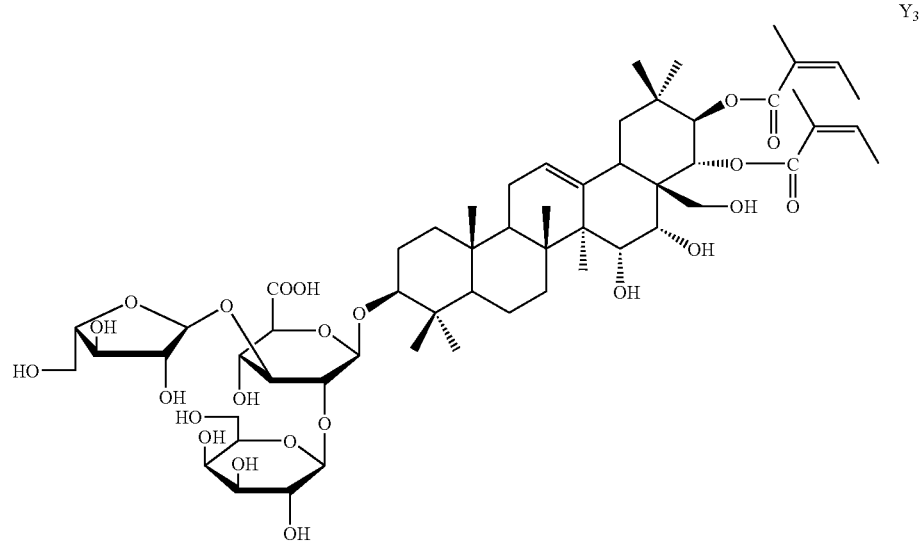

B) 3-O-[β-D-galactopyranosyl(1→2)]-α-L-arabinofuranosyl -(1→3)-β-D-glucuronopyranosyl-21-O-(3,4-diangeloyl)-α-L -rhamnophyranosyl-22-O-acetyl-3β, 16α, 21β, 22α, 28-pentahydroxyolean-12-ene; (Y1),
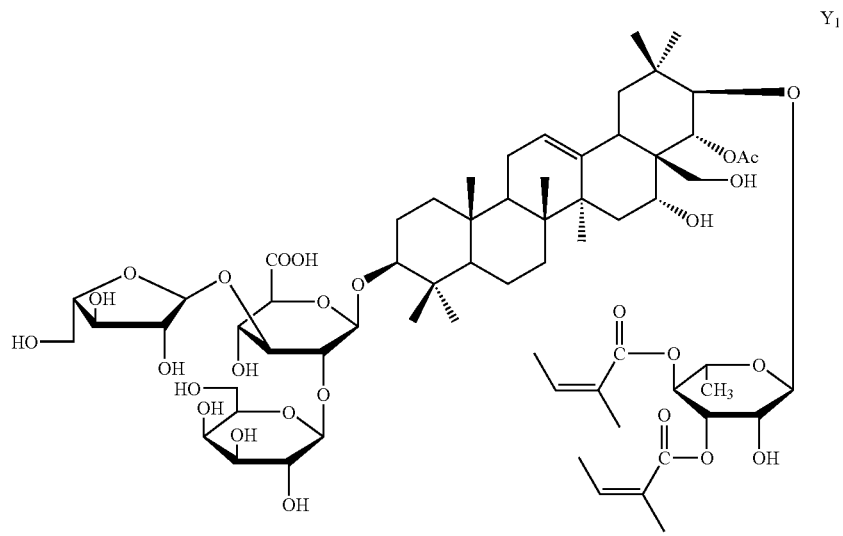
C) 3-O-[β-D-glucopyranosyl-(1→2)]-α-L -arabinofuranosyl-(1→3)-(-D-glucuronopyranosyl-21, 22-O-diangeloyl-3β, 15α, 16α, 21β, 22α, 24β, 28-heptahydroxyolean-12-ene; (Y2),
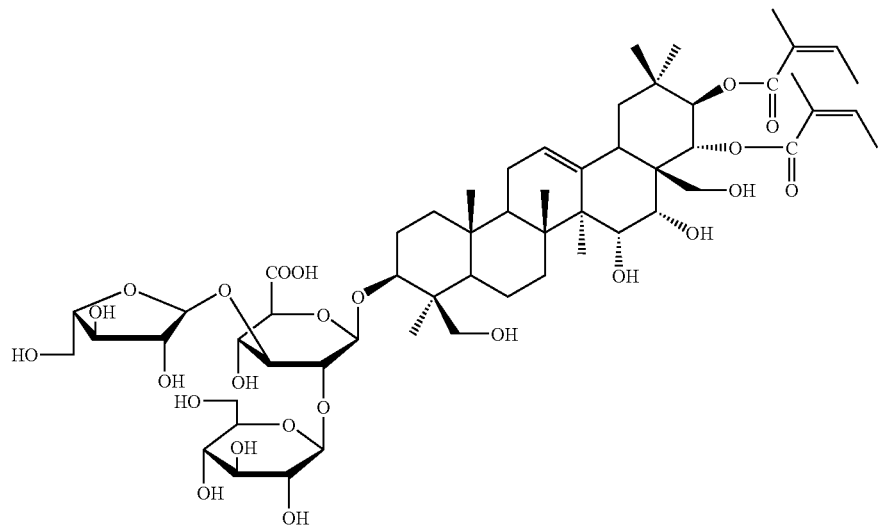

D) 3-O-[β-glucopyranosyl(1→2)]-α-arabinofuranosyl (1→3)-β-glucuronopyranosyl-21,22-O-diangeloyl-3β, 16α, 21β, 22α, 28-hexahydroxyolean-12-ene; (Y8),
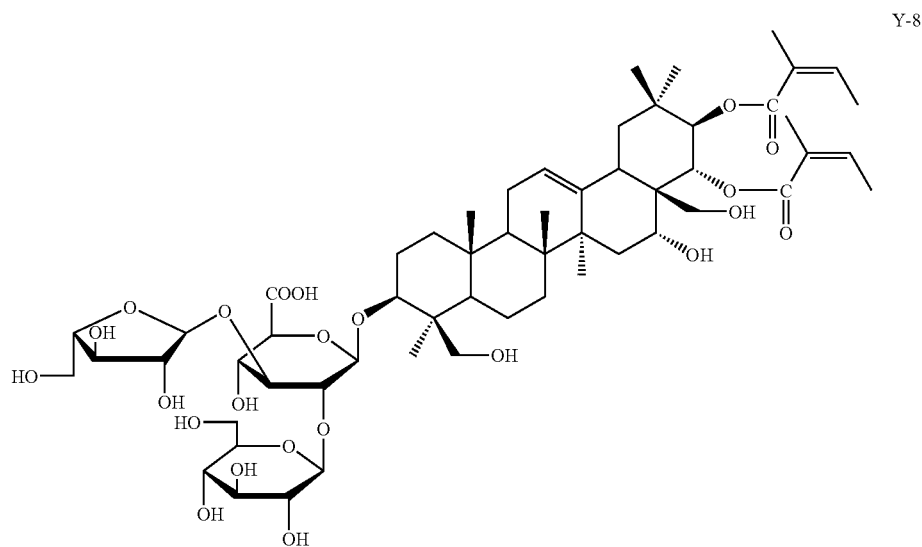
E) 3-O-[β-galactopyranosyl(1→2)]-α-arabinofuranosyl (1→3)-β-glucuronopyranosyl-21-O-(3,4-diangeloyl)-α-rhamnopyranosyl-28-O-acetyl-3β, 16α, 21β, 22α, 28-pentahydroxyolean-12-ene; (Y9),
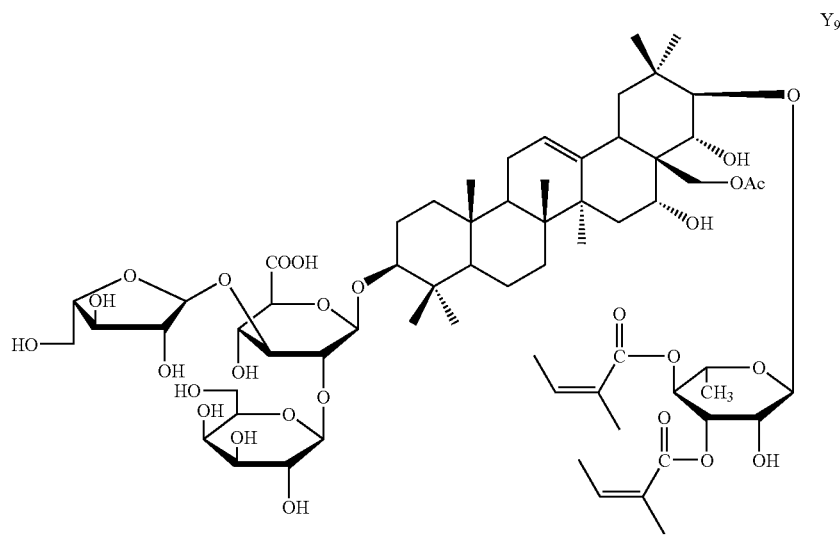

F) 3-O-[β-galactopyranosyl(1→2)]-α-arabinofuranosyl(1→3)-β-glucuronopyranosyl-21, 22-O-diangeloyl-3β, 16α, 21β, 22α, 28-pentahydroxyolean-12-ene; (Y10)
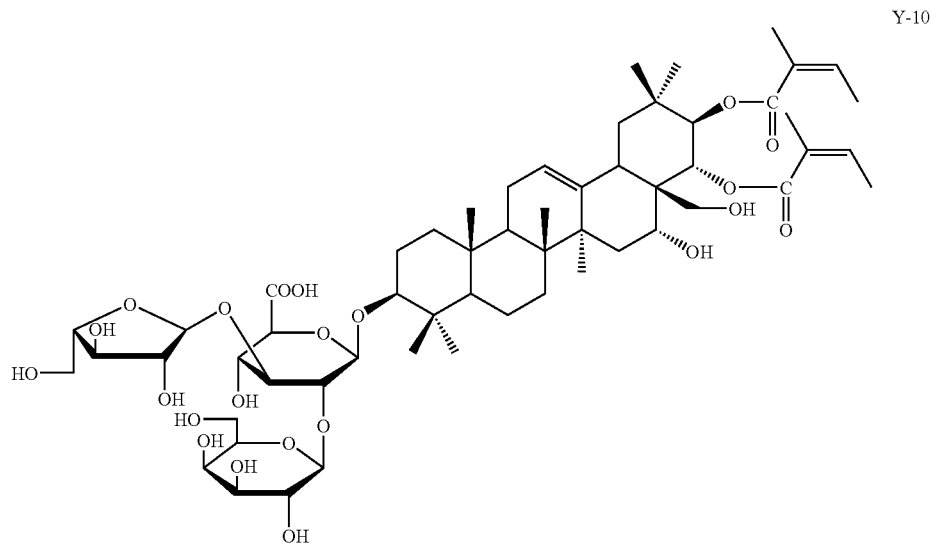
Y-10
G) 3-O-{[β-D-galactopyranosyl(1→2)]-[α-L-arabinofuranosyl (1→3)]-β-D-glucuronopyranoside butyl ester}-21-O-acetyl-22-O-angeloyl-3β, 16α, 21β, 22α, 28-pentahydroxyolean-12-ene; (X),
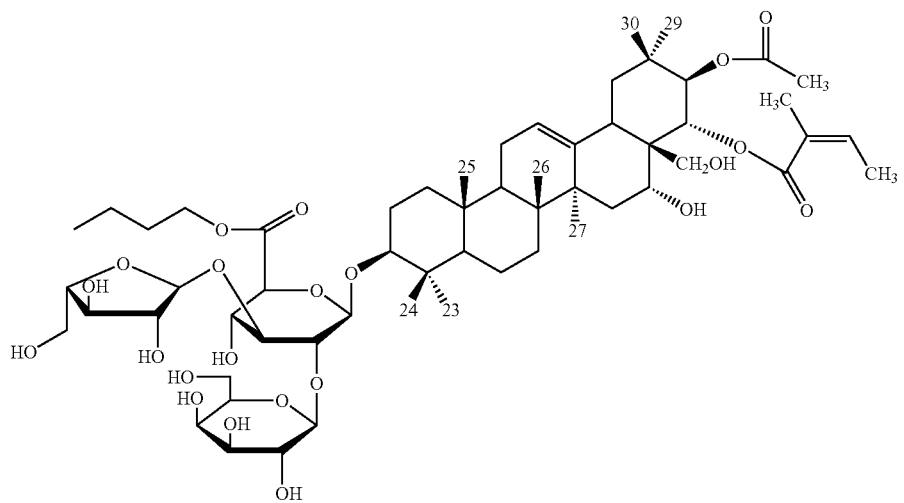
* * * * *